US012702482B2

(12) United States Patent
Casey et al.

(10) Patent No.: US 12,702,482 B2
(45) Date of Patent: Aug. 11, 2026

(54) TECHNIQUES TO MAP THREE-DIMENSIONAL HUMAN ANATOMY DATA TO TWO-DIMENSIONAL HUMAN ANATOMY DATA

(71) Applicant: Carlsmed, Inc., Carlsbad, CA (US)

(72) Inventors: Niall Patrick Casey, Carlsbad, CA (US); Jeffery Pennal, San Diego, CA (US); Rodrigo Junqueira Nicolau, Cardiff, CA (US); Matthew Chen, San Diego, CA (US); Austin Wulf, Carlsbad, CA (US); Jeremy Winston, San Diego, CA (US)

(73) Assignee: Carlsmed, Inc., Carlsbad, CA (US)

( * ) Notice: Subject to any disclaimer, the term of this patent is extended or adjusted under 35 U.S.C. 154(b) by 325 days.

(21) Appl. No.: 18/373,899

(22) Filed: Sep. 27, 2023

(65) Prior Publication Data

US 2024/0252248 A1 Aug. 1, 2024

Related U.S. Application Data

(63) Continuation-in-part of application No. 18/102,444, filed on Jan. 27, 2023, now Pat. No. 11,793,577.

(51) Int. Cl.

*A61B 34/10* (2016.01)
*A61B 34/00* (2016.01)
*G06T 7/33* (2017.01)

(52) U.S. Cl.

CPC .............. *A61B 34/10* (2016.02); *A61B 34/25* (2016.02); *G06T 7/344* (2017.01);
(Continued)

(58) Field of Classification Search

CPC ... A61B 34/10; A61B 2034/105; G06T 7/344; G06T 2200/04; G06T 2207/30012
See application file for complete search history.

(56) References Cited

U.S. PATENT DOCUMENTS

| | | | |
|---|---|---|---|
| 4,704,686 | A | 11/1987 | Aldinger |
| 4,936,862 | A | 6/1990 | Walker et al. |

(Continued)

FOREIGN PATENT DOCUMENTS

| | | | |
|---|---|---|---|
| CN | 104318009 | A | 1/2015 |
| CN | 104353121 | A | 2/2015 |

(Continued)

OTHER PUBLICATIONS

International Search Report and Written Opinion mailed May 30, 2024 in International Patent Application No. PCT/US24/10943, 19 pages.

(Continued)

*Primary Examiner* — Molly Wilburn
(74) *Attorney, Agent, or Firm* — Ashurst Perkins Coie US LLP

(57) ABSTRACT

Systems and methods for designing and implementing patient-specific surgical procedures and/or medical devices are disclosed. An example method includes obtaining a first multi-dimensional image data of an anatomical region of a patient in a first loading state; determining, from the first multi-dimensional image data, regions corresponding to anatomical elements of a spine; identifying, in each region, a first set of landmarks; obtaining a second multi-dimensional image data of the anatomical region comprising the spine of the patient in a second loading state; identifying a second set of landmarks from the second multi-dimensional image data that map to the first set of landmarks; obtaining an aligned multi-dimensional image data of the patient's spine; generating a design for a medical implant based on spinopelvic parameters measured from the aligned multi-dimensional image data; and causing a medical implant to be manufactured by sending the design for the medical implant to a manufacturing device.

34 Claims, 18 Drawing Sheets

(52) U.S. Cl.
CPC ..... *A61B 2034/105* (2016.02); *G06T 2200/04* (2013.01); *G06T 2207/10081* (2013.01); *G06T 2207/10088* (2013.01); *G06T 2207/10116* (2013.01); *G06T 2207/30012* (2013.01)

(56) References Cited

U.S. PATENT DOCUMENTS 5,431,562 A 7/1995 Andreiko et al.
D420,995 S 2/2000 Imamura
D436,580 S 1/2001 Navano
6,315,553 B1 11/2001 Sachdeva
6,540,512 B1 4/2003 Sachdeva
6,696,073 B2 2/2004 Boyce et al.
6,772,026 B2 8/2004 Bradbury
6,932,842 B1 8/2005 Litschko et al.
6,978,188 B1 12/2005 Christensen
6,988,241 B1 1/2006 Guttman
7,174,282 B2 2/2007 Hollister et al.
7,187,790 B2 3/2007 Sabol et al.
D548,242 S 8/2007 Viegers
D614,191 S 4/2010 Takano
7,747,305 B2 6/2010 Dean et al.
7,756,314 B2 7/2010 Karau et al.
7,799,077 B2 9/2010 Lang
D633,514 S 3/2011 Tokunaga
D656,153 S 3/2012 Imamura
8,160,677 B2 * 4/2012 Gielen ................. G06V 10/245 600/407
8,246,680 B2 8/2012 Betz
8,265,949 B2 9/2012 Haddad
8,275,594 B2 9/2012 Lin
8,337,507 B2 12/2012 Lang
8,394,142 B2 3/2013 Bertagnoli
8,457,930 B2 6/2013 Shroeder
8,532,806 B1 9/2013 Masson
8,556,983 B2 10/2013 Bojarski et al.
8,617,171 B2 * 12/2013 Park .................. A61B 17/1675 606/88
8,644,568 B1 2/2014 Hoffman
8,735,773 B2 5/2014 Lang
8,758,357 B2 6/2014 Frey
8,775,133 B2 7/2014 Schroeder
8,781,557 B2 7/2014 Dean
8,843,229 B2 9/2014 Vanasse
8,855,389 B1 10/2014 Hoffman
8,870,889 B2 10/2014 Frey
9,020,788 B2 4/2015 Lang
D735,231 S 7/2015 Omiya
D737,309 S 8/2015 Kito
9,198,678 B2 12/2015 Frey et al.
9,208,558 B2 12/2015 Dean
D757,025 S 5/2016 Kim
D761,842 S 7/2016 Johnson
9,411,939 B2 8/2016 Furrer
9,445,907 B2 9/2016 Meridew
9,452,050 B2 9/2016 Miles et al.
D774,076 S 12/2016 Fuller
9,542,525 B2 1/2017 Arisoy et al.
9,642,633 B2 5/2017 Frey et al.
9,693,831 B2 7/2017 Mosnier et al.
9,707,058 B2 7/2017 Bassett
9,715,563 B1 7/2017 Schroeder
D797,760 S 9/2017 Tsujimura
D797,766 S 9/2017 Ibsies
D798,312 S 9/2017 Tsujimura
9,757,245 B2 9/2017 O'Neil et al.
D798,894 S 10/2017 Ibsies
9,775,680 B2 10/2017 Bojarski et al.
9,782,228 B2 10/2017 Mosnier et al.
D812,628 S 3/2018 Okado
9,993,341 B2 6/2018 Vanasse
10,034,676 B2 7/2018 Donner
D825,605 S 8/2018 Jann
D826,977 S 8/2018 Nakajima
10,089,413 B2 10/2018 Wirx-Speetjens et al.
D841,675 S 2/2019 Hoffman
10,213,311 B2 2/2019 Mafhouz
D845,973 S 4/2019 Jaycobs
D845,974 S 4/2019 Cooperman
D847,165 S 4/2019 Kolbenheyer
D848,468 S 5/2019 Ng
D849,029 S 5/2019 Cooperman
D849,773 S 5/2019 Jiang
10,292,770 B2 5/2019 Ryan
10,299,863 B2 5/2019 Grbic et al.
D854,560 S 7/2019 Field
D854,561 S 7/2019 Field
10,390,958 B2 8/2019 Maclennan
D860,237 S 9/2019 Li
D860,238 S 9/2019 Bhardwaj
D866,577 S 11/2019 Eisert
D867,379 S 11/2019 Ang
D867,389 S 11/2019 Jamison
10,463,433 B2 11/2019 Turner et al.
D870,762 S 12/2019 Mendoza
10,512,546 B2 12/2019 Kamer et al.
10,517,681 B2 12/2019 Roh et al.
D872,117 S 1/2020 Kobayashi
D872,756 S 1/2020 Howell
D874,490 S 2/2020 Dodsworth
D875,761 S 2/2020 Heffernan
D876,454 S 2/2020 Knowles
D876,462 S 2/2020 Li
D877,167 S 3/2020 Knowles
D879,112 S 3/2020 Hejazi
10,588,589 B2 3/2020 Bregman-Amitai et al.
10,603,055 B2 3/2020 Donner et al.
D880,513 S 4/2020 Wang
D881,908 S 4/2020 Sunil
D881,910 S 4/2020 Lin
10,621,289 B2 4/2020 Schroeder
10,631,988 B2 4/2020 Arnold et al.
D884,008 S 5/2020 Thornberg
10,646,236 B2 5/2020 Donner et al.
10,646,258 B2 5/2020 Donner et al.
10,736,698 B2 8/2020 Bohl
10,751,188 B2 8/2020 Guo et al.
D896,825 S 9/2020 Abel
D896,828 S 9/2020 Linares
D898,054 S 10/2020 Everhart
D899,438 S 10/2020 Crafts
10,806,597 B2 10/2020 Sournac et al.
10,902,944 B1 1/2021 Casey et al.
10,937,237 B1 3/2021 Kim et al.
D916,868 S 4/2021 Evangeliou
D916,879 S 4/2021 Mitsumori
D918,253 S 5/2021 Choe
11,000,334 B1 * 5/2021 Young ..................... G06T 7/251
D921,675 S 6/2021 Kmak
D921,677 S 6/2021 Kmak
D921,687 S 6/2021 Kmak
D924,909 S 7/2021 Nasu
D925,567 S 7/2021 Hayamizu
D927,528 S 8/2021 Heisler
11,083,586 B2 8/2021 Cordonnier
11,112,770 B2 9/2021 Roh et al.
D933,692 S 10/2021 Smith
11,166,764 B2 11/2021 Roh et al.
D937,870 S 12/2021 Pinto
D937,876 S 12/2021 Harvey
D938,461 S 12/2021 Hoffman
D938,986 S 12/2021 Grossberg
D940,178 S 1/2022 Ang
D946,022 S 3/2022 Nuttbrown
D946,023 S 3/2022 Nuttbrown
D946,024 S 3/2022 Vogler-Ivashchanka
D946,616 S 3/2022 Tsai
D958,151 S 7/2022 Casey et al.
11,376,076 B2 7/2022 Casey et al.
11,432,943 B2 9/2022 Casey et al.
11,439,514 B2 9/2022 Casey et al.
11,497,559 B1 11/2022 Roh et al.
11,553,969 B1 * 1/2023 Lang .................. G02B 27/0172
11,793,577 B1 10/2023 Casey et al.

(56) References Cited

U.S. PATENT DOCUMENTS

2004/0104512 A1 6/2004 Eidenschink
2005/0234555 A1 10/2005 Sutton et al.
2005/0273170 A1 12/2005 Navarro et al.
2007/0270680 A1 11/2007 Sheffer et al.
2007/0272747 A1 11/2007 Woods et al.
2007/0276369 A1 11/2007 Allard et al.
2007/0276501 A1 11/2007 Betz
2008/0089566 A1* 4/2008 Node-Langlois ......... G06T 7/30 382/128
2008/0227047 A1 9/2008 Lowe
2009/0062739 A1 3/2009 Anderson
2010/0191088 A1* 7/2010 Anderson .............. A61B 34/20 606/300
2010/0324692 A1 12/2010 Uthgenannt
2011/0196451 A1 8/2011 Hill
2012/0150243 A9 6/2012 Crawford et al.
2012/0322018 A1 12/2012 Lowe
2013/0323669 A1 12/2013 Lowe
2014/0072608 A1 3/2014 Karagkiozaki
2014/0074438 A1 3/2014 Furrer
2014/0081659 A1 3/2014 Nawana et al.
2014/0086780 A1 3/2014 Miller
2014/0100886 A1 4/2014 Woods
2014/0164022 A1 6/2014 Reed
2014/0263674 A1 9/2014 Cerveny
2014/0277487 A1 9/2014 Davenport et al.
2014/0350614 A1 11/2014 Frey
2015/0079533 A1 3/2015 Lowe
2015/0089590 A1 3/2015 Krishnan et al.
2015/0105891 A1 4/2015 Golway et al.
2015/0150523 A1 6/2015 Sirpad
2015/0199488 A1 7/2015 Falchuk
2015/0213225 A1 7/2015 Amarasingham
2015/0324490 A1* 11/2015 Page .................. G06Q 30/0621 700/98
2015/0328004 A1 11/2015 Mafhouz
2015/0332018 A1 11/2015 Rosen
2016/0001039 A1 1/2016 Armour et al.
2016/0015465 A1 1/2016 Steines et al.
2016/0030067 A1 2/2016 Frey et al.
2016/0045317 A1 2/2016 Lang
2016/0074048 A1 3/2016 Pavlovskaia
2016/0081810 A1 3/2016 Reiley et al.
2016/0117817 A1 4/2016 Seel
2016/0143744 A1 5/2016 Bojarski et al.
2016/0184054 A1 6/2016 Lowe
2016/0210374 A1 7/2016 Mosnier et al.
2016/0217268 A1 7/2016 Otto
2016/0242857 A1 8/2016 Scholl
2016/0300026 A1* 10/2016 Bogoni .................. G16H 10/60
2016/0354039 A1 12/2016 Soto et al.
2016/0354213 A1 12/2016 Cowan
2016/0378919 A1 12/2016 McNutt et al.
2017/0000566 A1 1/2017 Gordon
2017/0014169 A1 1/2017 Dean
2017/0020679 A1 1/2017 Maclennan
2017/0035514 A1 2/2017 Fox et al.
2017/0061375 A1 3/2017 Laster
2017/0068792 A1 3/2017 Reiner
2017/0112548 A1 4/2017 Alamin et al.
2017/0135706 A1 5/2017 Frey et al.
2017/0143494 A1 5/2017 Mahfouz
2017/0143831 A1 5/2017 Varanasi et al.
2017/0196499 A1 7/2017 Hunter
2017/0216047 A1 8/2017 Hawkes et al.
2017/0220740 A1 8/2017 D'Urso
2017/0252107 A1* 9/2017 Turner ..................... G06N 5/04
2017/0262595 A1 9/2017 Vorhis
2017/0340447 A1 11/2017 Mahfouz
2017/0354510 A1 12/2017 O'Neil et al.
2017/0367645 A1 12/2017 Klinder
2018/0008349 A1 1/2018 Gillman
2018/0113992 A1 4/2018 Eltorai et al.
2018/0116727 A1 5/2018 Caldwell et al.
2018/0168499 A1 6/2018 Bergold
2018/0168731 A1 6/2018 Reid
2018/0185075 A1 7/2018 She
2018/0233222 A1 8/2018 Daley
2018/0233225 A1 8/2018 Experton
2018/0250075 A1 9/2018 Cho
2018/0303552 A1* 10/2018 Ryan .................. A61B 17/7002
2018/0303616 A1 10/2018 Bhattacharyya et al.
2018/0308569 A1 10/2018 Luellen
2018/0338841 A1 11/2018 Miller et al.
2019/0065685 A1 2/2019 Pickover
2019/0069956 A1 3/2019 Ryan et al.
2019/0099221 A1 4/2019 Schmidt et al.
2019/0103190 A1* 4/2019 Schmidt ................ G06T 7/0012
2019/0175277 A1 6/2019 Chav
2019/0201106 A1 7/2019 Siemionow
2019/0262084 A1 8/2019 Roh et al.
2019/0266597 A1 8/2019 Mohtar
2019/0274735 A1 9/2019 Drozd et al.
2019/0328929 A1 10/2019 Kugler et al.
2019/0333622 A1 10/2019 Levin
2019/0354693 A1 11/2019 Yoon
2019/0380792 A1 12/2019 Poltaretskyi et al.
2019/0388131 A1 12/2019 Mehl et al.
2020/0021570 A1 1/2020 Lin
2020/0078180 A1 3/2020 Casey et al.
2020/0085509 A1 3/2020 Roh et al.
2020/0170802 A1* 6/2020 Casey .................... G16H 50/50
2020/0258605 A1 8/2020 Blechman
2020/0261156 A1 8/2020 Schmidt
2020/0289288 A1 9/2020 Müller et al.
2020/0315708 A1 10/2020 Mosnier et al.
2021/0059822 A1* 3/2021 Casey .................. A61F 2/4425
2021/0064605 A1 3/2021 Balint
2021/0145519 A1 5/2021 Mosnier et al.
2021/0169576 A1 6/2021 Ryan et al.
2021/0192759 A1 6/2021 Lang
2021/0210189 A1 7/2021 Casey et al.
2021/0259776 A1 8/2021 Upadrasta et al.
2021/0287770 A1 9/2021 Anderson
2021/0382457 A1* 12/2021 Roh ................... G05B 19/4099
2022/0000625 A1 1/2022 Cordonnier
2022/0006642 A1 1/2022 Maj et al.
2022/0013211 A1 1/2022 Steinberg et al.
2022/0031396 A1 2/2022 Ryan et al.
2022/0039965 A1 2/2022 Casey et al.
2022/0047402 A1 2/2022 Casey et al.
2022/0110686 A1 4/2022 Roh et al.
2022/0151699 A1* 5/2022 Schmidt ................. A61B 34/10
2022/0160405 A1 5/2022 Casey et al.
2022/0160518 A1 5/2022 Casey et al.
2022/0211507 A1 7/2022 Simoes
2022/0387191 A1 12/2022 Cordonnier
2022/0401150 A1 12/2022 Cordonnier
2022/0409140 A1 12/2022 Cordonnier
2023/0000560 A1 1/2023 Roh et al.
2023/0014384 A1 1/2023 Cordonnier
2023/0016297 A1 1/2023 Gillman
2023/0023440 A1 1/2023 Casey et al.
2023/0034731 A1 2/2023 Cordonnier
2023/0052263 A1 2/2023 Casey et al.
2023/0104580 A1 4/2023 Roh et al.
2023/0310084 A1* 10/2023 Zhang .................... G16H 50/50 606/1
2024/0115398 A1 4/2024 Frey
2024/0225531 A1 7/2024 Casey et al.
2024/0261029 A1 8/2024 Casey et al.

FOREIGN PATENT DOCUMENTS

CN 204468348 U 7/2015
CN 105796214 A 7/2016
CN 106202861 12/2016
CN 107220933 9/2017
CN 108670506 A 10/2018
CN 110575289 A 12/2019
CN 111281613 A 6/2020
CN 112155792 A 1/2021
CN 113643790 11/2021
EP 3120796 A1 1/2017

(56) References Cited

FOREIGN PATENT DOCUMENTS

| | | | |
|---|---|---|---|
| WO | 9507509 | A1 | 3/1995 |
| WO | 2004110309 | A2 | 12/2004 |
| WO | 2010151564 | A1 | 12/2010 |
| WO | 2012154534 | A1 | 11/2012 |
| WO | 2014180972 | A2 | 11/2014 |
| WO | 2016172694 | A1 | 10/2016 |
| WO | 2017116346 | A1 | 7/2017 |
| WO | 2019112917 | A1 | 6/2019 |
| WO | 2019148154 | A1 | 8/2019 |
| WO | 2019165152 | A1 | 8/2019 |
| WO | 2019241167 | A1 | 12/2019 |
| WO | 2020055874 | A1 | 3/2020 |
| WO | 2022045956 | A1 | 3/2022 |
| WO | 2022124916 | A1 | 6/2022 |
| WO | 2023034405 | A1 | 3/2023 |
| WO | 2024064299 | A1 | 3/2024 |

OTHER PUBLICATIONS

International Search Report and Written Opinion mailed Jul. 5, 2024 in International Patent Application No. PCT/US24/14514, 14 pages.

Pyo et al., "Methods Used to Assess the 3D Accuracy of Dental Implant Positions in Computer-Guided Implant: A Review.," Jour. Of Clin. Med., vol. 8(1): 54, Issue 07, Jan. 2019, 12 pages.

Endo, Kenji et al. "Measurement of whole spine sagittal alignment using the SLOT radiography of the SONIALVISION safire series clinical application." Medical Now, No. 78; Aug. 2015, 4 pages.

International Search Report and Written Opinion mailed Feb. 8, 2024 in International Patent Application No. PCT/US23/33896, 17 pages.

Materialise Mimics, "Efficiently turn scans into accurate virtual 3D models," Retrieved on Nov. 1, 2019 at www. materialize.com/en/medical/software/mimics, 1 page.

Pimenta, Dr. Luiz, "Current Surgical Strategies to Restore Proper Sagittal Alignment," Journal of Spine 2015, vol. 4, Issue 4, 2 pages.

U.S. Appl. No. 15/958,409 for Ryan, filed Apr. 21, 2017.

U.S. Appl. No. 17/463,054 for Casey et al., filed Aug. 31, 2021.

U.S. Appl. No. 17/518,524 for Cordonnier, filed Nov. 3, 2021.

U.S. Appl. No. 17/678,874 for Cordonnier, filed Feb. 23, 2022.

U.S. Appl. No. 17/838,727 for Casey et al., filed Jun. 13, 2022.

U.S. Appl. No. 17/878,633 for Cordonnier, filed Aug. 1, 2022.

U.S. Appl. No. 17/880,277 for Casey et al., filed Aug. 3, 2022.

U.S. Appl. No. 18/071,555 for Casey et al. filed Nov. 29, 2022.

* cited by examiner

500

600

700

800

900

1100

1200
Preop
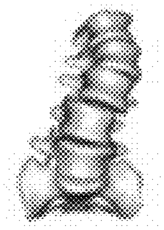
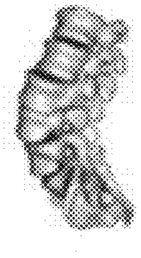
| PREOP | | — PI — LL<br>STANDING X-RAY | 17° LL 8° COR<br>CT SCAN | | -47°<br>PI-LL (CT) |
|---|---|---|---|---|---|
| LVL. | LOR. | ANG. TO S1 | COR. | ANT. (mm) | POST. (mm) |
| L1/L2 | 4 | 17° | 7 | 3.6 | 2.1 |
| L2/L3 | 5 | 60° | 9 | 3.0 | 1.1 |
| L3/L4 | 7 | 55° | -5 | 3.7 | 1.2 |
| L4/L5 | 8 | 40° | -6 | 5.2 | 1.9 |
| L5/S1 | 16 | 28° | -2 | 8.5 | 2.8 |
Plan
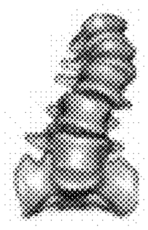
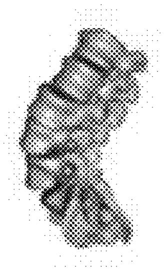
| PLAN | | — PI — LL<br>STANDING X-RAY | 27° LL 9° COR<br>CT SCAN | | -27°<br>PI-LL (CT) |
|---|---|---|---|---|---|
| LVL. | LOR. | ANG. TO S1 | COR. | ANT. (mm) | POST. (mm) |
| L1/L2 | 4 | 27° | 7 | 3.6 | 2.1 |
| L2/L3 | 5 | 60° | 9 | 3.0 | 1.1 |
| L3/L4 | 7 | 60° | -5 | 3.7 | 1.2 |
| L4/L5 | 8 | 50° | -6 | 5.2 | 1.9 |
| L5/S1 | 28 ↑9 | 38° | -3 ↓1 | 14.1 ↑5.6 | 4.9 ↑2.1 |
*FIG. 12*

1300

1400

| | | | | X | Z | Y |
|---|---|---|---|---|---|---|
| 220715.LH.01 | S1 | SUPERIOR | ANTERIOR | 3.37 | -13.37 | -16.81 |
| 220715.LH.01 | S1 | SUPERIOR | POSTERIOR | 1.04 | -0.99 | -2.60 |
| 220715.LH.01 | S1 | SUPERIOR | PATIENT_LEFT | 17.62 | -6.73 | -7.29 |
| 220715.LH.01 | S1 | SUPERIOR | PATIENT_RIGHT | -9.72 | -4.55 | -12.07 |
| 220715.LH.01 | L5 | INFERIOR | ANTERIOR | 3.11 | -2.35 | -27.02 |
| 220715.LH.01 | L5 | INFERIOR | POSTERIOR | 0.78 | 3.17 | -5.40 |
| 220715.LH.01 | L5 | INFERIOR | PATIENT_LEFT | 18.54 | -3.26 | -14.46 |
| 220715.LH.01 | L5 | INFERIOR | PATIENT_RIGHT | -15.14 | 0.23 | -18.41 |
| 220715.LH.01 | L5 | SUPERIOR | ANTERIOR | 5.84 | 28.04 | -27.92 |
| 220715.LH.01 | L5 | SUPERIOR | POSTERIOR | 3.24 | 29.04 | -6.22 |
| 220715.LH.01 | L5 | SUPERIOR | PATIENT_LEFT | 24.86 | 25.44 | -14.70 |
| 220715.LH.01 | L5 | SUPERIOR | PATIENT_RIGHT | -12.03 | 30.38 | -17.69 |
| 220715.LH.01 | L4 | INFERIOR | ANTERIOR | 3.74 | 34.00 | -34.61 |
| 220715.LH.01 | L4 | INFERIOR | POSTERIOR | 3.62 | 33.08 | -9.50 |
| 220715.LH.01 | L4 | INFERIOR | PATIENT_LEFT | 21.43 | 27.08 | -22.58 |
| 220715.LH.01 | L4 | INFERIOR | PATIENT_RIGHT | -12.78 | 35.33 | -22.21 |
| 220715.LH.01 | L4 | SUPERIOR | ANTERIOR | 12.36 | 61.34 | -25.16 |
| 220715.LH.01 | L4 | SUPERIOR | POSTERIOR | 10.30 | 57.48 | -3.96 |
| 220715.LH.01 | L4 | SUPERIOR | PATIENT_LEFT | 27.55 | 54.72 | -15.25 |
| 220715.LH.01 | L4 | SUPERIOR | PATIENT_RIGHT | -4.66 | 63.34 | -15.25 |
| 220715.LH.01 | L3 | INFERIOR | ANTERIOR | 23.21 | 62.07 | -25.48 |
| 220715.LH.01 | L3 | INFERIOR | POSTERIOR | 15.61 | 57.04 | -4.08 |
| 220715.LH.01 | L3 | INFERIOR | PATIENT_LEFT | 35.61 | 51.59 | -12.84 |
| 220715.LH.01 | L3 | INFERIOR | PATIENT_RIGHT | 3.53 | 64.28 | -16.94 |
| 220715.LH.01 | L3 | SUPERIOR | ANTERIOR | 30.57 | 89.08 | -13.32 |
| 220715.LH.01 | L3 | SUPERIOR | POSTERIOR | 25.51 | 79.93 | 6.66 |
| 220715.LH.01 | L3 | SUPERIOR | PATIENT_LEFT | 43.47 | 78.17 | -1.80 |
| 220715.LH.01 | L3 | SUPERIOR | PATIENT_RIGHT | 12.81 | 90.00 | -5.06 |
| 220715.LH.01 | L2 | INFERIOR | ANTERIOR | 37.52 | 86.30 | -4.92 |
| 220715.LH.01 | L2 | INFERIOR | POSTERIOR | 28.77 | 76.75 | 13.22 |
| 220715.LH.01 | L2 | INFERIOR | PATIENT_LEFT | 48.98 | 74.93 | 11.99 |
| 220715.LH.01 | L2 | INFERIOR | PATIENT_RIGHT | 18.71 | 86.40 | -1.99 |
| 220715.LH.01 | L2 | SUPERIOR | ANTERIOR | 42.23 | 110.58 | 12.03 |
| 220715.LH.01 | L2 | SUPERIOR | POSTERIOR | 29.82 | 101.37 | 28.52 |
| 220715.LH.01 | L2 | SUPERIOR | PATIENT_LEFT | 47.06 | 100.26 | 28.88 |
| 220715.LH.01 | L2 | SUPERIOR | PATIENT_RIGHT | 23.48 | 109.47 | 12.34 |
| 220715.LH.01 | L1 | INFERIOR | ANTERIOR | 34.46 | 115.08 | 13.79 |
| 220715.LH.01 | L1 | INFERIOR | POSTERIOR | 25.26 | 101.36 | 32.27 |
| 220715.LH.01 | L1 | INFERIOR | PATIENT_LEFT | 46.74 | 103.87 | 31.11 |
| 220715.LH.01 | L1 | INFERIOR | PATIENT_RIGHT | 14.88 | 107.42 | 15.44 |
| 220715.LH.01 | L1 | SUPERIOR | ANTERIOR | 14.14 | 379.51 | 35.78 |
| 220715.LH.01 | L1 | SUPERIOR | POSTERIOR | 14.09 | 382.96 | 50.32 |
| 220715.LH.01 | L1 | SUPERIOR | PATIENT_LEFT | 25.70 | 382.20 | 43.85 |
| 220715.LH.01 | L1 | SUPERIOR | PATIENT_RIGHT | 3.01 | 382.48 | 44.00 |

*FIG. 14*

TECHNIQUES TO MAP THREE-DIMENSIONAL HUMAN ANATOMY DATA TO TWO-DIMENSIONAL HUMAN ANATOMY DATA

CROSS-REFERENCE TO RELATED APPLICATION

This application is a continuation-in-part of U.S. patent application Ser. No. 18/102,444, filed Jan. 27, 2023, the entirety of which is incorporated herein by reference.

TECHNICAL FIELD

The present disclosure is generally related to designing and implementing techniques for generating medical implants and/or mapping features of a human anatomy captured in different types of multi-dimensional imaging, such as mapping of anatomical features captured in three dimensions (3D) to locations of the features captured in two dimensions (2D).

BACKGROUND

The human anatomy can be imaged using different imaging technologies. For example, a fractured arm can be imaged using X-ray technology to identify the location and/or severity of the fracture. In another example, a computer tomography (CT) scan or magnetic resonance imaging (MRI) can be performed on a portion of a human body to determine issues or anatomical features of the portion of the human body. The different imaging technologies have their own strengths and weaknesses and are used to obtain certain details about the portion of a human body as desired by the physician.

BRIEF DESCRIPTION OF THE DRAWINGS

FIG. 12 illustrates an exemplary surgical plan report that may be used and/or generated in connection with the methods described herein, according to an embodiment.

FIG. 14 illustrates exemplary XYZ and rotation measurements of anatomy of a patient, according to an embodiment.

Figure 1:
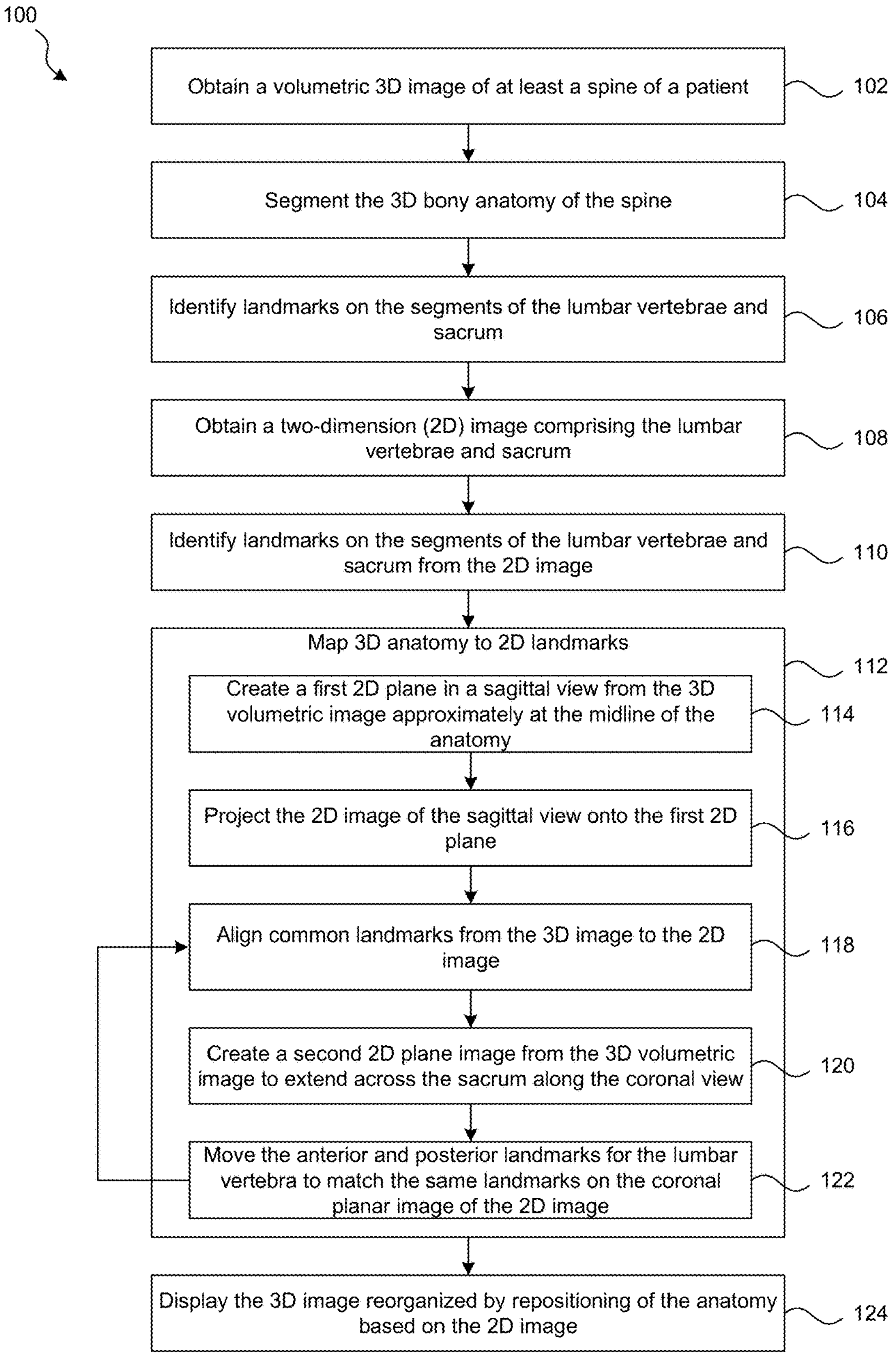
FIG. 1 is a flow diagram illustrating a method for mapping a 3D scan of at least a portion of a human anatomy to a 2D scan of at least the same portion of the human anatomy, according to an embodiment.

The drawings illustrate various embodiments of systems, methods, and embodiments of various other aspects of the disclosure. Any person with ordinary skill in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

The present technology is directed to systems, apparatuses, and methods for mapping image data from image data sets. The image data sets can include different types of scans or images of a portion of a subject. The mapping can compensate for different types of multi-dimensional image data. For example, a three-dimensional (3D) scan or image of at least a portion of a human anatomy can be mapped to locations within two-dimensional (2D) planes of a 2D scan or image of at least the same portion of the human anatomy. One of the technical advantages of the present technology is that it can generate a 3D anatomical data (or 3D model or scan) that is reflective of spatial relationships captured using a 2D scan or image. For example, when a portion of a human anatomy of a patient is imaged or scanned using 3D imaging technology (e.g., computer tomography (CT) scan or magnetic resonance imaging (MRI)), the 3D scanned anatomy of the patient is captured when the patient is lying down or in a horizontal (or non-load-bearing) position. However, such information is desired to be displayed and understood by physicians or surgeons for a patient in a vertical (or loaded or load-bearing) position. In this example, the disclosed technology can map the 3D scanned anatomy of the patient to locations on a 2D image or scan of the portion of the human anatomy of the same patient, where the 2D image or scan is obtained by 2D imaging technology (e.g., X-ray)

when the patient is in a loaded, vertical, or standing position. Generally, compared to 2D imaging technology, 3D imaging technology can produce a higher-resolution image or scan that can provide greater details about the human anatomy. Thus, one of the technical benefits of the disclosed technology is that it can display 3D anatomical data that can have high resolution for a patient in a loaded or load-bearing position. Surgical plans, medical devices, and instruments can be designed based on the 3D anatomical data. The disclosed technology can also determine how to improve an orientation of a spine and/or a position of a vertebra using 3D anatomical data in a load-bearing position.

In some embodiments, a system can obtain images of anatomy of a patient. The system can identify dimensionally constant features and can determine image-capture information. The image-capture information can include, for example, the patient's posture, loading states when images are acquired, etc. The dimensionally constant features can include, for example, bony tissue, implants (e.g., rigid implants), or the like. The system can evaluate images of anatomy in a loaded state (e.g., standing position, upright position, or the like), a non-loaded state (e.g., when the patient is lying down), a pre-set diagnostic posture, etc. The system can correlate the positions of the dimensionally constant features in the images taken during various loading conditions to determine the anatomical change associated with, for example, multiple loading states. The system can have a trained machine learning algorithm that predicts or determines loading state(s) in acquired images based on historical images.

The system can utilize information from all or some of the images to generate anatomical models of the patient. The system can quantify and score the resolution of images based on, for example, pixel sizes, voxel sizes, or spatial resolution (e.g., spacing/number of slices of tomographic images). Smaller pixel or voxel sizes correspond to higher resolutions. Pixel size is determined by dividing the physical dimensions of the image detector (such as the X-ray film or digital sensor) by the number of pixels in the corresponding direction. The resolution assessment methods may be selected depending on the specific imaging modality and the goals of the analysis.

The system can obtain anatomical element geometry from images capable of providing high-definition images, high-resolution images, or other images illustrating surface features of the anatomical elements. The system can determine additional information for anatomical elements in a loading state using images that show loading states. By way of example, CT scans can be analyzed to obtain dimensional information for individual anatomical elements, such as vertebrae, vertebral bodies, or the like. Dimensional information for positioning those anatomical elements can be determined using X-rays, such as scanning X-rays. This allows the system to combine information from images acquired when the patient is lying down (e.g., lying down for a CT scan) and when the patient is in a loaded state (e.g., when a patient is standing during the standing X-ray). The system can automatically compare the loading state of the patient to the image using historical information, user input, or the like.

The system can identify abnormal loading states and images and notify the user that additional images may be required. In some embodiments, the system can compare the imaged anatomical features to predicted anatomical feature positions and then can send an alert to a user if the imaged anatomical elements are positioned at a threshold deviation.

The system can accurately predict and/or display sagittal and/or coronal balance of vertebral bodies, including non-treated vertebral bodies. Advantageously, the system can predict non-imaged regions of a patient's spine. For example, a patient may receive high-resolution CT scans of the lumbar region. The system can predict how lumbar procedures will alter the shape of other regions, including the thoracic and cervical regions. Even though the thoracic and cervical regions are not imaged using CT scans, the system can determine how to build a three-dimensional model suitable for simulating outcomes for the lumbar procedure. For example, the system can generate a spine model that includes the thoracic and cervical regions based on non-CT imaging of the entire spine. Example non-CT imaging can include, for example, X-rays. In some procedures, the system can acquire full spine images to generate a three-dimensional spine model. The full spine images can be taken from different perspectives. For example, the full spine images can be lateral images, anterior-posterior (AP) images, or other images. The system can combine the non-CT images with CT scans of the lumbar region to generate a full three-dimensional model. The system can perform 3D patient matching of vertebral bodies at various levels using the CT scans and non-CT scans. The non-CT scans can provide positional information for accurately positioning vertebral bodies. For example, the non-CT scans can be standing X-rays. The system can acquire loading information from the standing X-rays to position the vertebral bodies generated based on the CT scans, which may not show desired loading states.

A three-dimensional model can include planning information for receiving additional imaging input from users, such as surgical teams. The three-dimensional model can be used to generate three-dimensional plans. In some embodiments, a three-dimensional model can receive user input to provide for manual corrections. One or more predictive models can be applied to simulate compensatory mechanisms to the spinal corrections. The compensatory mechanisms can be, for example, lumbar corrections and how such corrections affect other regions of the spine. The predictive models can be generated using historical patient data. Example predictive models include, for example, (1) pelvic tilt compensatory response to lumbar corrections, (2) thoracic kyphosis compensatory response to lumbar corrections, and/or (3) cervical lordosis compensatory response to lumbar corrections. Other predictive models can be generated based on lumbar corrections. The system can allow a surgical team to plan for regional or global alignment with compensatory curves to provide more successful patient outcomes. The system can also be used to generate surgical plans that provide access to disc space. For example, the system can generate three-dimensional models for assisting in accessing disc space by positioning iliac crest and ribs with respect to the surgical paths.

FIG. 1 is a flow diagram illustrating a method 100 for mapping a 3D scan of at least a portion of a human anatomy to a 2D scan of at least the same portion of the human anatomy, according to an embodiment. At operation 102, an image processing module can obtain a volumetric 3D image of at least a spine of a patient. The volumetric 3D image can be obtained by using 3D imaging technology (e.g., CT scan or MRI) to scan or image a spine of a patient as the patient is in a horizontal or supine position. For example, the image processing module can obtain a high-quality Digital Imaging and Communications in Medicine (DICOM) image of the 3D anatomy. The volumetric 3D image may include images obtained along a plurality of planes that bisect the spine.

At operation 104, the image processing module can segment the 3D bony anatomy of the spine. A spine includes multiple segments or multiple anatomical elements that may start with C1, C2, C3 and end with L4, L5, sacrum, and coccyx. At operation 104, the image processing module can segment the lumbar vertebrae (L1 to L5) and sacrum (or S1) out of the volumetric 3D image and can perform image processing techniques to identify a set of planes or a region of the volumetric 3D image that corresponds to each of the L1 to L5 and sacrum segments or anatomical elements. Thus, for example, the image processing module can identify a first set of planes or a first region of the 3D volumetric image associated with L1, identify a second set of planes or a second region of the 3D volumetric image associated with L2, and so on until the image processing module can identify the set of planes or a region of the 3D volumetric image associated with the S1. Thus, segmenting the anatomy results in six 3D objects representing the L1, L2, L3, L4, L5 and S1 vertebrae, each still including their original position in the volumetric 3D image. In some embodiments, one or more other sections of the spine may be segmented (e.g., the thoracic spine, which includes vertebrae T1-T12) using the techniques described for operation 104.

At operation 106, the image processing module can identify landmarks on the segments or the anatomical elements of the lumbar vertebrae and sacrum from the 3D volumetric image. For example, the image processing module can identify an anterior of spinal endplate, a posterior of spinal endplate, a left lateral of spinal endplate, and a right lateral of spinal endplate for each of L1-L5 lumbar vertebra and the sacrum. A spinal endplate may be located on the superior and inferior aspects of the vertebra. The image processing module can identify additional landmarks for more accurate mapping. For example, the image processing module can identify an inferior aspect of spinous process, a superior aspect of spinous process, a left aspect of transverse process, and a right aspect of transverse process for each of the segments or the anatomical elements of the lumbar vertebrae. Each landmark identified by the image processing module can be associated with a 3D location (e.g., x, y, and z coordinates) of the landmark in 3D space.

In some embodiments, a graphical user interface (GUI) displayed by the image processing module can provide a user with an option to perform either a faster mapping or a more accurate mapping. If the image processing module receives an indication from the GUI that the faster mapping option has been selected, the image processing module can identify an anterior of spinal endplate, a posterior of spinal endplate, a left lateral of spinal endplate, and a right lateral of spinal endplate. If the image processing module receives an indication from the GUI that a more accurate mapping option has been selected, the image processing module can identify an anterior of spinal endplate, a posterior of spinal endplate, a left lateral of spinal endplate, a right lateral of spinal endplate, an inferior aspect of spinous process, a superior aspect of spinous process, a left aspect of transverse process, and a right aspect of transverse process for each of the segments of the lumbar vertebrae.

In some embodiments, the image processing module can use the landmarks on the segments or the anatomical elements of the lumbar vertebrae to measure the heights and angles between the individual vertebrae.

At operation 108, the image processing module can obtain a two-dimensional (2D) image comprising the lumbar vertebrae and sacrum. The 2D image of the lumbar vertebrae and sacrum belongs to the same patient whose spine-related information is obtained and analyzed at operations 102-106. The 2D image can be obtained by using 2D imaging technology (e.g., X-ray) to scan or image a spine of a patient as the patient is in a vertical or load-bearing position. In some embodiments, the image processing module can obtain different multi-dimensional images. The imaging processing module can analyze the images to determine, for example, whether sets of images include 2D data or 3D data, loading condition data, patient position data, etc. For example, the loading conditions can include whether anatomical features are under natural loading, when the patient stands or exercises, or in another load-bearing position. The subject position data can include, for example, whether the patient is lying down, whether the patient has a particular posture, or the like.

At operation 110, the image processing module can identify landmarks on the segments or the anatomical elements of the lumbar vertebrae and sacrum from the 2D image. At operation 110, the same landmarks can be identified on the 2D image as those identified in the 3D volumetric image. Thus, for example, the image processing module can obtain a sagittal view (e.g., mid-sagittal view) and a coronal view of the 2D planar imaging of the same anatomy as that obtained and analyzed in operations 102-106. From the sagittal and coronal views, the image processing module can identify an anterior of spinal endplate, a posterior of spinal endplate, a left lateral of spinal endplate, and a right lateral of spinal endplate for each of L1-L5 lumbar vertebra and the sacrum. The image processing module can identify on the sagittal and coronal views additional landmarks for more accurate mapping. For example, the image processing module can identify an inferior aspect of spinous process, a superior aspect of spinous process, a left aspect of transverse process, and a right aspect of transverse process for each of the segments or the anatomical elements of the lumbar vertebrae. Each landmark identified by the image processing module can be associated with a 2D location (e.g., two coordinates) of the landmark in 2D space. For example, for sagittal view, the landmark points can be associated with x and y coordinates since the image is captured in two dimensions, and for coronal view, the landmark points can include y and z coordinates since the image is captured in two dimensions. The coordinates in the two planes described above are relative coordinates that describe locations of the landmarks on coronal view plane and sagittal view plane.

At operation 112, the image processing operation can map 3D anatomy to 2D landmarks as further described in operations 114-122 that can be performed as part of performing operation 112. Operation 112 can include a process to map 3D anatomy to 2D landmarks, where 3D anatomy can be scaled, translated, and/or rotated by the image processing module to align the identified 3D landmarks (from operation 106) to the identified 2D landmarks (from operation 110). In some embodiments, at operation 112, the 3D anatomy can be loaded into 3D space so that the segmented vertebrae may appear in relation to each other as in the original 3D imaging. Operations 114 to 122 can be performed for each view including the lateral and AP views as further explained below. In a lateral view, the image processing module can map anterior and posterior landmarks from 3D and 2D images. In the AP view, the image processing module can map the left and right landmarks from 3D and 2D images.

At operation 114, the image processing module can create a first 2D plane (or 2D planar image) in a sagittal view from the 3D volumetric study approximately at the midline of the anatomy. Thus, at operation 114, the image processing module can create a first 2D planar image in a sagittal view from the 3D volumetric image, where the first 2D plane is the midplane, for example, a plane that bisects the sacrum along the sagittal view. A technical benefit for starting the process with sagittal view is that it can allow for analysis to determine whether the lumbar vertebrae are aligned or in a proper position.

At operation 116, the image processing module projects the 2D image of the sagittal view (e.g., 2D X-ray sagittal image) onto the first 2D plane (or first 2D planar image). The image processing module can scale and/or translate the first 2D plane so that the sacrum of the 2D sagittal planar image (or 2D image) overlaps the 3D version of the sacrum. In some embodiments, the image processing module can scale, rotate, and/or translate the 2D sagittal planar image (or 2D image) so that the sacrum of the first 2D plane overlaps the sacrum in the 2D sagittal planar image.

After the image processing module performs operations 114-116, the image processing module determines that the sacra from the 2D and 3D images are aligned and the image processing module can align one or more vertebrae of the lumbar vertebrae as explained in operations 118-122. A technical benefit of using sacrum to first align the 2D and 3D images is that the sacrum may not move much between loaded and unloaded positions so that aligning sacrum first can more efficiently use computational resources to align the lower region (e.g., lumbar) of the spine. In some embodiments, a lumbar vertebra can be used at operation 116 to align a 2D sagittal image onto the first 2D plane that bisects that lumbar vertebra.

At operation 118, the image processing module can align common landmarks from the 3D study (or 3D image) to the 2D study (or 2D image). For example, at operation 118, the image processing module can align a lumbar vertebra (e.g., L5 vertebra) and move the anterior and posterior landmarks of the lumbar vertebra (e.g., L5) in the 3D volumetric image to match the same landmarks on the sagittal planar image of the 2D image and adjust the other landmarks by the same amount as that used to move the anterior and posterior landmarks.

At operation 120, the image processing module can create a second 2D plane from the 3D volumetric image, where the second 2D plane extends across the sacrum along the coronal view. The image processing module projects a 2D coronal planar image (e.g., 2D X-ray coronal image) onto the second 2D plane. The image processing module can scale and/or translate the second 2D plane so that the sacrum of the 2D coronal planar image (or 2D image) overlaps the 3D version of the sacrum. In some embodiments, the image processing module can scale and/or translate the 2D coronal planar image (or 2D image) so that the sacrum of the second 2D plane overlaps the sacrum in the 2D coronal planar image.

At operation 122, the image processing module can move the anterior and posterior landmarks for the lumbar vertebra (e.g., L5) in the 3D volumetric image to match the same landmarks on the coronal planar image of the 2D image and adjust the other landmarks by the same amount as that used to move the anterior and posterior landmarks. A technical benefit of mapping the sacrum between the 2D plane of the 3D volumetric image and the 2D image is that it can more efficiently allow the mapping computations to use common coordinates between the coronal and sagittal planar images. At operations 118 and 122, when the image processing module moves/adjusts the landmarks for the lumbar vertebra from the 3D volumetric image to match the same landmarks on the sagittal and coronal planar images of the 2D images, the image processing module can obtain a 3D anatomical data of at least a portion of the spine in a loaded or load-bearing position.

As indicated by the arrow from operation 122 to operation 118, operations 118-122 can be repeated for one or more additional vertebrae (e.g., L4, L3, L2, and/or L1). In some embodiments, operations 118-122 are performed for all four remaining vertebrae. Once operations 118-122 are performed for one or more additional lumbar vertebrae, the 3D anatomy may match the positions of the vertebrae in the 2D planar images and an aligned 3D image data is created. The aligned 3D image data comprises a 3D representation of at least the sacrum and the lumbar vertebrae (e.g., L1 to L5) in a loaded or load-bearing position. In some embodiments, the image processing module can generate a corrected model of the spine based on the aligned 3D image data.

At operation 124, the image processing module can display the 3D study (or 3D image) reorganized by repositioning of the anatomy based on the 2D study (or 2D image). In some embodiments, at operation 124, the image processing module can display on the GUI the aligned 3D anatomy of the lumbar section and sacrum that are aligned with the corresponding anatomy in the 2D image data.

In some embodiments, after the image processing module maps the 3D anatomy to the 2D image, the image processing module can measure spinopelvic parameters (e.g., lumbar lordosis, pelvic tilt, sagittal vertical axis (SVA), Cobb angle, coronal offset, etc.) from reconstructed 3D image volumes that may be load bearing.

In some embodiments, the image processing module performs additional analysis on the 3D anatomy mapped to 2D to determine whether any feature of the spine can be corrected. For example, the image processing module can determine an amount by which 3D anatomy can be corrected and can send instructions to cause another computer to design implants corresponding to the determined amount to fit the corrected 3D anatomy.

The image processing module can use the modified or aligned 3D anatomy to generate a virtual model of the patient anatomy. The virtual model can be a multi-dimensional (e.g., two-dimensional or three-dimensional) virtual model and can include, for example, computer-aided design (CAD) data, material data, surface modeling, manufacturing data, or the like. The CAD data can include, for example, solid modeling data (e.g., part files, assembly files, libraries, part/object identifiers, etc.), model geometry, object representations, parametric data, object representations, topology data, surface data, assembly data, metadata, etc. The image processing module can also generate predicted post-operative or corrected anatomical models, surgical plans, virtual models of implants, implant design parameters, and instruments using the virtual model of the patient anatomy. Examples of the foregoing are described in U.S. application Ser. Nos. 16/048,167, 16/242,877, 16/207,116, 16/352,699, 16/383,215, 16/569,494, 16/699,447, 16/735,222, 16/987,113, 16/990,810, 17/085,564, 17/100,396, 17/342,329, 17/518,524, 17/531,417, 17/835,777, 17/851,487, 17/867,621, and 17/842,242, each of which is incorporated by reference herein in its entirety.

Figure 2:
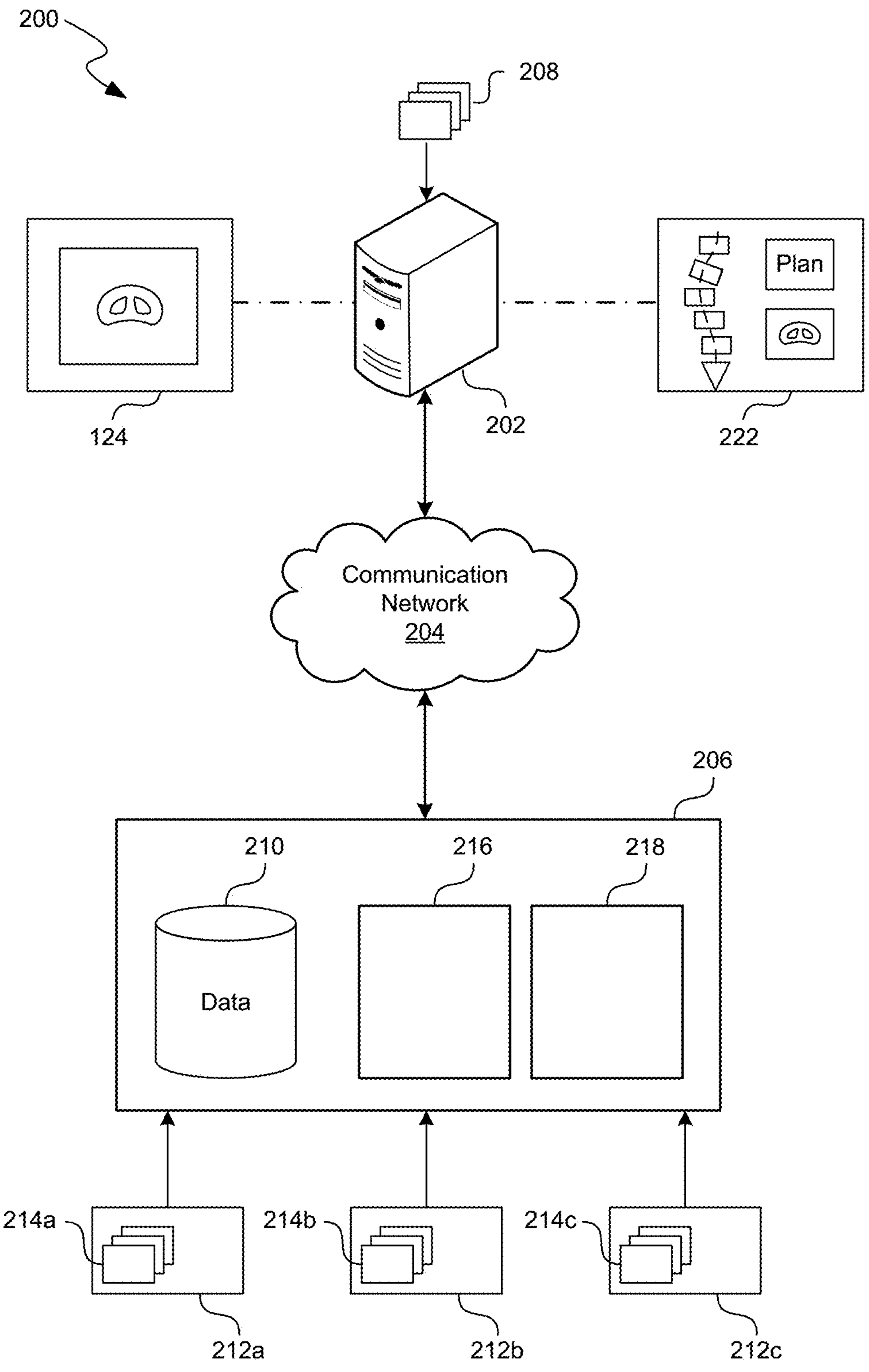
FIG. 2 is a network connection diagram illustrating a computing system for providing patient-specific medical care, according to an embodiment.

FIG. 2 is a network connection diagram illustrating a computing system 200 for providing patient-specific medical care, according to an embodiment. As described in further detail herein, the system 200 is configured to generate a medical treatment plan for a patient. In some embodiments, the system 200 is configured to generate a medical treatment plan for a patient suffering from an orthopedic or spinal disease or disorder, such as trauma (e.g., fractures), cancer, deformity, degeneration, pain (e.g., back pain, leg pain), irregular spinal curvature (e.g., scoliosis, lordosis, kyphosis), irregular spinal displacement (e.g., spondylolisthesis, lateral displacement, axial displacement), osteoarthritis, lumbar degenerative disc disease, cervical degenerative disc disease, lumbar spinal stenosis, cervical spinal stenosis, or a combination thereof. The medical treatment plan can include surgical information, surgical plans, technology recommendations (e.g., device and/or instrument recommendations), and/or medical device designs. For example, the medical treatment plan can include at least one treatment procedure (e.g., a surgical procedure or intervention) and/or at least one medical device (e.g., an implanted medical device (also referred to herein as an "implant" or "implanted device") or implant delivery instrument).

In some embodiments, the system 200 generates a medical treatment plan that is customized for a particular patient or group of patients, also referred to herein as a "patient-specific" or "personalized" treatment plan. The patient-specific treatment plan can include at least one patient-specific surgical procedure and/or at least one patient-specific medical device that are designed and/or optimized for the patient's particular characteristics (e.g., condition, anatomy, pathology, condition, medical history). For example, the patient-specific medical device can be designed and manufactured specifically for the particular patient, rather than being an off-the-shelf device. However, it shall be appreciated that a patient-specific treatment plan can also include aspects that are not customized for the particular patient. For example, a patient-specific or personalized surgical procedure can include one or more instructions, portions, steps, etc. that are non-patient-specific. Likewise, a patient-specific or personalized medical device can include one or more components that are non-patient-specific, and/or can be used with an instrument or tool that is non-patient-specific. Personalized implant designs can be used to manufacture or select patient-specific technologies, including medical devices, instruments, and/or surgical kits. For example, a personalized surgical kit can include one or more patient-specific devices, patient-specific instruments, non-patient-specific technology (e.g., standard instruments, devices, etc.), instructions for use, patient-specific treatment plan information, or a combination thereof.

The system 200 includes a client computing device 202, which can be a user device, such as a smart phone, mobile device, laptop, desktop, personal computer, tablet, phablet, or other such devices known in the art. As discussed further herein, the client computing device 202 can include one or more processors, and memory storing instructions executable by the one or more processors to perform the methods described herein. The client computing device 202 can be associated with a healthcare provider that is treating the patient. Although FIG. 2 illustrates a single client computing device 202, in alternative embodiments, the client computing device 202 can instead be implemented as a client computing system encompassing a plurality of computing devices, such that the operations described herein with respect to the client computing device 202 can instead be performed by the computing system and/or the plurality of computing devices.

The client computing device 202 is configured to receive a patient data set 208 associated with a patient to be treated. The patient data set 208 can include data representative of the patient's condition, anatomy, pathology, medical history, preferences, and/or any other information or parameters relevant to the patient. For example, the patient data set 208 can include medical history, surgical intervention data, treatment outcome data, progress data (e.g., physician notes), patient feedback (e.g., feedback acquired using quality of life questionnaires, surveys), clinical data, provider information (e.g., physician, hospital, surgical team), patient information (e.g., demographics, sex, age, height, weight, type of pathology, occupation, activity level, tissue information, health rating, comorbidities, health-related quality of life (HRQL)), vital signs, diagnostic results, medication information, allergies, image data (e.g., camera images, magnetic resonance imaging (MRI) images, ultrasound images, computerized axial tomography (CAT) scan images, positron emission tomography (PET) images, X-ray images), diagnostic equipment information (e.g., manufacturer, model number, specifications, user-selected settings/configurations, etc.), or the like. In some embodiments, the patient data set 208 includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine.

The client computing device 202 is operably connected via a communication network 204 to a server 206, thus allowing for data transfer between the client computing device 202 and the server 206. The communication network 204 may be a wired and/or a wireless network. The communication network 204, if wireless, may be implemented using communication techniques such as visible light communication (VLC), Worldwide Interoperability for Microwave Access (WiMAX), long-term evolution (LTE), wireless local area network (WLAN), infrared (IR) communication, Public Switched Telephone Network (PSTN), radio waves, and/or other communication techniques known in the art.

The server 206, which may also be referred to as a "treatment assistance network" or "prescriptive analytics network," can include one or more computing devices and/or systems. As discussed further herein, the server 206 can include one or more processors, and memory storing instructions executable by the one or more processors to perform the methods described herein. In some embodiments, the server 206 is implemented as a distributed "cloud" computing system or facility across any suitable combination of hardware and/or virtual computing resources.

The client computing device 202 and the server 206 can individually or collectively perform the various methods described herein for providing patient-specific medical care. For example, some or all of the steps of the methods described herein can be performed by the client computing device 202 alone, the server 206 alone, or a combination of the client computing device 202 and the server 206. Thus, although certain operations are described herein with respect to the server 206, it can be appreciated that these operations can also be performed by the client computing device 202, and vice versa. For example, the client computing device 202 and/or the server 206 may include processor(s) that can be configured to execute operations described for the image processing module above.

The server 206 includes at least one database 210 configured to store reference data useful for the treatment planning methods described herein. The reference data can include historical and/or clinical data from the same or other patients, data collected from prior surgeries and/or other treatments of patients by the same or other healthcare providers, data relating to medical device designs, data collected from study groups or research groups, data from practice databases, data from academic institutions, data from implant manufacturers or other medical device manufacturers, data from imaging studies, data from simulations, data from clinical trials, demographic data, treatment data, outcome data, mortality rates, or the like.

In some embodiments, the database 210 includes a plurality of reference patient data sets, each reference patient data set associated with a corresponding reference patient. For example, the reference patient can be a patient that previously received treatment or is currently receiving treatment. Each reference patient data set can include data representative of the corresponding reference patient's condition, anatomy, pathology, medical history, disease progression, preferences, and/or any other information or parameters relevant to the reference patient, such as any of the data described herein with respect to the patient data set 208. In some embodiments, the reference patient data set includes pre-operative data, intra-operative data, and/or post-operative data. For example, a reference patient data set can include data representing one or more of patient ID, age, gender, BMI, lumbar lordosis, Cobb angle(s), pelvic incidence, disc height, segment flexibility, bone quality, rotational displacement, and/or treatment level of the spine. As another example, a reference patient data set can include treatment data regarding at least one treatment procedure performed on the reference patient, such as descriptions of surgical procedures or interventions (e.g., surgical approaches, bony resections, surgical maneuvers, corrective maneuvers, placement of implants or other devices). In some embodiments, the treatment data includes medical device design data for at least one medical device used to treat the reference patient, such as physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties). In yet another example, a reference patient data set can include outcome data representing an outcome of the treatment of the reference patient, such as corrected anatomical metrics, presence of fusion, HRQL, activity level, return to work, complications, recovery times, efficacy, mortality, and/or follow-up surgeries.

In some embodiments, the server 206 receives at least some of the reference patient data sets from a plurality of healthcare provider computing systems (e.g., systems 212*a*-212*c*, collectively 212). The server 206 can be connected to the healthcare provider computing systems 212 via one or more communication networks (not shown). Each healthcare provider computing system 212 can be associated with a corresponding healthcare provider (e.g., physician, surgeon, medical clinic, hospital, healthcare network, etc.). Each healthcare provider computing system 212 can include at least one reference patient data set (e.g., reference patient data sets 214*a*-214*c*, collectively 214) associated with reference patients treated by the corresponding healthcare provider. The reference patient data sets 214 can include, for example, electronic medical records, electronic health records, biomedical data sets, etc. The reference patient data sets 214 can be received by the server 206 from the healthcare provider computing systems 212 and can be reformatted into different formats for storage in the database 210. Optionally, the reference patient data sets 214 can be processed (e.g., cleaned) to ensure that the represented patient parameters are likely to be useful in the treatment planning methods described herein.

As described in further detail herein, the server 206 can be configured with one or more algorithms that generate patient-specific treatment plan data (e.g., treatment procedures, medical devices) based on the reference data. In some embodiments, the patient-specific data is generated based on correlations between the patient data set 208 and the reference data. Optionally, the server 206 can predict outcomes, including recovery times, efficacy based on clinical end points, likelihood of success, predicted mortality, predicted related follow-up surgeries, or the like. In some embodiments, the server 206 can continuously or periodically analyze patient data (including patient data obtained during the patient stay) to determine near real-time or real-time risk scores, mortality prediction, etc.

In some embodiments, the server 206 includes one or more modules for performing one or more steps of the patient-specific treatment planning methods described herein. For example, in the depicted embodiment, the server 206 includes a data analysis module 216 and a treatment planning module 218. In alternative embodiments, one or more of these modules may be combined with each other, or may be omitted. Thus, although certain operations are described herein with respect to a particular module or modules, this is not intended to be limiting, and such operations can be performed by a different module or modules in alternative embodiments.

The data analysis module 216 is configured with one or more algorithms for identifying a subset of reference data from the database 210 that is likely to be useful in developing a patient-specific treatment plan. For example, the data analysis module 216 can compare patient-specific data (e.g., the patient data set 208 received from the client computing device 202) to the reference data from the database 210 (e.g., the reference patient data sets) to identify similar data (e.g., one or more similar patient data sets in the reference patient data sets). The comparison can be based on one or more parameters, such as age, gender, BMI, lumbar lordosis, pelvic incidence, and/or treatment levels. The parameter(s) can be used to calculate a similarity score for each reference patient. The similarity score can represent a statistical correlation between the patient data set 208 and the reference patient data set. Accordingly, similar patients can be identified based on whether the similarity score is above, below, or at a specified threshold value. For example, as described in greater detail below, the comparison can be performed by assigning values to each parameter and determining the aggregate difference between the subject patient and each reference patient. Reference patients whose aggregate difference is below a threshold can be considered to be similar patients.

The data analysis module 216 can further be configured with one or more algorithms to select a subset of the reference patient data sets, e.g., based on similarity to the patient data set 208 and/or treatment outcome of the corresponding reference patient. For example, the data analysis module 216 can identify one or more similar patient data sets in the reference patient data sets, and then select a subset of the similar patient data sets based on whether the similar patient data set includes data indicative of a favorable or desired treatment outcome. The outcome data can include data representing one or more outcome parameters, such as corrected anatomical metrics, presence of fusion, HRQL, activity level, complications, recovery times, efficacy, mortality, or follow-up surgeries. As described in further detail below, in some embodiments, the data analysis module 216 calculates an outcome score by assigning values to each outcome parameter. A patient can be considered to have a favorable outcome if the outcome score is above, below, or at a specified threshold value.

In some embodiments, the data analysis module 216 selects a subset of the reference patient data sets based at least in part on user input (e.g., from a clinician, surgeon, physician, healthcare provider). For example, the user input can be used in identifying similar patient data sets. In some embodiments, weighting of similarity and/or outcome parameters can be selected by a healthcare provider or physician to adjust the similarity and/or outcome score based on clinician input. In further embodiments, the healthcare provider or physician can select the set of similarity and/or outcome parameters (or define new similarity and/or outcome parameters) used to generate the similarity and/or outcome score, respectively.

In some embodiments, the data analysis module 216 includes one or more algorithms used to select a set or subset of the reference patient data sets based on criteria other than patient parameters. For example, the one or more algorithms can be used to select the subset based on healthcare provider parameters (e.g., based on healthcare provider ranking/scores such as hospital/physician expertise, number of procedures performed, hospital ranking, etc.) and/or healthcare resource parameters (e.g., diagnostic equipment, facilities, surgical equipment such as surgical robots), or other non-patient-related information that can be used to predict outcomes and risk profiles for procedures for the present healthcare provider. For example, reference patient data sets with images captured from similar diagnostic equipment can be aggregated to reduce or limit irregularities due to variation between diagnostic equipment. Additionally, patient-specific treatment plans can be developed for a particular healthcare provider using data from similar healthcare providers (e.g., healthcare providers with traditionally similar outcomes, physician expertise, surgical teams, etc.). In some embodiments, reference healthcare provider data sets, hospital data sets, physician data sets, surgical team data sets, post-treatment data sets, and other data sets can be utilized. By way of example, a patient-specific treatment plan to perform a battlefield surgery can be based on reference patient data from similar battlefield surgeries and/or data sets associated with battlefield surgeries. In another example, the patient-specific treatment plan can be generated based on available robotic surgical systems. The reference patient data sets can be selected based on patients that have been operated on using comparable robotic surgical systems under similar conditions (e.g., size and capabilities of surgical teams, hospital resources, etc.).

The treatment planning module 218 is configured with one or more algorithms to generate at least one treatment plan (e.g., pre-operative plans, surgical plans, post-operative plans, etc.) based on the output from the data analysis module 216. In some embodiments, the treatment planning module 218 is configured to develop and/or implement at least one predictive model for generating the patient-specific treatment plan, also known as a "prescriptive model." The predictive model(s) can be developed using clinical knowledge, statistics, machine learning, artificial intelligence (AI), neural networks, or the like. In some embodiments, the output from the data analysis module 216 is analyzed (e.g., using statistics, machine learning, neural networks, AI) to identify correlations between data sets, patient parameters, healthcare provider parameters, healthcare resource parameters, treatment procedures, medical device designs, and/or treatment outcomes. These correlations can be used to develop at least one predictive model that predicts the likelihood that a treatment plan will produce a favorable outcome for the particular patient. The predictive model(s) can be validated, e.g., by inputting data into the model(s) and comparing the output of the model to the expected output.

In some embodiments, the treatment planning module 218 is configured to generate the treatment plan based on previous treatment data from reference patients. For example, the treatment planning module 218 can receive a selected subset of reference patient data sets and/or similar patient data sets from the data analysis module 216, and determine or identify treatment data from the selected subset. The treatment data can include, for example, treatment procedure data (e.g., surgical procedure or intervention data) and/or medical device design data (e.g., implant design data) that are associated with favorable or desired treatment outcomes for the corresponding patient. The treatment planning module 218 can analyze the treatment procedure data and/or medical device design data to determine an optimal treatment protocol for the patient to be treated. For example, the treatment procedures and/or medical device designs can be assigned values and aggregated to produce a treatment score. The patient-specific treatment plan can be determined by selecting treatment plan(s) based on the score (e.g., higher or highest score; lower or lowest score; score that is above, below, or at a specified threshold value). The personalized patient-specific treatment plan can be based on, at least in part, the patient-specific technologies or patient-specific selected technology. In some embodiments, the treatment planning module 218 is configured to generate the treatment plan (e.g., manufacture a medical device design data) based on spinopelvic parameters measured by the image processing module from the aligned 3D image data of the spine (e.g., lumbar vertebrae and sacrum) that is aligned with the corresponding anatomical features from the 2D image data.

Alternatively or in combination, the treatment planning module 218 can generate the treatment plan based on correlations between data sets. For example, the treatment planning module 218 can correlate treatment procedure data and/or medical device design data from similar patients with favorable outcomes (e.g., as identified by the data analysis module 216). Correlation analysis can include transforming correlation coefficient values to values or scores. The values/scores can be aggregated, filtered, or otherwise analyzed to determine one or more statistical significances. These correlations can be used to determine treatment procedure(s) and/or medical device design(s) that are optimal or likely to produce a favorable outcome for the patient to be treated.

Alternatively or in combination, the treatment planning module 218 can generate the treatment plan using one or more AI techniques. AI techniques can be used to develop computing systems capable of simulating aspects of human intelligence, e.g., learning, reasoning, planning, problem solving, decision making, etc. AI techniques can include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems.

In some embodiments, the treatment planning module 218 generates the treatment plan using one or more trained machine learning models. Various types of machine learning models, algorithms, and techniques are suitable for use with the present technology. In some embodiments, the machine learning model is initially trained on a training data set, which is a set of examples used to fit the parameters (e.g., weights of connections between "neurons" in artificial neural networks) of the model. For example, the training data set can include any of the reference data stored in the database 210, such as a plurality of reference patient data sets or a selected subset thereof (e.g., a plurality of similar patient data sets).

In some embodiments, the machine learning model (e.g., a neural network or a naïve Bayes classifier) may be trained on the training data set using a supervised learning method (e.g., gradient descent or stochastic gradient descent). The training data set can include pairs of generated "input vectors" with the associated corresponding "answer vector" (commonly denoted as the target). The current model is run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some embodiments, the error of the validation data set error can fluctuate during training, such that ad hoc rules may be used to decide when overfitting has truly begun. Finally, a test data set can be used to provide an unbiased evaluation of a final model fit on the training data set.

To generate a treatment plan, the patient data set 208 can be input into the trained machine learning model(s). Additional data, such as the selected subset of reference patient data sets and/or similar patient data sets, and/or treatment data from the selected subset, can also be input into the trained machine learning model(s). The trained machine learning model(s) can then calculate whether various candidate treatment procedures and/or medical device designs are likely to produce a favorable outcome for the patient. Based on these calculations, the trained machine learning model(s) can select at least one treatment plan for the patient. In embodiments where multiple trained machine learning models are used, the models can be run sequentially or concurrently to compare outcomes and can be periodically updated using training data sets. The treatment planning module 218 can use one or more of the machine learning models based on the model's predicted accuracy score.

The patient-specific treatment plan generated by the treatment planning module 218 can include at least one patient-specific treatment procedure (e.g., a surgical procedure or intervention) and/or at least one patient-specific medical device (e.g., an implant or implant delivery instrument). A patient-specific treatment plan can include an entire surgical procedure or portions thereof. Additionally, one or more patient-specific medical devices can be specifically selected or designed for the corresponding surgical procedure, thus allowing for the various components of the patient-specific technology to be used in combination to treat the patient.

In some embodiments, the patient-specific treatment procedure includes an orthopedic surgery procedure, such as spinal surgery, hip surgery, knee surgery, jaw surgery, hand surgery, shoulder surgery, elbow surgery, total joint reconstruction (arthroplasty), skull reconstruction, foot surgery, or ankle surgery. Spinal surgery can include spinal fusion surgery, such as posterior lumbar interbody fusion (PLIF), anterior lumbar interbody fusion (ALIF), transverse or transforaminal lumbar interbody fusion (TLIF), lateral lumbar interbody fusion (LLIF), direct lateral lumbar interbody fusion (DLIF), or extreme lateral lumbar interbody fusion (XLIF). In some embodiments, the patient-specific treatment procedure includes descriptions of and/or instructions for performing one or more aspects of a patient-specific surgical procedure. For example, the patient-specific surgical procedure can include one or more of a surgical approach, a corrective maneuver, a bony resection, or implant placement.

In some embodiments, the patient-specific medical device design includes a design for an orthopedic implant and/or a design for an instrument for delivering an orthopedic implant. Examples of such implants include, but are not limited to, screws (e.g., bone screws, spinal screws, pedicle screws, facet screws), interbody implant devices (e.g., intervertebral implants), cages, plates, rods, disks, fusion devices, spacers, rods, expandable devices, stents, brackets, ties, scaffolds, fixation devices, anchors, nuts, bolts, rivets, connectors, tethers, fasteners, joint replacements, hip implants, or the like. Examples of instruments include, but are not limited to, screw guides, cannulas, ports, catheters, insertion tools, or the like.

A patient-specific medical device design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of a corresponding medical device. For example, a design for an orthopedic implant can include implant shape, size, material, and/or effective stiffness (e.g., lattice density, number of struts, location of struts, etc.). In some embodiments, the generated patient-specific medical device design is a design for an entire device. Alternatively, the generated design can be for one or more components of a device, rather than the entire device.

In some embodiments, the design is for one or more patient-specific device components that can be used with standard, off-the-shelf components. For example, in a spinal surgery, a pedicle screw kit can include both standard components and patient-specific customized components. In some embodiments, the generated design is for a patient-specific medical device that can be used with a standard, off-the-shelf delivery instrument. For example, the implants (e.g., screws, screw holders, rods) can be designed and manufactured for the patient, while the instruments for delivering the implants can be standard instruments. This approach allows the components that are implanted to be designed and manufactured based on the patient's anatomy and/or the surgeon's preferences to enhance treatment. The patient-specific devices described herein are expected to improve delivery into the patient's body, placement at the treatment site, and/or interaction with the patient's anatomy.

In embodiments where the patient-specific treatment plan includes a surgical procedure to implant a medical device, the treatment planning module 218 can also store various types of implant surgery information, such as implant parameters (e.g., types, dimensions), availability of implants, aspects of a pre-operative plan (e.g., initial implant configuration, detection and measurement of the patient's anatomy, etc.), FDA requirements for implants (e.g., specific implant parameters and/or characteristics for compliance with FDA regulations), or the like. In some embodiments, the treatment planning module 218 can convert the implant surgery information into formats usable for machine learning-based models and algorithms. For example, the implant surgery information can be tagged with particular identifiers for formulas or can be converted into numerical representations suitable for supplying to the trained machine learning model(s). The treatment planning module 218 can also store information regarding the patient's anatomy, such as two- or three-dimensional images or models of the anatomy, and/or information regarding the biology, geometry, and/or mechanical properties of the anatomy. The anatomy information can be used to inform implant design and/or placement.

The treatment plan(s) generated by the treatment planning module 218 can be transmitted via the communication network 204 to the client computing device 202 for output to a user (e.g., clinician, surgeon, healthcare provider, patient). In some embodiments, the client computing device 202 includes or is operably coupled to a display 222 for outputting the treatment plan(s). The display 222 can include a GUI for visually depicting various aspects of the treatment plan(s). For example, the display 222 can show various aspects of a surgical procedure to be performed on the patient, such as the surgical approach, treatment levels, corrective maneuvers, tissue resection, and/or implant placement. To facilitate visualization, a virtual model of the surgical procedure can be displayed. As another example, the display 222 can show a design for a medical device to be implanted in the patient, such as a two- or three-dimensional model of the device design. The display 222 can also show patient information, such as two- or three-dimensional images or models of the patient's anatomy where the surgical procedure is to be performed and/or where the device is to be implanted. The client computing device 202 can further include one or more user input devices (not shown) allowing the user to modify, select, approve, and/or reject the displayed treatment plan(s).

In some embodiments, the medical device design(s) generated by the treatment planning module 218 can be transmitted from the client computing device 202 and/or the server 206 to a manufacturing system 224 for manufacturing a corresponding medical device. The manufacturing system 224 can be located on site or off site. On-site manufacturing can reduce the number of sessions with a patient and/or the wait time required before performing the surgery, whereas off-site manufacturing can be useful for making the complex devices, as off-site manufacturing facilities can have specialized manufacturing equipment. In some embodiments, more complicated device components can be manufactured off site, while simpler device components can be manufactured on site.

Various types of manufacturing systems are suitable for use in accordance with the embodiments herein. For example, the manufacturing system 224 can be configured for additive manufacturing, such as three-dimensional (3D) printing, stereolithography (SLA), digital light processing (DLP), fused deposition modeling (FDM), selective laser sintering (SLS), selective laser melting (SLM), selective heat sintering (SHM), electronic beam melting (EBM), laminated object manufacturing (LOM), powder bed printing (PP), thermoplastic printing, direct material deposition (DMD), inkjet photo resin printing, or like technologies, or a combination thereof. Alternatively or in combination, the manufacturing system 224 can be configured for subtractive (traditional) manufacturing, such as CNC machining, electrical discharge machining (EDM), grinding, laser cutting, water jet machining, manual machining (e.g., milling, lathe/turning), or like technologies, or combinations thereof. The manufacturing system 224 can manufacture one or more patient-specific medical devices based on fabrication instructions or data (e.g., CAD data, 3D data, digital blueprints, stereolithography data, or other data suitable for the various manufacturing technologies described herein). Different components of the system 200 can generate at least a portion of the manufacturing data used by the manufacturing system 224. The manufacturing data can include, without limitation, fabrication instructions (e.g., programs executable by additive manufacturing equipment, subtractive manufacturing equipment, etc.), 3D data, CAD data (e.g., CAD files), computer-aided manufacturing (CAM) data (e.g., CAM files), path data (e.g., print head paths, tool paths, etc.), material data, tolerance data, surface finish data (e.g., surface roughness data), regulatory data (e.g., FDA requirements, reimbursement data, etc.), or the like. The manufacturing system 224 can analyze the manufacturability of the implant design based on the received manufacturing data. The implant design can be finalized by altering geometries, surfaces, etc. and then generating manufacturing instructions. In some embodiments, the server 206 generates at least a portion of the manufacturing data, which is transmitted to the manufacturing system 224.

The manufacturing system 224 can generate CAM data, print data (e.g., powder bed print data, thermoplastic print data, photo resin data, etc.), or the like, and can include additive manufacturing equipment, subtractive manufacturing equipment, thermal processing equipment, or the like. The additive manufacturing equipment can be 3D printers, stereolithography devices, digital light processing devices, fused deposition modeling devices, selective laser sintering devices, selective laser melting devices, electronic beam melting devices, laminated object manufacturing devices, powder bed printers, thermoplastic printers, direct material deposition devices, inkjet photo resin printers, or like technologies. The subtractive manufacturing equipment can be CNC machines, electrical discharge machines, grinders, laser cutters, water jet machines, manual machines (e.g., milling machines, lathes, etc.), or like technologies. Both additive and subtractive techniques can be used to produce implants with complex geometries, surface finishes, material properties, etc. The generated fabrication instructions can be configured to cause the manufacturing system 224 to manufacture the patient-specific orthopedic implant that matches or is therapeutically the same as the patient-specific design. In some embodiments, the patient-specific medical device can include features, materials, and designs shared across designs to simplify manufacturing. For example, deployable patient-specific medical devices for different patients can have similar internal deployment mechanisms but have different deployed configurations. In some embodiments, the components of the patient-specific medical devices are selected from a set of available pre-fabricated components and the selected pre-fabricated components can be modified based on the fabrication instructions or data.

The treatment plans described herein can be performed by a surgeon, a surgical robot, or a combination thereof, thus allowing for treatment flexibility. In some embodiments, the surgical procedure can be performed entirely by a surgeon, entirely by a surgical robot, or a combination thereof. For example, one step of a surgical procedure can be manually performed by a surgeon and another step of the procedure can be performed by a surgical robot. In some embodiments, the treatment planning module 218 generates control instructions configured to cause a surgical robot (e.g., robotic surgery systems, navigation systems, etc.) to partially or fully perform a surgical procedure. The control instructions can be transmitted to the robotic apparatus by the client computing device 202 and/or the server 206.

Following the treatment of the patient in accordance with the treatment plan, treatment progress can be monitored over one or more time periods to update the data analysis module 216 and/or the treatment planning module 218. Post-treatment data can be added to the reference data stored in the database 210. The post-treatment data can be used to train machine learning models for developing patient-specific treatment plans, patient-specific medical devices, or combinations thereof.

It shall be appreciated that the components of the system 200 can be configured in many different ways. For example, in alternative embodiments, the database 210, the data analysis module 216, and/or the treatment planning module 218 can be components of the client computing device 202, rather than the server 206. As another example, the database 210, the data analysis module 216, and/or the treatment planning module 218 can be located across a plurality of different servers, computing systems, or other types of cloud-computing resources, rather than at a single server 206 or client computing device 202.

Additionally, in some embodiments, the system 200 can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

Figure 3:
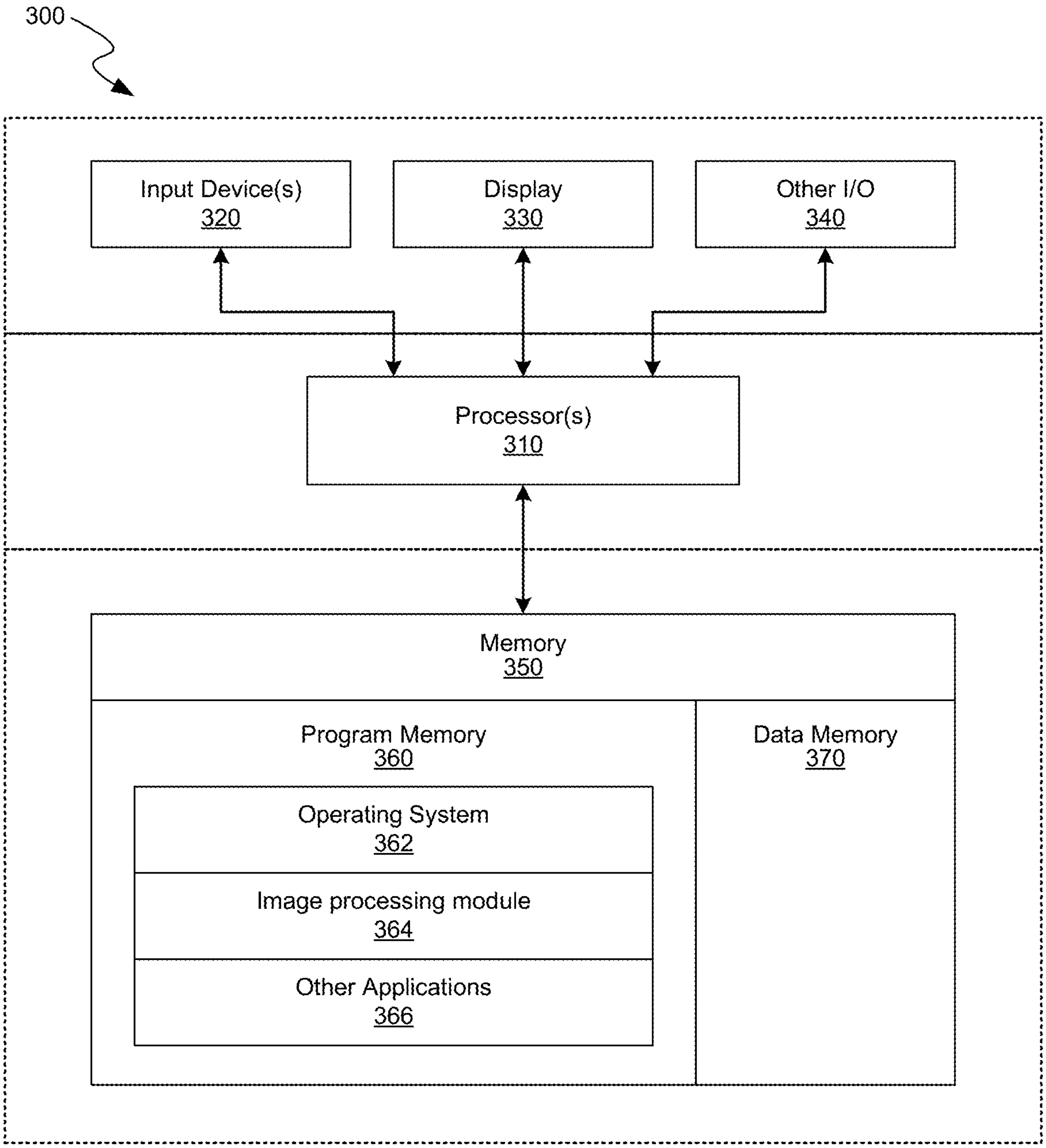
FIG. 3 illustrates a computing device suitable for use in connection with the system of FIG. 2, according to an embodiment.

FIG. 3 illustrates a computing device 300 suitable for use in connection with the system 200 of FIG. 2, according to an embodiment. The computing device 300 can be incorporated in various components of the system 200 of FIG. 2, such as the client computing device 202 or the server 206. The computing device 300 includes one or more processors 310 (e.g., CPU(s), GPU(s), HPU(s), etc.). The processor(s) 310 can be a single processing unit or multiple processing units in a device or distributed across multiple devices. The processor(s) 310 can be coupled to other hardware devices, for example, with the use of a bus, such as a PCI bus or SCSI bus. The processor(s) 310 can be configured to execute one more computer-readable program instructions, such as program instructions to carry out any of the methods described herein.

The computing device 300 can include one or more input devices 320 that provide input to the processor(s) 310, e.g., to notify it of actions from a user of the computing device 300. The actions can be mediated by a hardware controller that interprets the signals received from the input device and communicates the information to the processor(s) 310 using a communication protocol. Input device(s) 320 can include, for example, a mouse, a keyboard, a touchscreen, an infrared sensor, a touchpad, a wearable input device, a camera- or image-based input device, a microphone, or other user input devices.

The computing device 300 can include a display 330 used to display various types of output, such as text, models, virtual procedures, surgical plans, implants, graphics, and/or images (e.g., images with voxels indicating radiodensity units or Hounsfield units representing the density of the tissue at a location). In some embodiments, the display 330 provides graphical and textual visual feedback to a user. The processor(s) 310 can communicate with the display 330 via a hardware controller for devices. In some embodiments, the display 330 includes the input device(s) 320 as part of the display 330, such as when the input device(s) 320 include a touchscreen or are equipped with an eye direction monitoring system. In alternative embodiments, the display 330 is separate from the input device(s) 320. Examples of display devices include an LCD display screen, an LED display screen, a projected, holographic, or augmented reality display (e.g., a heads-up display device or a head-mounted device), and so on.

Optionally, other input/output (I/O) devices 340 can also be coupled to the processor(s) 310, such as a network card, video card, audio card, USB, firewire or other external device, camera, printer, speakers, CD-ROM drive, DVD drive, disk drive, or Blu-Ray device. Other I/O devices 340 can also include input ports for information from directly connected medical equipment such as imaging apparatuses, including MRI machines, X-ray machines, CT machines, etc. Other I/O devices 340 can further include input ports for receiving data from these types of machines from other sources, such as across a network or from previously captured data, for example, stored in a database.

In some embodiments, the computing device 300 also includes a communication device (not shown) capable of wireless or wire-based communication with a network node. The communication device can communicate with another device or a server through a network using, for example, TCP/IP protocols. The computing device 300 can utilize the communication device to distribute operations across multiple network devices, including imaging equipment, manufacturing equipment, etc.

The computing device 300 can include memory 350, which can be in a single device or distributed across multiple devices. Memory 350 includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. In some embodiments, memory 350 is a non-transitory computer-readable storage medium that stores, for example, programs, software, data, or the like. In some embodiments, memory 350 can include program memory 360 that stores programs and software, such as an operating system 362, one or more image processing modules 364, and other application programs 366. The image processing module 364 can include one or more modules configured to perform the various methods described herein (e.g., the data analysis module 216 and/or the treatment planning module 218 described with respect to FIG. 2). Memory 350 can also include data memory 370 that can include, e.g., reference data, configuration data, settings, user options or preferences, etc., which can be provided to the program memory 360 or any other element of the computing device 300.

Figure 4A:
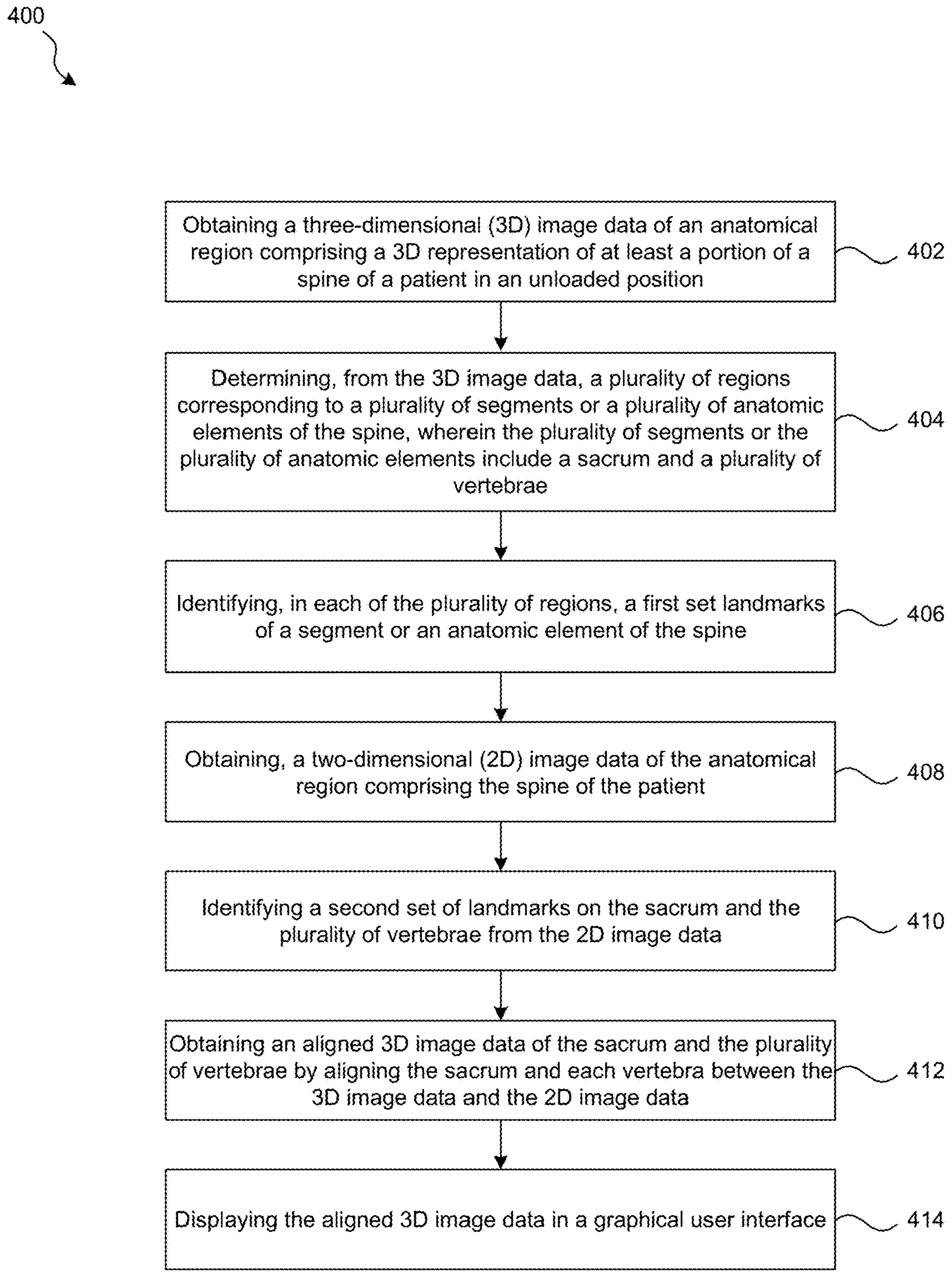
FIG. 4A shows an example flowchart of operations to map a portion of a human anatomy in a 3D image study to a corresponding portion of the same human anatomy in a 2D image.

FIG. 4A shows an example flowchart 400 of operations to map a portion of a human anatomy in a 3D image study to a corresponding portion of the same human anatomy in a 2D image. Operation 402 includes obtaining a three-dimensional (3D) image data of an anatomical region comprising a 3D representation of at least a portion of a spine of a patient in an unloaded position. Operation 404 includes determining, from the 3D image data, a plurality of regions corresponding to a plurality of segments or a plurality of anatomical elements of the spine, wherein the plurality of segments or the plurality of anatomical elements include a sacrum and a plurality of vertebrae. Operation 406 includes identifying, in each of the plurality of regions, a first set of landmarks of a segment or an anatomical element of the spine. Operation 408 includes obtaining a two-dimensional (2D) image data of the anatomical region comprising the spine of the patient. Operation 410 includes identifying a second set of landmarks on the sacrum and the plurality of vertebrae from the 2D image data; the landmarks should be common between the 2D and 3D image studies. Operation 412 includes obtaining an aligned 3D image data of the sacrum and the plurality of vertebrae by aligning the sacrum and each vertebra between the 3D image data and the 2D image data, where the aligned 3D image data includes a 3D representation of at least the sacrum and the plurality of lumbar vertebrae in a loaded or load-bearing position, and where the aligning each lumbar vertebra is performed based on the first set of landmarks and the second set of landmarks. Operation 414 includes displaying the aligned 3D image data in a graphical user interface (GUI). The operations described in flowchart 400 can be performed by the image processing module as described in this patent document.

In some embodiments, in response to the segment or the anatomical element being a lumbar vertebra, the identifying the first set of landmarks of the segment or the anatomical element of the spine includes identifying a first set of information that includes identifying: an inferior aspect of spinous process of the lumbar vertebrae, a superior aspect of spinous process of the lumbar vertebrae, a left aspect of transverse process of the lumbar vertebrae, and a right aspect of transverse process of the lumbar vertebrae. In some embodiments, the first set of information is identified in response to receiving from the GUI an indication of a selection of a fast mapping option. In some embodiments, the identifying the first set of landmarks of the segment or the anatomical element of the spine includes identifying a second set of information that includes identifying: an anterior landmark of spinal or vertebral endplate, a posterior landmark of spinal or vertebral endplate, a left lateral landmark of spinal or vertebral endplate, and a right lateral landmark of spinal or vertebral endplate.

In some embodiments, the first set of information and the second set of information is identified in response to receiving from the GUI an indication of a selection of an accurate mapping option. In some embodiments, each of the first set of landmarks of the segment or the anatomical element of the spine is associated with a 3D location in a 3D space of the 3D image data. In some embodiments, the second set of landmarks on the sacrum and the plurality of lumbar vertebrae are identified from the 2D image data comprising a sagittal view and a coronal view of the anatomical region. In some embodiments, the identifying the second set of landmarks of the spine includes identifying any one or more of: an inferior aspect of spinous process of the lumbar vertebrae, a superior aspect of spinous process of the lumbar vertebrae, a left aspect of transverse process of the lumbar vertebrae, a right aspect of transverse process of the lumbar vertebrae, an anterior landmark of spinal or vertebral endplate, a posterior landmark of spinal or vertebral endplate, a left lateral landmark of spinal or vertebral endplate, and a right lateral landmark of spinal or vertebral endplate.

In some embodiments, each of the first and second of landmarks of the spine is associated with a 2D location in a 2D space of the 2D image data. In some embodiments, the aligning the sacrum between the 3D image data and the 2D image data is performed by: creating, from the 3D image data, a first image data along a sagittal view that bisects the sacrum; projecting a second image data along the sagittal view from the 2D image data onto the first image data, wherein the second image data comprises the sacrum; and causing the sacrum from the first image data to overlap with the sacrum of the second image data by scaling, rotating, and/or translating the first image data.

In some embodiments, the aligning each lumbar vertebra between the 3D image data and the 2D image data is performed in response to the aligning the sacrum by: performing a first aligning operation of a lumbar vertebra by moving an anterior landmark and a posterior landmark of the lumbar vertebra in the 3D image data to match the same landmarks on the second image data from the 2D image data, wherein the second image data comprises the lumbar vertebra; creating, from the 3D image data, a third image data along a coronal view that extends across the sacrum; projecting a fourth image data along the coronal view from the 2D image data onto the third image data, wherein the fourth image data comprises the sacrum; causing the sacrum from the third image data to overlap with the sacrum of the second image data by scaling or translating the first image data; and performing a second aligning operation of the lumbar vertebra by moving the anterior landmark and the posterior landmark for the lumbar vertebra to match the same landmarks on the fourth image data from the 2D image, wherein the fourth image data comprises the lumbar vertebra.

In some embodiments, the method further comprises adjusting one or more other landmarks of the lumbar vertebra by a same amount as that used to move the anterior landmark and the posterior landmark of the lumbar vertebra in the 3D image data for the first aligning operation; and adjusting one or more other landmarks of the lumbar vertebra by a same amount as that used to move the anterior landmark and the posterior landmark of the lumbar vertebra in the 3D image data for the second aligning operation. In some embodiments, positions of the plurality of segments or the plurality of anatomical elements of the spine in the 3D image data are maintained as the plurality of regions are determined. In some embodiments, the 3D image data is obtained from a computer tomography (CT) scan or a magnetic resonance imaging (MRI) scan. In some embodiments, the method further comprises generating a design for a medical implant based on spinopelvic parameters measured from the aligned 3D image data; and causing a medical implant to be manufactured by sending the design for the medical implant to a manufacturing device.

Figure 4B:
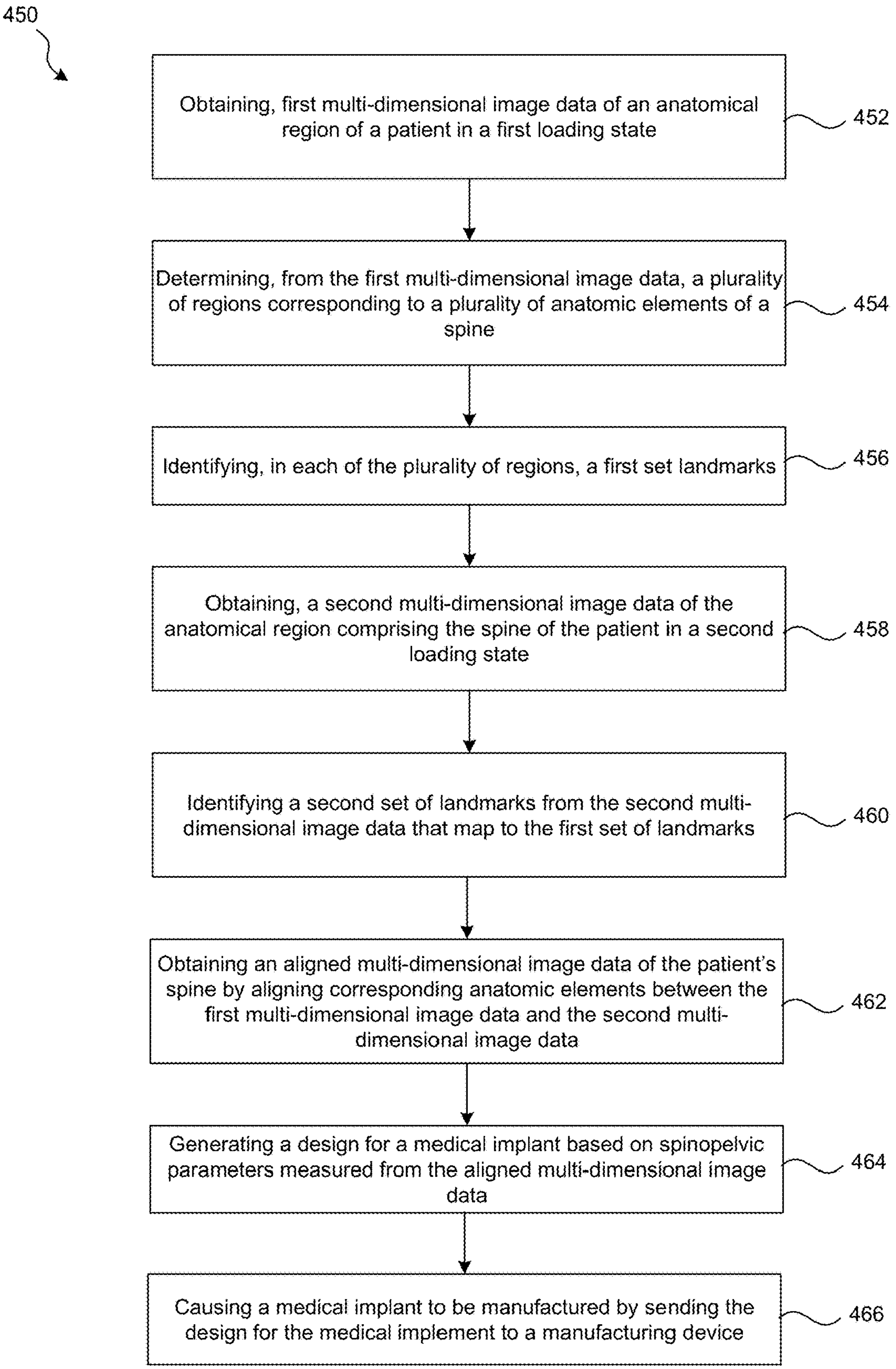
FIG. 4B shows an example flowchart of operations to map a portion of a human anatomy in a multi-dimensional image data to a corresponding portion of the same human anatomy in another multi-dimensional image data.

FIG. 4B shows an example flowchart 450 of operations to map a portion of a human anatomy in a multi-dimensional image data to a corresponding portion of the same human anatomy in another multi-dimensional image data. Flowchart 450 can be used to map common landmarks from two 2D images (e.g., anterior-posterior (AP) and lateral) to a 3D image for each of at least three landmarks per vertebra. For each vertebra, each of the one or more 3D landmarks includes three coordinates (e.g., x, y, z), each of the one or more 2D landmarks in the first view (e.g., AP view) has two coordinates (e.g., x, y), and each of the one or more 2D landmarks in the second view (e.g., lateral view) has two coordinates (e.g., y, z).

Operation 452 includes obtaining a first multi-dimensional image data of an anatomical region of a patient in a first loading state. In some embodiments, the first loading state may be in horizontal (or non-load-bearing) position. Operation 454 includes determining, from the first multi-dimensional image data, a plurality of regions corresponding to a plurality of anatomical elements of a spine. Operation 456 includes identifying, in each of the plurality of regions, a first set of landmarks. Operation 458 includes obtaining a second multi-dimensional image data of the anatomical region comprising the spine of the patient in a second loading state. In some embodiments, the second loading state may be in a vertical (or loaded or load-bearing) position. Operation 460 includes identifying a second set of landmarks from the second multi-dimensional image data that map to the first set of landmarks. Operation 462 includes obtaining an aligned multi-dimensional image data of the patient's spine by aligning corresponding anatomical elements between the first multi-dimensional image data and the second multi-dimensional image data. Operation 464 includes generating a design for a medical implant based on spinopelvic parameters measured from the aligned multi-dimensional image data. Operation 466 includes causing a medical implant to be manufactured by sending the design for the medical implant to a manufacturing device.

The operations of flowchart 450 can be performed by an image processing module using example techniques described in this patent document. In some embodiments, the first multi-dimensional image data is collected in three dimensions, and the second multi-dimensional image data is collected in two dimensions. In some embodiments, the aligned multi-dimensional image data is a three-dimensional image. In some embodiments, the obtaining the aligned multi-dimensional image data includes: modifying positions of the plurality of anatomical elements in the first multi-dimensional image data according to positions of the plurality of anatomical elements in the second multi-dimensional image data. In some embodiments, the method further comprises determining a loading-state mapping based on the first and second loading states, and performing the loading-state mapping between the first multi-dimensional image data and the second multi-dimensional image data to generate the aligned multi-dimensional image data.

In some embodiments, in response to a region being a lumbar vertebra, the identifying the first set of landmarks of the region includes identifying the following: an inferior aspect of spinous process of the lumbar vertebrae, a superior aspect of spinous process of the lumbar vertebrae, a left aspect of transverse process of the lumbar vertebrae, and a right aspect of transverse process of the lumbar vertebrae. In some embodiments, the aligning the corresponding anatomical elements between the first multi-dimensional image data and the second multi-dimensional image data includes aligning a sacrum between a three-dimensional (3D) image data and a two-dimensional (2D) image data by: creating, from the 3D image data, a first image data along a sagittal view that bisects the sacrum; projecting a second image data along the sagittal view from the 2D image data onto the first image data, wherein the second image data comprises the sacrum; and causing the sacrum from the first image data to overlap with the sacrum of the second image data by scaling, rotating, and/or translating the first image data.

In some embodiments, the aligning the corresponding anatomical elements includes aligning each lumbar vertebra between the 3D image data and the 2D image data that is performed in response to the aligning the sacrum by: performing a first aligning operation of a lumbar vertebra by moving an anterior landmark and a posterior landmark of the lumbar vertebra in the 3D image data to match the same landmarks on the second image data from the 2D image data, wherein the second image data comprises the lumbar vertebra; creating, from the 3D image data, a third image data along a coronal view that extends across the sacrum; projecting a fourth image data along the coronal view from the 2D image data onto the third image data, wherein the fourth image data comprises the sacrum; causing the sacrum from the third image data to overlap with the sacrum of the second image data by scaling or translating the first image data; and performing a second aligning operation of the lumbar vertebra by moving the anterior landmark and the posterior landmark for the lumbar vertebra to match the same landmarks on the fourth image data from the 2D image, wherein the fourth image data comprises the lumbar vertebra.

In some embodiments, the method further comprises adjusting one or more other landmarks of the lumbar vertebra by a same amount as that used to move the anterior landmark and the posterior landmark of the lumbar vertebra in the 3D image data for the first aligning operation; and adjusting one or more other landmarks of the lumbar vertebra by a same amount as that used to move the anterior landmark and the posterior landmark of the lumbar vertebra in the 3D image data for the second aligning operation. In some embodiments, the first multi-dimensional image data is obtained from a computer tomography (CT) scan or a magnetic resonance imaging (MRI) scan, and wherein the second multi-dimensional image data is obtained from an X-ray scan.

Figure 5:
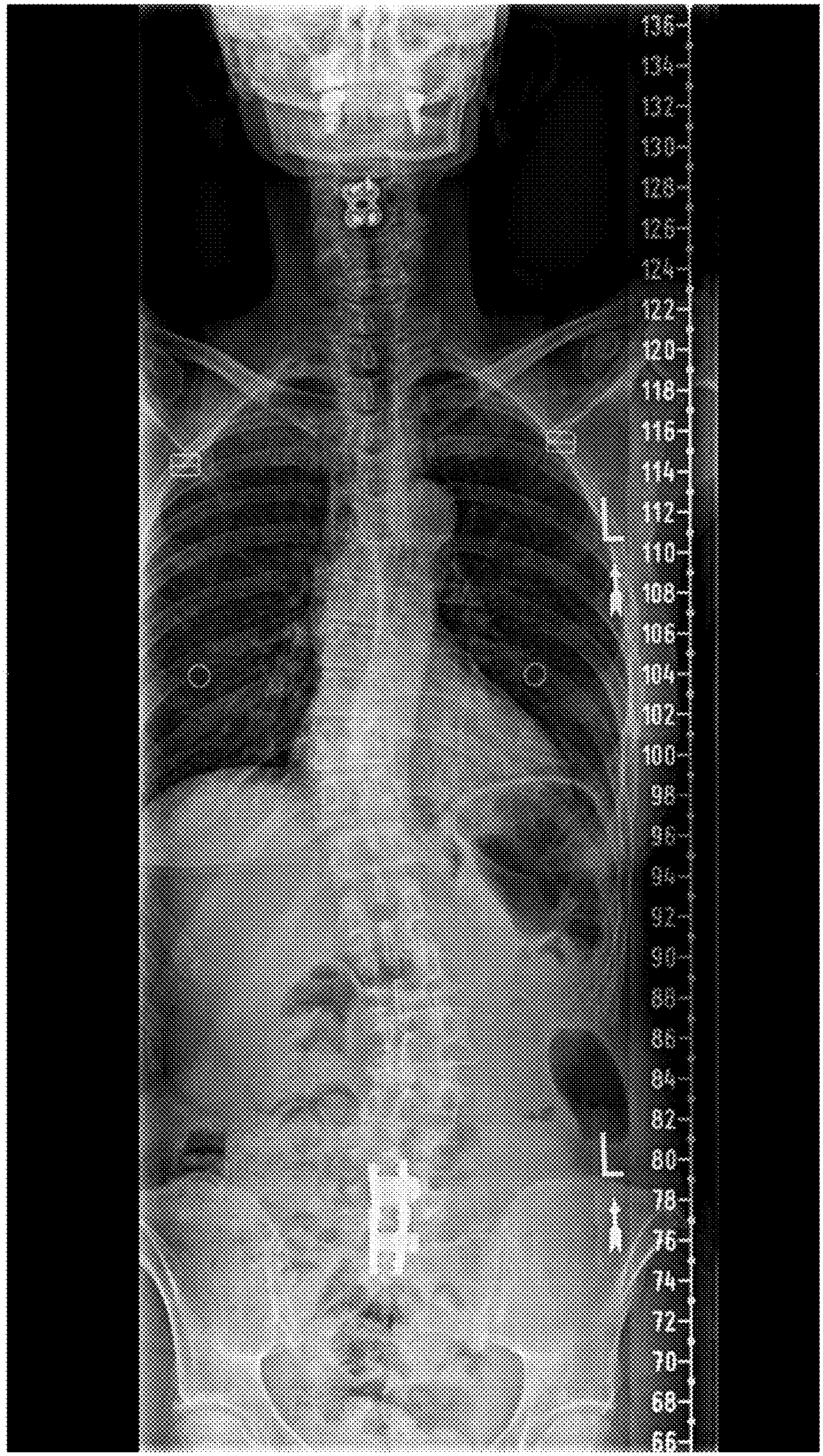
FIG. 5 shows an example 2D image of an anterior-posterior view of a spine obtained from an X-ray.

FIG. 5 shows an example 2D image 500 of an anterior-posterior (AP) view (or coronal view) of a spine obtained from an X-ray. The 2D image 500 shows a curve of a spine in an AP view when the spine is in a vertical (or loaded or load-bearing) position. The 2D image 500 also shows that the plurality of vertebrae have different 2D locations (e.g., a set of two coordinates such as y and z) in 2D space, where an image processing module can analyze each segment or each anatomical element of the vertebrae to identify a landmark with 2D coordinates as explained above in this patent document. The image processing module can determine a loading state of the spine (e.g., whether the spine is in an unloaded state, a load-bearing state, or another state) based on user input (e.g., user indicates the loading state), anatomical configuration of the spine, type of image data (e.g., X-ray, CT scan), machine learning algorithms, metadata, etc. For example, the image processing module can determine that the image 500 is a 2D image taken in a load-bearing state. The image processing module can then map features based on the loading states, predict anatomical configurations for loading states, or the like.

Figure 6:
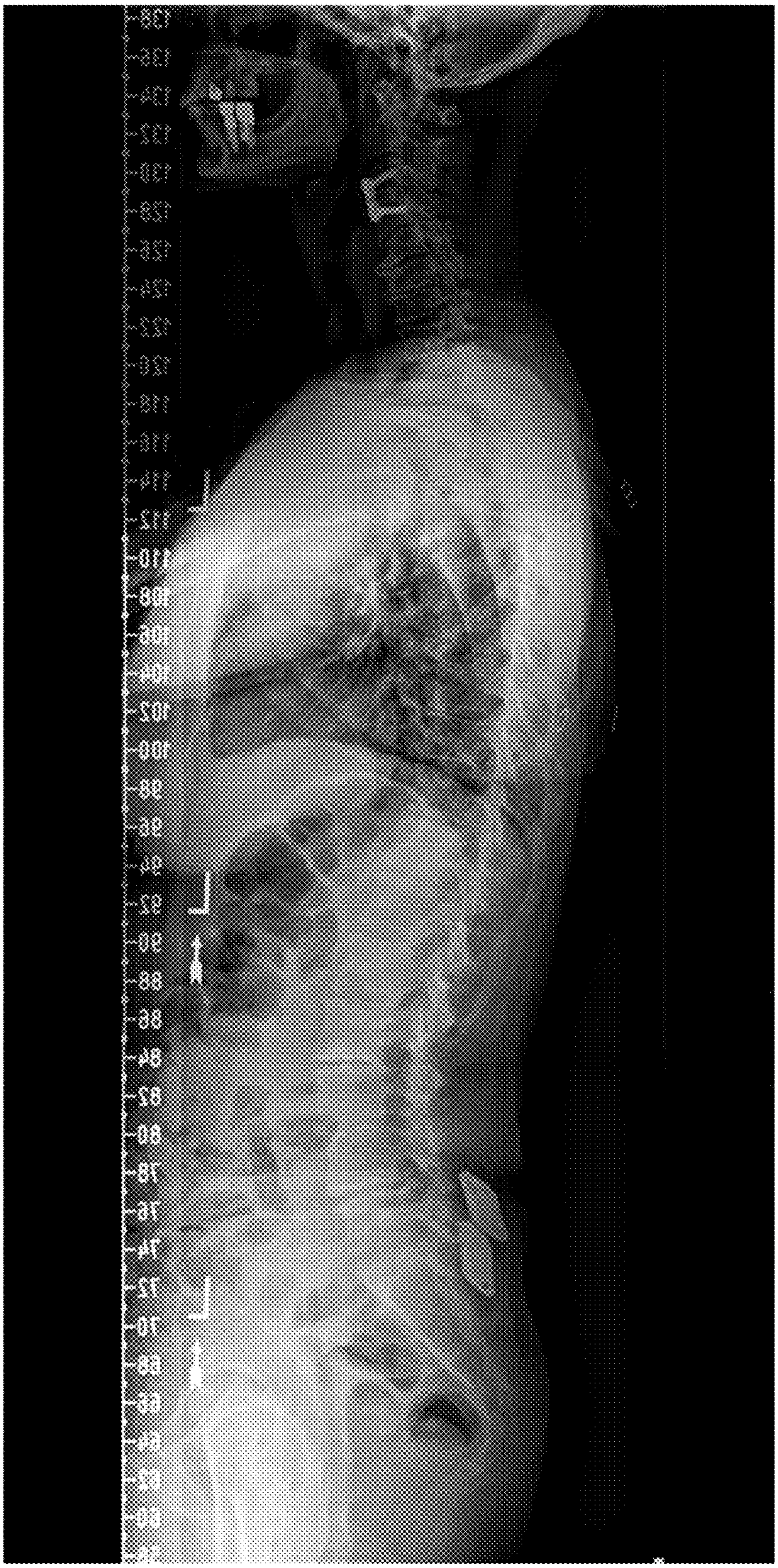
FIG. 6 shows an example 2D image of a lateral view of a spine obtained from an X-ray.

FIG. 6 shows an example 2D image 600 of a lateral view (or sagittal view) of a spine obtained from an X-ray. The 2D image 600 shows a curve of a spine in a lateral view when the spine is in a vertical (or loaded or load-bearing) position. The 2D image 600 also shows that the plurality of vertebrae have different 2D locations (e.g., another set of two coordinates, such as x and y) in 2D space, where an image processing module can analyze each segment or each anatomical element of the vertebrae to identify a landmark with 2D coordinates as explained above in this patent document.

Figure 7:
FIG. 7 shows an example 2D image of a coronal view of a region of a spine obtained from a CT scan.
Figure 8:
FIG. 8 shows an example 2D image of a coronal view of a region of a spine obtained from a CT scan.
Figure 9:
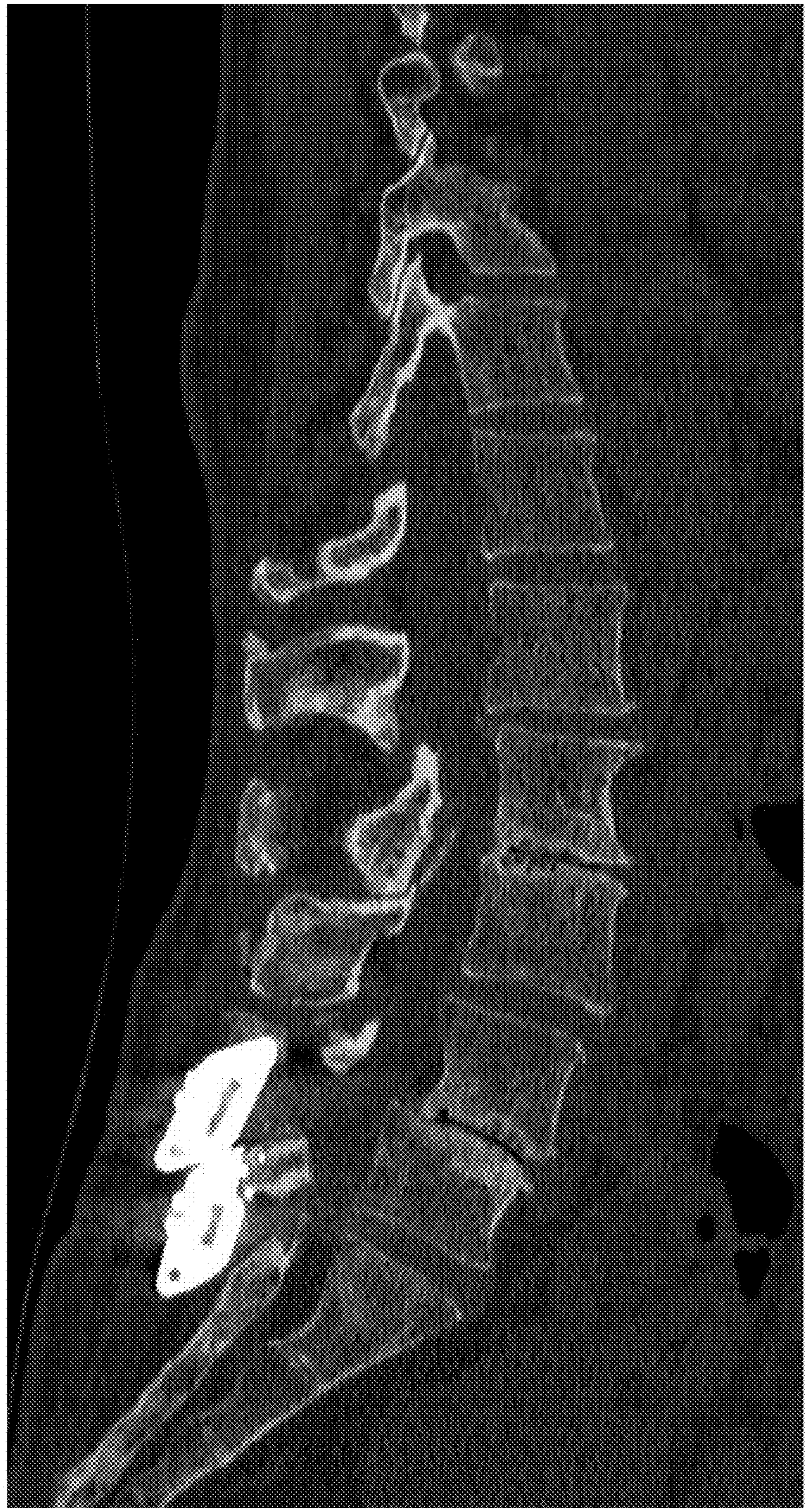
FIG. 9 shows an example 2D image of a sagittal view of a region of a spine obtained from a CT scan.

FIG. 7 shows an example 2D image 700 of a coronal view of a region of a spine obtained from a CT scan. The 2D image 700 is shown to focus on L4-L5 vertebrae. The 2D image 700 shows a curve of the region of the spine from a coronal view when the spine is in a horizontal (or non-load-bearing) position. The image processing module can determine that the spine is in a non-load-bearing configuration based on CT scans being taken when the patient is in a non-load-bearing position, user input, metadata associated with the image, or the like. The 2D image 700 also shows the gaps between the vertebrae. FIG. 8 shows an example 2D image 800 of a coronal view of a region of a spine obtained from a CT scan. The 2D image 800 is shown to focus on L5-S1 vertebrae. The 2D image 800 shows a coronal view of a curve of the L5-S1 region of the spine when the spine is in a horizontal (or non-load-bearing) position. For both FIG. 7 and FIG. 8, an image processing module can analyze the 2D images 700, 800 to identify landmarks in the 2D images 700, 800 as explained in this patent document. FIG. 9 shows an example 2D image 900 of a sagittal view of a region of a spine obtained from a CT scan. The 2D image 900 is shown to focus on the lumbar region of the spine. The 2D image 900 shows a sagittal view of a curve of the spine and the gaps between the segments or the anatomical elements when the spine is in a horizontal (or non-load-bearing) position.

Figure 10:
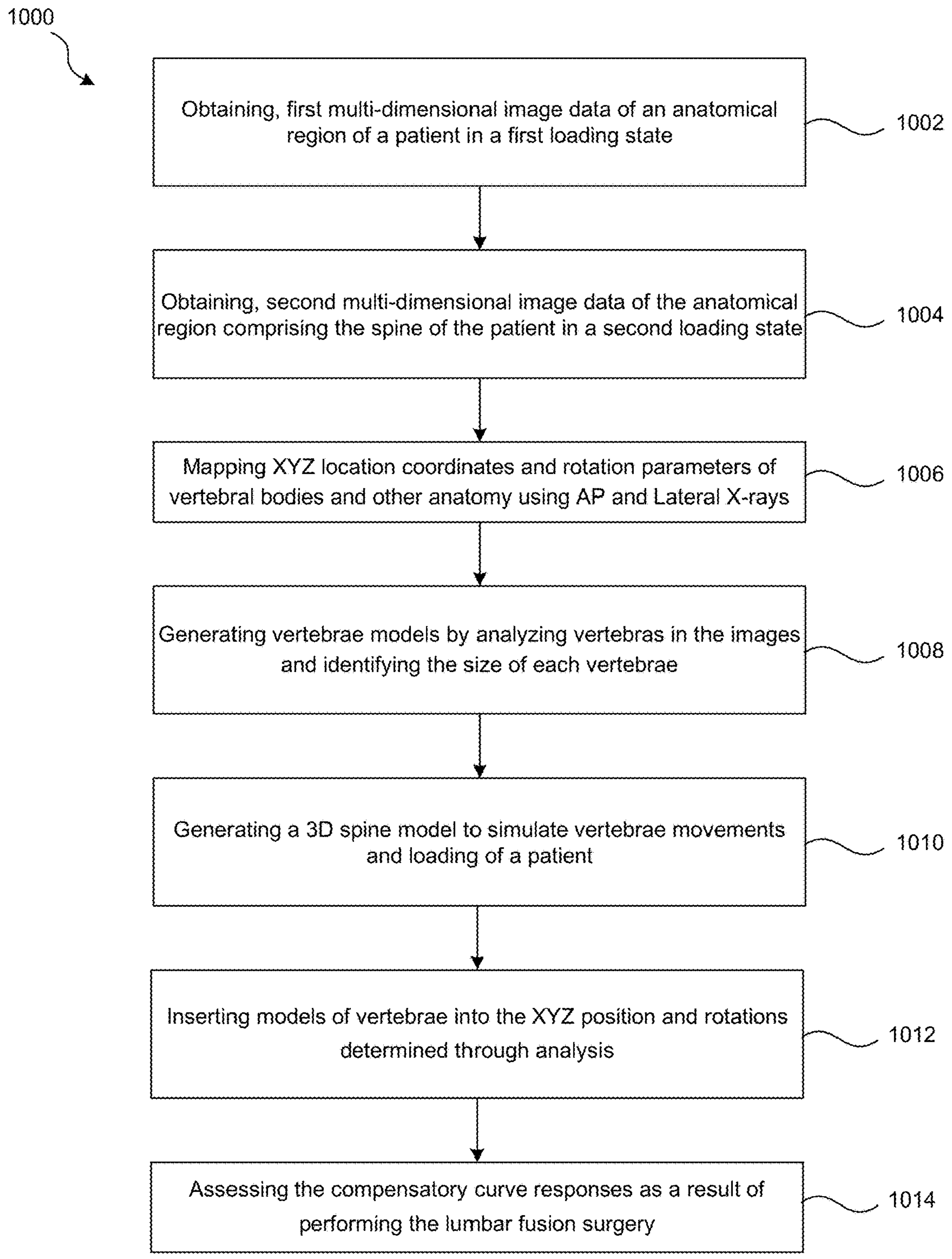
FIG. 10 shows an example flowchart of operations to generate a 3D spine model to simulate vertebrae movements and loading of a patient.

FIG. 10 shows an example flowchart 1000 of operations to generate a 3D spine model to simulate vertebrae movements and loading on a spine of a patient in accordance with an embodiment. The flowchart 1000 can generate a 3D spine model used to perform simulations, such as movement and/or loading of anatomical elements (e.g., vertebral bodies, implants, etc.) at various levels for different loading states. For example, images of anatomy in different loading states can be compared to determine loading information (e.g., how loading affects anatomical elements). The determined loading information can be used to generate 3D anatomical models representing one or more loading conditions. The operations can be used to map a portion of a human anatomy in a 3D image study to a corresponding portion of the same human anatomy in a 2D image, as discussed in connection with FIGS. 4A and 4B. For example, the steps discussed in connection with FIGS. 4A and 4B can be incorporated into or replace steps discussed in connection with operations discussed in connection with FIG. 10.

The flowchart 1000 3D spine model can include 3D virtual vertebral bodies with accurate size, orientation, and position at levels with acquired imaging (e.g., anterior-posterior (AP) and lateral). A 3D model of the spine can allow a healthcare provider (e.g., surgeon, therapist, etc.) or implant designer to perform spinal 3D planning (e.g., SVA, CSVL, TK, LL, PI, PT) with imaging inputs (e.g., X-ray, CT scans, etc.) of the patient. The 3D spine model can simulate compensatory and/or reciprocal mechanisms to lumbar corrections. For example, the 3D model can be used to predict pelvic tilt compensatory response to lumbar corrections, thoracic kyphosis compensatory response to lumbar corrections, or cervical lordosis compensatory response to lumbar corrections. Planning global alignment with compensatory curves can result in more successful surgeries and better patient health outcomes. The 3D spine model can allow surgeons, sales representatives, medical decision makers (MDMs), and patients to see the target alignment (e.g., SVA, CSVL, TK, PT, etc.) for the procedure that is being planned. For example, the 3D placement of other anatomy, such as iliac crests and ribs, can give surgeons a visual of the access to disc spaces. Planning for L45 LLI with the 3D visualization of the iliac crests could flag, for example, obstructions, such as inserter/implant to iliac crest insertion obstructions.

Flowchart 1000 can be used to map common landmarks from two 2D images (e.g., AP images and lateral images) to 3D images for each of at least three landmarks per vertebra. For each vertebra, each of the one or more 3D landmarks includes three coordinates (e.g., x, y, z), each of the one or more 2D landmarks in the first view (e.g., AP view) has two coordinates (e.g., x, y), and each of the one or more 2D landmarks in the second view (e.g., lateral view) has two coordinates (e.g., y, z).

Operation 1002 includes obtaining a first multi-dimensional image data (e.g., CT scan data) of an anatomical region of a patient in a first loading state. In some embodiments, the first loading state may be when the patient is in a horizontal (or non-load-bearing) position. For example, the patient can be lying down during the CT scan. The system (e.g., image processing module, system 200, image processing module 364, etc.) can determine, from the first multi-dimensional image data, a plurality of regions corresponding to a plurality of anatomical elements of a spine. Operation 1002 can include performing segmentation by identifying different structures or tissues within the images. This process can be performed manually by a user or can be automated using one or more segmentation routines. Segmentation routines can be used to extract specific regions of interest vertebrae, vertebral bodies, discs, etc., from the surrounding tissues.

Operation 1004 includes obtaining a second multi-dimensional image data (e.g., planar X-ray data, orthogonal contemporaneous X-ray data, or other X-ray data) of the anatomical region comprising the spine of the patient in a second loading state. The system can identify a second set of landmarks from the second multi-dimensional image data that map to the first set of landmarks. Operation 1004 includes obtaining an aligned multi-dimensional image data of the patient's spine by aligning corresponding anatomical elements between the first multi-dimensional image data and the second multi-dimensional image data. In some embodiments, operation 1004 includes obtaining loading-effect data by comparing the positions of corresponding anatomical elements in the first multi-dimensional image data and the second multi-dimensional image data. The loading-effect data can be correlated to the known loading when the first and second multi-dimensional image data were acquired. The loading-effect data can be used to predict positions of the anatomical elements for additional loading conditions.

Operation 1006 includes mapping XYZ location coordinates and rotation parameters of vertebral bodies and other anatomy using AP and lateral X-rays. The XYZ location coordinates and rotation parameters of anatomy are determined by taking the XYZ location coordinates of anatomy landmarks that are visible in the AP and/or lateral view of images. These coordinates and parameters are taken in reference to a common origin, such as the posterior edge of S1. The system can use an anatomy sizing module to circumscribe a bounding box around the anatomy of interest and size a library of vertebra models to replicate the approximate size of each vertebral/auxiliary body. The system can position these sized bodies into their identified XYZ location coordinates and rotation parameters.

Operation 1008 can include creating three-dimensional representations of the structures of interest. Three-dimensional reconstruction techniques use segmented data to generate virtual models, capturing the shape, size, and spatial relationships of the structures of interest. The resolution of the acquired images can affect the level of detail and accuracy of the generated three-dimensional representations. The operation 1008 can include generating vertebrae models by analyzing vertebrae in the images and identifying the size of each vertebra. In some embodiments, images are segmented to identify features (e.g., boundaries of anatomical elements, such as vertebrae). The segmented features from the images can be analyzed to determine boundaries of the vertebrae. Images taken from different perspectives can be combined to determine three-dimensional boundaries of the vertebrae. Landmarks can be identified and keyed to landmarks and other images to perform image mapping between different types of images, including images acquired using different equipment (e.g., CT scanners, X-ray machines, MRI machines, etc.), imaging modalities, or the like. Measuring routines can be applied to the images and vertebrae to measure the vertebrae.

Operation 1010 includes generating a 3D spine model to simulate vertebrae movements and loading of a patient. The 3D spine model can simulate compensatory mechanisms to lumbar corrections. For example, the 3D spine model can be used to predict other non-instrumented lumbar levels, pelvic tilt compensatory response to lumbar corrections, thoracic compensatory response to lumbar corrections, or cervical compensatory response to lumbar corrections. Techniques for generating 3D models are discussed in connection with FIGS. 1-9 and U.S. application Ser. No. 16/569,494, filed on Sep. 12, 2019, titled "SYSTEMS AND METHODS FOR ORTHOPEDIC IMPLANTS," U.S. application Ser. No. 16/735,222 (now U.S. Pat. No. 10,902,944), filed Jan. 6, 2020, titled "PATIENT-SPECIFIC MEDICAL PROCEDURES AND DEVICES, AND ASSOCIATED SYSTEMS AND METHODS," and U.S. application Ser. No. 16/242,877, filed on Jan. 8, 2019, titled "SYSTEMS AND METHODS OF ASSISTING A SURGEON WITH SCREW PLACEMENT DURING SPINAL SURGERY," which are incorporated by reference in their entireties.

Operation 1012 includes inserting the models of vertebrae into the 3D spine model according to the XYZ position coordinates and translational, scaling, and/or rotation parameters determined through the analysis. Inserting auxiliary anatomy can occur using landmarks (e.g., iliac crest and ribs) visible on the AP and lateral imaging. Operation 1012 can include moving or generating anatomical models for the three-dimensional spine model. For example, vertebrae can be generated based on imaged vertebrae. The generation process can take into account existing virtual anatomical models in the three-dimensional spine model, thereby ensuring a desired fit between anatomical features. The fit can be confirmed based on measurements of the three-dimensional spine model to measurements obtained using images. In some embodiments, operation 1012 can include moving vertebrae to position the vertebrae in a three-dimensional spine model. For example, a three-dimensional spine model can be generated based, at least in part, on images from a first data set. A second data set can be analyzed to determine new positions of the vertebrae. For example, the new positions can be under a loaded state whereas the first set of data is under a non-loaded state. Accordingly, multiple three-dimensional spine models can be generated representing multiple states of the patient. Additionally, multiple loaded three-dimensional spine models can be generated representing different loading conditions, such as when a patient stands, performs a task, or the like.

Operation 1014 includes assessing the compensatory responses (e.g., compensatory curve responses and/or reciprocal changes) as a result of performing a procedure, such as fusion surgery (e.g., lumbar fusion surgery, cervical fusion surgery, etc.).

The advantage of performing the operations of flowchart 1000 is that it builds upon personalized surgical planning by adding in the functionality of measuring and predicting alignment (e.g., regional alignment such as a region of interest selected by a user, global alignment, etc.) and displaying the results to users. By determining the locations of anatomical features (e.g., discs, vertebral bodies, spinous processes, joints (e.g., facet joints), or the like) while the spine is loaded with body weight, the system can predict a synthetic/hybrid standing CT, plan surgical procedures, and simulate the spine's shape in local and remote locations. In some procedures, flowchart 1000 is used to predict alignment based upon a lumbar fusion procedure. The system can predict the shape of the patient's spine in, for example, thoracic and/or cervical regions. This allows a user to evaluate predicted changes to different spinal segments that may not be modified directly during the surgical procedure. The system can identify far anatomical effects caused by anatomical adjustments at a surgical site, wherein the far anatomical effects are remote from the surgical site, and can determine one or more relationships between the anatomical adjustments and the far anatomical effects. In response to determining the one or more relationships, send a notification to a user. U.S. Application No. 63/437,975 discloses how to calculate and display reciprocal changes to nearby anatomy due to correction of index anatomy. For example, the system can model the anatomical changes to the thoracic and cervical spines based on corrections to the lumbar spine. U.S. Application No. 63/437,975 is incorporated by reference in its entirety.

The operations of flowchart 1000 can be performed by an image processing module. The first multi-dimensional image data is collected in three dimensions, and the second multi-dimensional image data is collected in two dimensions. The aligned multi-dimensional image data is a three-dimensional image. In some embodiments, the obtaining the aligned multi-dimensional image data includes: modifying positions of the plurality of anatomical elements in the first multi-dimensional image data according to positions of the plurality of anatomical elements in the second multi-dimensional image data. In some embodiments, the method further comprises determining a loading-state mapping based on the first and second loading states, and performing the loading-state mapping between the first multi-dimensional image data and the second multi-dimensional image data to generate the aligned multi-dimensional image data.

In some embodiments, in response to a region being a lumbar vertebra, the identifying the first set of landmarks of the region includes identifying the following: an inferior aspect of spinous process of the lumbar vertebrae, a superior aspect of spinous process of the lumbar vertebrae, a left aspect of transverse process of the lumbar vertebrae, and a right aspect of transverse process of the lumbar vertebrae. In some embodiments, the aligning the corresponding anatomical elements between the first multi-dimensional image data and the second multi-dimensional image data includes aligning a sacrum between a three-dimensional (3D) image data and a two-dimensional (2D) image data by: creating, from the 3D image data, a first image data along a sagittal view that bisects the sacrum; projecting a second image data along the sagittal view from the 2D image data onto the first image data, wherein the second image data comprises the sacrum; and causing the sacrum from the first image data to overlap with the sacrum of the second image data by scaling, rotating, and/or translating the first image data.

In some embodiments, the aligning the corresponding anatomical elements includes aligning each lumbar vertebra between the 3D image data and the 2D image data that is performed in response to the aligning the sacrum by: performing a first aligning operation of a lumbar vertebra by moving an anterior landmark and a posterior landmark of the lumbar vertebra in the 3D image data to match the same landmarks on the second image data from the 2D image data, wherein the second image data comprises the lumbar vertebra; creating, from the 3D image data, a third image data along a coronal view that extends across the sacrum; projecting a fourth image data along the coronal view from the 2D image data onto the third image data, wherein the fourth image data comprises the sacrum; causing the sacrum from the third image data to overlap with the sacrum of the second image data by scaling, rotating, or translating the first image data; and performing a second aligning operation of the lumbar vertebra by moving the anterior landmark and the posterior landmark for the lumbar vertebra to match the same landmarks on the fourth image data from the 2D image, wherein the fourth image data comprises the lumbar vertebra.

In some embodiments, the method further comprises adjusting one or more other landmarks of the lumbar vertebra by a same amount as that used to move the anterior landmark and the posterior landmark of the lumbar vertebra in the 3D image data for the first aligning operation; and adjusting one or more other landmarks of the lumbar vertebra by a same amount as that used to move the anterior landmark and the posterior landmark of the lumbar vertebra in the 3D image data for the second aligning operation. In some embodiments, the first multi-dimensional image data is obtained from a computer tomography (CT) scan or a magnetic resonance imaging (MRI) scan, and wherein the second multi-dimensional image data is obtained from an X-ray, multiple X-ray studies, or the like.

Figure 11:
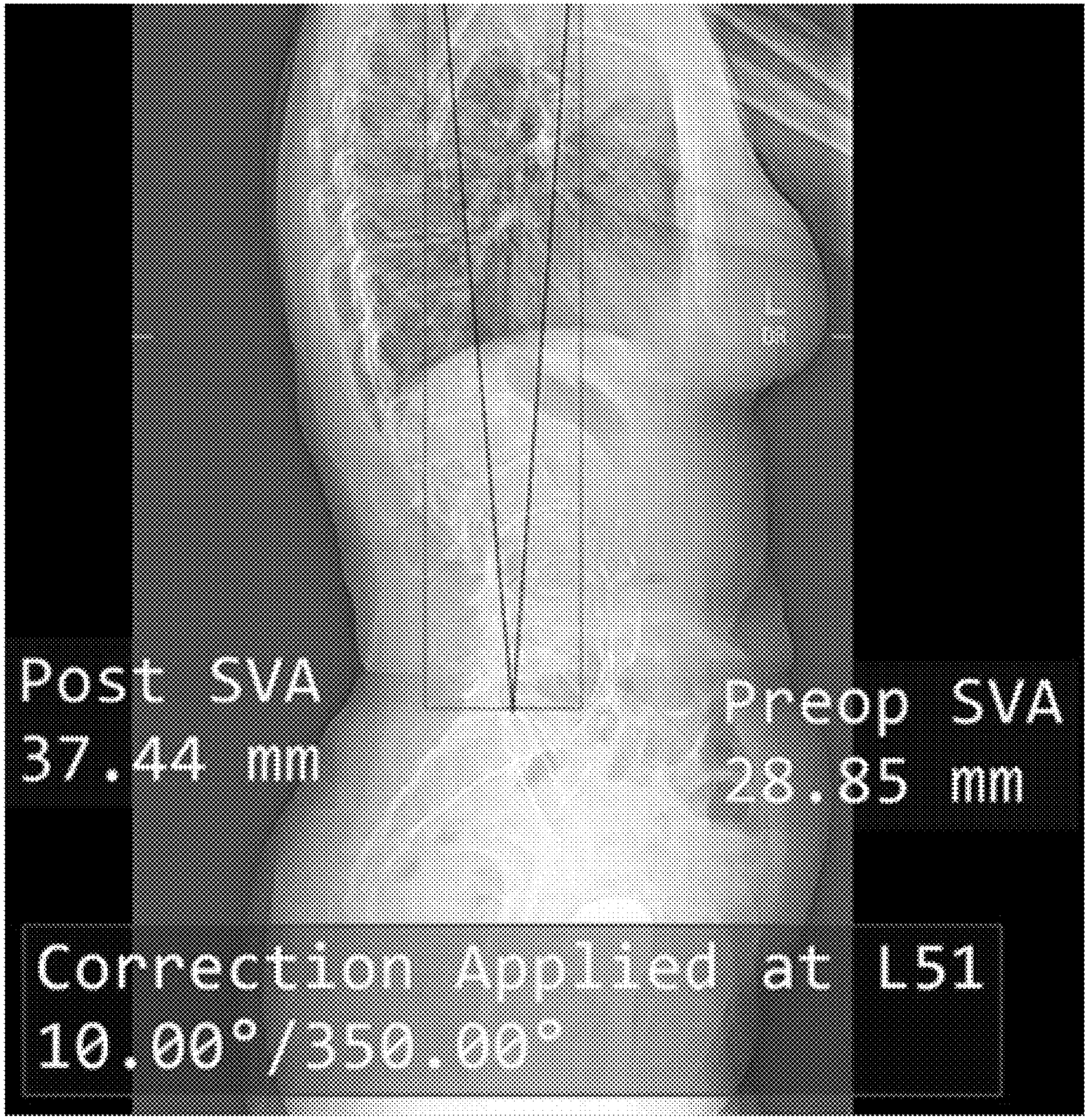
FIG. 11 shows an example 2D image of a view of a spine with sagittal vertical axis measurements obtained from an X-ray.

FIG. 11 shows an example 2D image 1100 of a view of a spine with sagittal vertical axis measurements obtained from an X-ray.

FIG. 12 illustrates an exemplary surgical plan report 1200 that may be used and/or generated in connection with the methods described herein, according to an embodiment.

Figure 13:
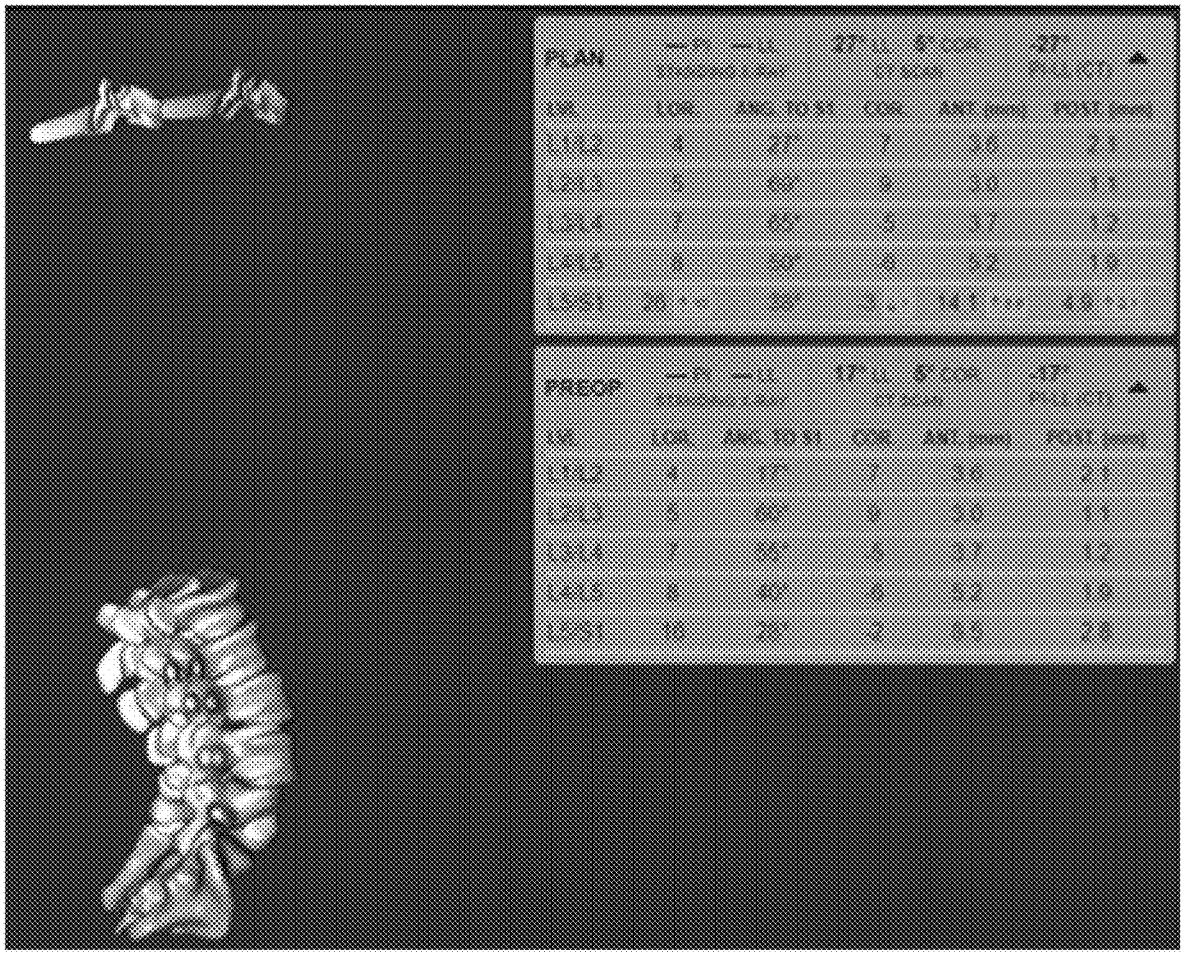
FIG. 13 illustrates an exemplary surgical plan report that may be used and/or generated in connection with the methods described herein, according to an embodiment.

FIG. 13 illustrates an exemplary surgical plan report 1300 that may be used and/or generated in connection with the methods described herein, according to an embodiment.

FIG. 14 illustrates exemplary XYZ and rotation measurements 1400 of anatomy of a patient, according to an embodiment.

Figure 15:
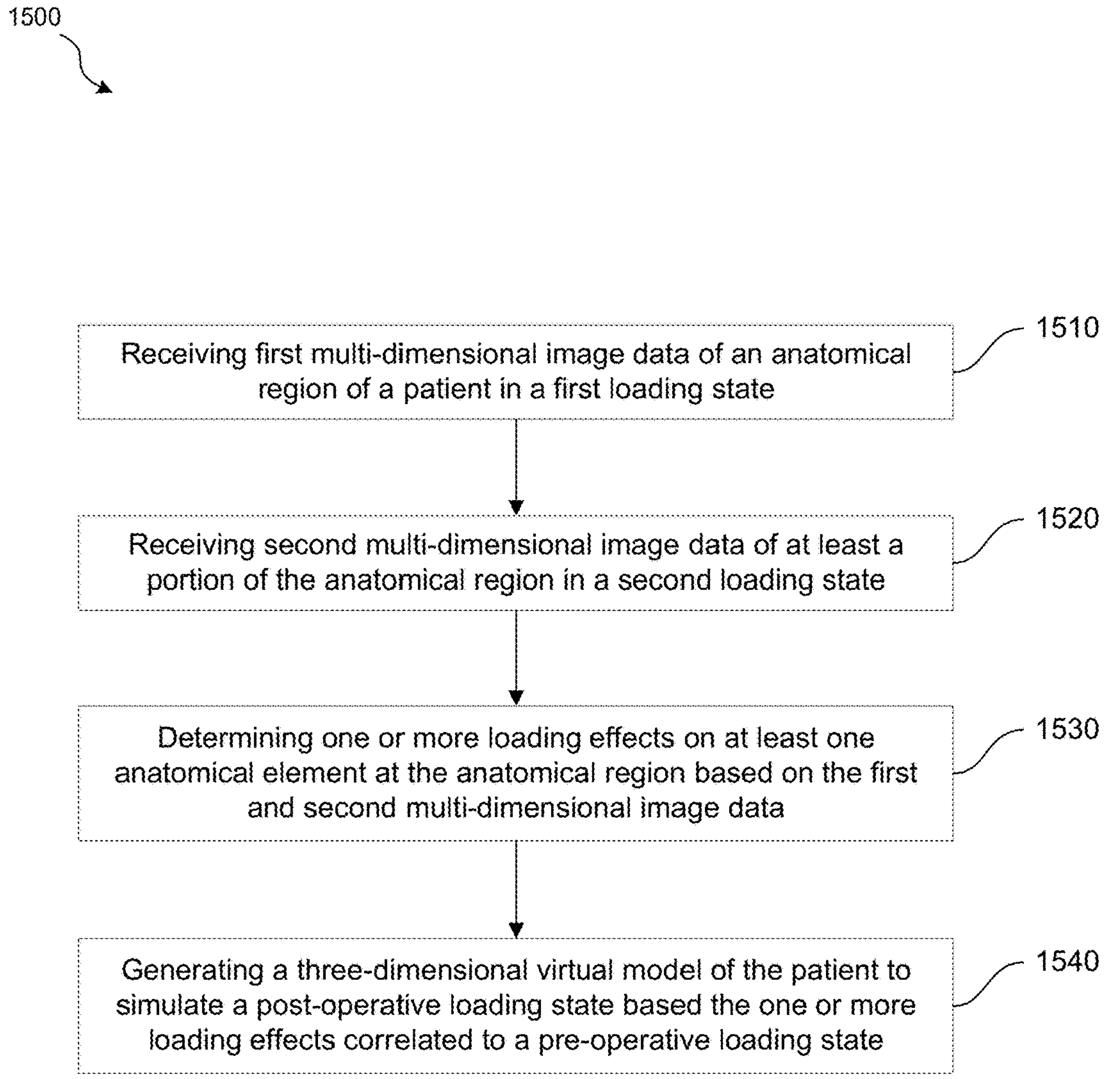
FIG. 15 shows an example flowchart of operations to generate a 3D virtual model to simulate a post-operative loading state of a patient in accordance with an embodiment.

FIG. 15 shows an example flowchart 1500 of operations to generate a 3D virtual model to simulate a post-operative loading state of a patient in accordance with an embodiment. The flowchart 1500 can generate a 3D spine model used to perform simulations, such as movement and/or loading of anatomical elements (e.g., vertebral bodies, implants, etc.) at various levels for different loading states pre-operatively and post-operatively. For example, images of anatomy in different loading states can be compared to determine loading information (e.g., how loading affects anatomical elements or location and organization of anatomical elements). The determined loading information can be used to generate 3D anatomical models representing one or more loading conditions. The operations can be used to map a portion of a human anatomy in a 3D image study to a corresponding portion of the same human anatomy in a 2D image, as discussed in connection with FIGS. 4A and 4B. For example, the steps discussed in connection with FIGS. 4A and 4B can be incorporated into or replace steps discussed in connection with operations discussed in connection with FIG. 15.

Operation 1510 includes receiving a first multi-dimensional image data (e.g., CT scan data) of an anatomical region (e.g., spinal region, such as the thoracic region and/or a cervical region of the patient's spine) of a patient in a first loading state. Operation 1510 includes obtaining a first multi-dimensional image data of an anatomical region of a patient in a first loading state. The system can model virtual lumbar anatomical elements matching anatomical elements shown in the first multi-dimensional image data based on a resolution level of the first multi-dimensional image data. In some embodiments, the first loading state may be when the patient is in a horizontal (or non-load-bearing) position. For example, the patient can be lying down during the CT or MRI scan. The system (e.g., image processing module, system 200, image processing module 364, etc.) can determine, from the first multi-dimensional image data, a plurality of regions corresponding to a plurality of anatomical elements of a spine. Operation 1510 can include performing segmentation by identifying different structures or tissues within the images. This process can be performed manually by a user or can be automated using one or more segmentation routines. Segmentation routines can be used to extract specific regions of interest vertebrae, vertebral bodies, discs, etc., from the surrounding tissues.

Operation 1520 includes receiving a second multi-dimensional image data (e.g., X-ray data) of at least a portion of the anatomical region (e.g., spinal region, such as a lumbar region of the patient's spine) in a second loading state. The system can model virtual anatomical elements of the thoracic region and cervical region matching anatomical elements shown in the second multi-dimensional image data based on a resolution level of the second multi-dimensional image data. The system can identify a second set of landmarks from the second multi-dimensional image data that map to the first set of landmarks. Operation 1520 includes obtaining an aligned multi-dimensional image data of the patient's spine by aligning corresponding anatomical elements between the first multi-dimensional image data and the second multi-dimensional image data. In some embodiments, operation 1520 includes obtaining loading-effect data by comparing the positions of corresponding anatomical elements in the first multi-dimensional image data and the second multi-dimensional image data. The loading-effect data can be correlated to the known loading when the first and second multi-dimensional image data were acquired. The loading-effect data can be used to predict positions of the anatomical elements for additional loading conditions.

Operation 1530 includes determining one or more loading effects on at least one anatomical element at the anatomical region based on the first and second multi-dimensional image data. The system can identify a first image type (e.g., CT scan) of the first multi-dimensional image data and determine the first loading state based on the first image type of the first multi-dimensional image data. The system can determine one or more anatomical metrics affected by the first loading state and measure the one or more anatomical metrics of the anatomical region using the first multi-dimensional image data. In some embodiments, the system uses the measured one or more anatomical metrics to generate a 3D model of the patient's spine. The system can select a mapping routine based on the first image type (e.g., CT scan), the second image type (e.g., X-ray), and/or anatomical elements at the anatomical region. The system can configure the mapping routine to map anatomical features in CT scans to the same anatomical features in X-rays and to determine one or more loading effects at the anatomical region based on positional differences of the same anatomical features attributable to loading during CT scans and X-rays.

Operation 1540 includes generating a 3D virtual model (e.g., 3D multi-region simulation model) of the patient to simulate a post-operative loading state based on the one or more loading effects correlated to a pre-operative loading state. Techniques for generating 3D models are discussed in connection with FIGS. 1-9 and U.S. application Ser. No. 16/569,494, filed on Sep. 12, 2019, titled "SYSTEMS AND METHODS FOR ORTHOPEDIC IMPLANTS," U.S. application Ser. No. 16/735,222 (now U.S. Pat. No. 10,902,944), filed Jan. 6, 2020, titled "PATIENT-SPECIFIC MEDICAL PROCEDURES AND DEVICES, AND ASSOCIATED SYSTEMS AND METHODS," and U.S. application Ser. No. 16/242,877, filed on Jan. 8, 2019, titled "SYSTEMS AND METHODS OF ASSISTING A SURGEON WITH SCREW PLACEMENT DURING SPINAL SURGERY," which are incorporated by reference in their entireties. The 3D model can include a first set of anatomical element models with high-fidelity surface topologies for designing one or more patient-specific implants. The 3D model can include a second set of anatomical element models for measuring spinal metrics for predicting a surgical outcome associated with implantation of the one or more patient-specific implants. In some cases, one or more of the anatomical element models of the second set have less feature data than all or some of the anatomical element models of the first set. The system can generate the 3D model by positioning, orienting, and/or scaling anatomical element models of the first set of anatomical elements for incorporation into the second set of anatomical elements.

The system can generate X-ray-fidelity anatomical element models based on one or more standing X-ray images of the second multi-dimensional image data. The system can generate tomographic-fidelity (e.g., polygon counts of number of polygons or triangles used to represent the model's surface; edge and curve smoothness, surface quality (surface roughness, continuity, and the presence of imperfections or artifacts that may affect the model's fidelity), level of geometric detail (inclusion of fine features, intricate structures, and smaller elements), matching to images, etc.) anatomical element models based on a set of tomographic images of the first multi-dimensional image data. The X-ray-fidelity anatomical element models have a resolution below a threshold fidelity and the tomographic-fidelity anatomical element models have a fidelity above the threshold fidelity, resolution above a threshold resolution, etc.

The system can generate a 3D multi-region spine model (e.g., including a cervical region and a thoracic region of the patient's spine) of the patient based on the first multi-dimensional image data and a 3D partial spine model (e.g., including a lumbar region model having surface topology data for designing one or more implants) matching the corresponding region of the spine imaged in the second multi-dimensional image data. The system can generate a 3D multi-region simulation model by combining anatomical elements of the 3D partial spine model with the 3D multi-region spine model. The system can replace lower-fidelity anatomical element models (e.g., based on X-ray images) of the 3D multi-fidelity spine model with the corresponding higher-fidelity anatomical elements (e.g., based on CT images or MRI study) of the 3D partial spine model anatomical elements. The system can collect additional multi-dimensional image data in other loading states and generate a replacement virtual model of an anatomical element for placement in the 3D virtual model.

Figure 16:
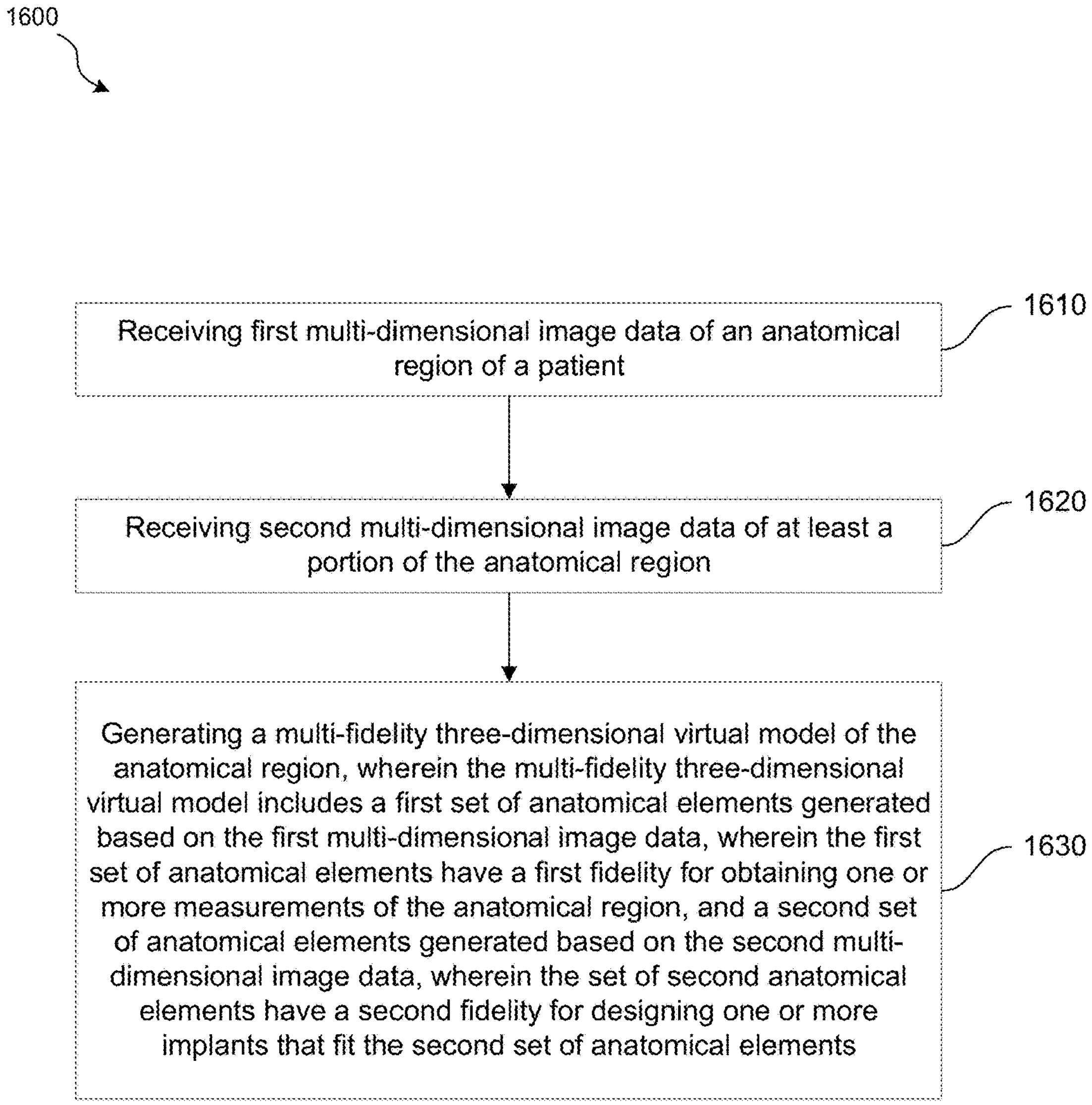
FIG. 16 shows an example flowchart of operations to generate a multi-fidelity 3D virtual model of an anatomical region of a patient in accordance with an embodiment.

FIG. 16 shows an example flowchart 1600 of operations to generate a multi-fidelity 3D virtual model of an anatomical region of a patient in accordance with an embodiment. The flowchart 1600 can generate a multi-fidelity 3D spine model used to perform simulations, such as movement and/or loading of anatomical elements (e.g., vertebral bodies, implants, etc.) at various levels for different loading states pre-operatively and post-operatively. For example, images of anatomy in different loading states can be compared to determine loading information (e.g., how loading affects anatomical elements). The determined loading information can be used to generate 3D anatomical models representing one or more loading conditions. The operations can be used to map a portion of a human anatomy in a 3D image study to a corresponding portion of the same human anatomy in a 2D image, as discussed in connection with FIGS. 4A and 4B. For example, the steps discussed in connection with FIGS. 4A and 4B can be incorporated into or replace steps discussed in connection with operations discussed in connection with FIG. 16.

Operation 1610 includes receiving a first multi-dimensional image data (e.g., CT scan data) of an anatomical region (e.g., spinal region, such as the thoracic region and/or a cervical region of the patient's spine) of a patient in a first loading state. Operation 1610 includes obtaining a first multi-dimensional image data of an anatomical region of a patient in a first loading state. The system can model virtual lumbar anatomical elements matching anatomical elements shown in the first multi-dimensional image data based on a resolution level of the first multi-dimensional image data. In some embodiments, the first loading state may be when the patient is in a horizontal (or non-load-bearing) position. For example, the patient can be lying down during the CT scan. The system (e.g., image processing module, system 200, image processing module 364, etc.) can determine, from the first multi-dimensional image data, a plurality of regions corresponding to a plurality of anatomical elements of a spine. Operation 1610 can include performing segmentation by identifying different structures or tissues within the images. This process can be performed manually by a user or can be automated using one or more segmentation routines. Segmentation routines can be used to extract specific regions of interest vertebrae, vertebral bodies, discs, etc., from the surrounding tissues.

Operation 1620 includes receiving a second multi-dimensional image data (e.g., X-ray data) of at least a portion of the anatomical region (e.g., spinal region, such as a lumbar region of the patient's spine) in a second loading state. The system can model virtual anatomical elements of the thoracic region and cervical region matching anatomical elements shown in the second multi-dimensional image data based on a resolution level of the second multi-dimensional image data. The system can identify a second set of landmarks from the second multi-dimensional image data that map to the first set of landmarks. Operation 1620 includes obtaining an aligned multi-dimensional image data of the patient's spine by aligning corresponding anatomical elements between the first multi-dimensional image data and the second multi-dimensional image data. In some embodiments, operation 1620 includes obtaining loading-effect data by comparing the positions of corresponding anatomical elements in the first multi-dimensional image data and the second multi-dimensional image data. The loading-effect data can be correlated to the known loading when the first and second multi-dimensional image data were acquired. The loading-effect data can be used to predict positions of the anatomical elements for additional loading conditions.

Operation 1630 includes generating (e.g., via a surgical planning platform) a multi-fidelity anatomical representation (e.g., a 3D virtual model) of a patient's anatomy or an anatomical region. A multi-fidelity 3D virtual model can include a first set of anatomical elements (e.g., a cervical spine, a thoracic spine, or a lumbar spine of the patient) generated based on the first multi-dimensional image data.

The first set of anatomical elements can have a first fidelity for obtaining one or more measurements of the anatomical region. The first fidelity can be above or below a threshold fidelity, and the second fidelity can be above or below a threshold fidelity for implant design. The fidelity can be based on, for example, number of mesh elements/volume of a meshed anatomical element, characteristics of 3D information (e.g., vertices, edges, polygonal faces for surface representation, encoded curves and curved surfaces, material data, etc.), whether a model has surfaces represented by small planar surfaces or curved surfaces, level of detail, type of source image data (e.g., number of images, pixel sizes, etc.), contouring algorithms (e.g., algorithms for generating anatomical contours based on image sets using convolutional neutral networks, machine learning systems, etc.), reconstruction program(s), voxel parameters, and/or additional fidelity metrics. Fidelity parameters or metrics can be scored by a user or the system to determine fidelities of the anatomical elements. For example, an anatomical model formed by curved surfaces generated based on a set of CT scans (e.g., scans at 1 mm slices, 1.5 mm slices, 128-slice CT scans, CT dose, etc.) can be assigned a higher fidelity than an anatomical model with flat polygonal faces presenting contoured surfaces based on X-rays. By way of another example, an anatomical model generated based on a 256-slice CT scan can be assigned a higher fidelity (e.g., 2×, 3×, or 4× higher) than an anatomical model generated based on a 16-slice CT scan. The threshold fidelity can be selected based on task(s) to be performed. Such tasks can include, for example, generating patient-matching surface contours, measuring anatomical value/metrics (e.g., metrics associated with spinal curvature and/or alignment), performing one or more anatomical element analyses (e.g., load-bearing analyses, fracture analyses, etc.), and other tasks disclosed herein. For example, an implant-design threshold fidelity for designing patient-matching surface contours of implants can be higher than a measurement threshold fidelity for measuring anatomical features (e.g., height of disc spaces, spine curvature, etc.).

In some embodiments, the multi-fidelity 3D virtual model can include a second set of anatomical elements (e.g., representing the lumbar spine of the patient) generated based on the second multi-dimensional image data. The set of second anatomical elements can have a second fidelity for designing one or more implants that fit the second set of anatomical elements. The system can simulate one or more lumbar corrections using the multi-fidelity three-dimensional virtual model. In response to the one or more simulated lumbar corrections, the system can generate at least one of a lumbar compensatory response, a pelvic tilt compensatory response, a thoracic compensatory response, or a cervical compensatory response.

The system can perform (e.g., using the surgical planning platform) a first task (e.g., designing at least one implant surface matching a patient surface) on a first region of the 3D virtual model based on a first fidelity level of the first region. The first fidelity level can correspond to a first level of image detail of the patient images in the first set of image data. Additionally, the system can perform (e.g., using the surgical planning platform) a second task on a second region of the 3D virtual model based on a second fidelity level of the second region. The second fidelity level can correspond to a second level of image detail of the patient images in the second set of image data. The number and types of tasks can be selected based on the procedure to be performed. The surgical planning platform can limit available tasks to each of a plurality of regions of the 3D multi-resolution virtual model based on a level of resolution for that region being acceptable for the available tasks. The surgical planning platform can assign usage constraints (e.g., multi-element constraints such as grouped anatomical element constraints, individual element constraints, etc.) to the three-dimensional multi-fidelity virtual model based a fidelity analysis of the three-dimensional multi-fidelity virtual model.

Figure 17:
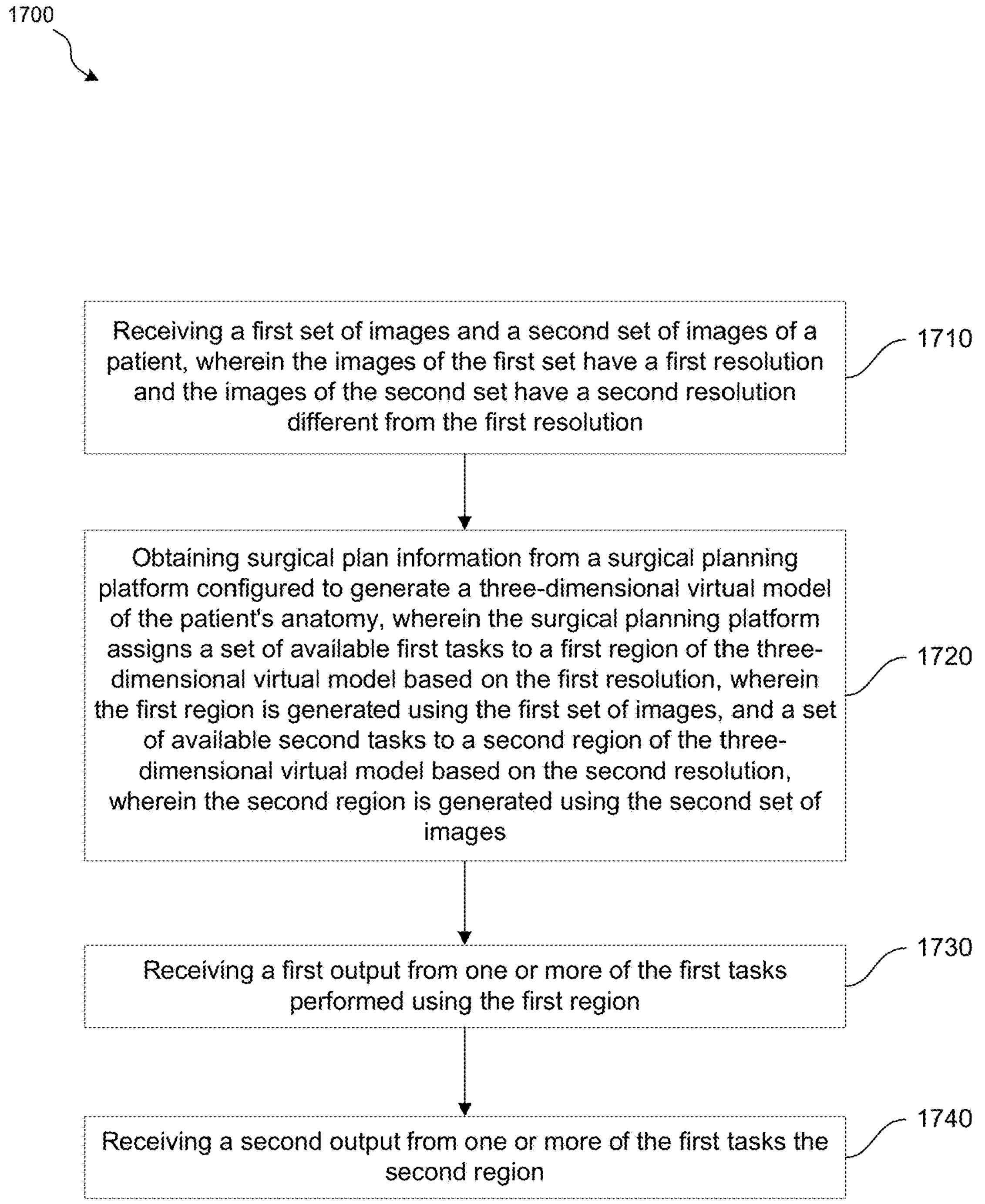
FIG. 17 shows an example flowchart of operations to generate a 3D virtual model of anatomy of a patient in accordance with an embodiment.

FIG. 17 shows an example flowchart 1700 of operations to generate a 3D virtual model of anatomy of a patient in accordance with an embodiment. The flowchart 1700 can generate a multi-fidelity 3D spine model used to perform simulations, such as movement and/or loading of anatomical elements (e.g., vertebral bodies, implants, etc.) at various levels for different loading states pre-operatively and post-operatively. For example, images of anatomy in different loading states can be compared to determine loading information (e.g., how loading affects anatomical elements). The determined loading information can be used to generate 3D anatomical models representing one or more loading conditions. The operations can be used to map a portion of a human anatomy in a 3D image study to a corresponding portion of the same human anatomy in a 2D image, as discussed in connection with FIGS. 4A and 4B. For example, the steps discussed in connection with FIGS. 4A and 4B can be incorporated into or replace steps discussed in connection with operations discussed in connection with FIG. 17.

Operation 1710 includes receiving a first set of image data (e.g., CT scan data or X-ray data) having a first resolution of an anatomical region (e.g., spinal region, such as the thoracic region and/or a cervical region of the patient's spine). The system can model virtual lumbar anatomical elements matching anatomical elements shown in the first set of image data based on a resolution level of the first set of image data. In some embodiments, the first loading state may be when the patient is in a horizontal (or non-load-bearing) position. For example, the patient can be lying down during the CT scan. The system (e.g., image processing module, system 200, image processing module 364, etc.) can determine, from the image data, a plurality of regions corresponding to a plurality of anatomical elements of a spine. Operation 1710 can include performing segmentation by identifying different structures or tissues within the images. This process can be performed manually by a user or can be automated using one or more segmentation routines. Segmentation routines can be used to extract specific regions of interest vertebrae, vertebral bodies, discs, etc., from the surrounding tissues.

Operation 1710 includes receiving a second set of image data (e.g., tomographic scan data) with a second resolution of at least a portion of the anatomical region (e.g., spinal region, such as a lumbar region of the patient's spine). The system can model virtual anatomical elements of the thoracic region and cervical region matching anatomical elements shown in the image data based on a resolution level of the second set of image data. The system can identify a second set of landmarks from the second set of image data that map to the first set of landmarks. Operation 1720 includes obtaining an aligned image data of the patient's spine by aligning corresponding anatomical elements between the first image data and the second image data. In some embodiments, operation 1720 includes obtaining loading-effect data by comparing the positions of corresponding anatomical elements in the first image data and the second image data. The loading-effect data can be correlated to the known loading when the first and second sets of image data were acquired. The loading-effect data can be used to predict positions of the anatomical elements for additional loading conditions.

Operation 1720 includes obtaining surgical plan information from a surgical planning platform configured to generate a 3D virtual model (e.g., 3D spinal model) of the patient's anatomy. The surgical planning platform can assign a set of available first tasks to a first region of the 3D virtual model based on the first resolution. The first region can be generated using the first set of images. In a first example, the set of available first tasks can include determining, in response to one or more spinal corrections at the second region, at least one of lumbar compensatory response, thoracic compensatory response, or cervical compensatory response. In a second example, the set of available first tasks can include determining multi-level spinal correction metrics measured at levels above the lumbar region.

The surgical planning platform can assign a set of available second tasks to a second region of the three-dimensional virtual model based on the second resolution. The second region can be generated using the second set of images. In a first example, the set of available second tasks can include determining pelvic tilt compensatory response in response to one or more spinal corrections at a lumbar level of the second region. In a second example, the set of available second tasks includes at least one of designing at least one of one or more spinal implants for implantation at the lumbar region, or measuring spinal metrics along the lumbar region.

Operation 1730 includes receiving a first output from one or more of the first tasks performed using the first region. The first region of the 3D virtual model can include virtual anatomical elements with X-ray feature details present in X-ray images in the first set of data. Operation 1740 includes receiving a second output from one or more of the first tasks of the second region. The second region of the 3D virtual model can include virtual anatomical elements with tomographic feature details present in tomographic images in the second set of data.

The embodiments, features, systems, devices, materials, methods, and techniques described herein may, in some embodiments, be similar to any one or more of the embodiments, features, systems, devices, materials, methods, and techniques described in the following:

- U.S. application Ser. No. 16/048,167, filed on Jul. 27, 2017, titled "SYSTEMS AND METHODS FOR ASSISTING AND AUGMENTING SURGICAL PROCEDURES";
- U.S. application Ser. No. 16/242,877, filed on Jan. 8, 2019, titled "SYSTEMS AND METHODS OF ASSISTING A SURGEON WITH SCREW PLACEMENT DURING SPINAL SURGERY";
- U.S. application Ser. No. 16/207,116, filed on Dec. 1, 2018, titled "SYSTEMS AND METHODS FOR MULTI-PLANAR ORTHOPEDIC ALIGNMENT";
- U.S. application Ser. No. 16/352,699, filed on Mar. 13, 2019, titled "SYSTEMS AND METHODS FOR ORTHOPEDIC IMPLANT FIXATION";
- U.S. application Ser. No. 16/383,215, filed on Apr. 12, 2019, titled "SYSTEMS AND METHODS FOR ORTHOPEDIC IMPLANT FIXATION";
- U.S. application Ser. No. 16/569,494, filed on Sep. 12, 2019, titled "SYSTEMS AND METHODS FOR ORTHOPEDIC IMPLANTS";
- U.S. Application No. 62/773,127, filed on Nov. 29, 2018, titled "SYSTEMS AND METHODS FOR ORTHOPEDIC IMPLANTS";
- U.S. Application No. 62/928,909, filed on Oct. 31, 2019, titled "SYSTEMS AND METHODS FOR DESIGNING ORTHOPEDIC IMPLANTS BASED ON TISSUE CHARACTERISTICS";
- U.S. application Ser. No. 16/735,222 (now U.S. Pat. No. 10,902,944), filed Jan. 6, 2020, titled "PATIENT-SPECIFIC MEDICAL PROCEDURES AND DEVICES, AND ASSOCIATED SYSTEMS AND METHODS";
- U.S. application Ser. No. 16/987,113, filed Aug. 6, 2020, titled "PATIENT-SPECIFIC ARTIFICIAL DISCS, IMPLANTS AND ASSOCIATED SYSTEMS AND METHODS";
- U.S. application Ser. No. 16/990,810, filed Aug. 11, 2020, titled "LINKING PATIENT-SPECIFIC MEDICAL DEVICES WITH PATIENT-SPECIFIC DATA, AND ASSOCIATED SYSTEMS, DEVICES, AND METHODS";
- U.S. application Ser. No. 17/085,564, filed Oct. 30, 2020, titled "SYSTEMS AND METHODS FOR DESIGNING ORTHOPEDIC IMPLANTS BASED ON TISSUE CHARACTERISTICS";
- U.S. application Ser. No. 17/100,396, filed Nov. 20, 2020, titled "PATIENT-SPECIFIC VERTEBRAL IMPLANTS WITH POSITIONING FEATURES";
- U.S. application Ser. No. 17/124,822, filed Dec. 17, 2020, titled "PATIENT-SPECIFIC MEDICAL PROCEDURES AND DEVICES, AND ASSOCIATED SYSTEMS AND METHODS"; and
- International Application No. PCT/US2021/012065, filed Jan. 4, 2021, titled "PATIENT-SPECIFIC MEDICAL PROCEDURES AND DEVICES, AND ASSOCIATED SYSTEMS AND METHODS."

All of the above-identified patents and applications are incorporated by reference in their entireties. In addition, the embodiments, features, systems, devices, materials, methods, and techniques described herein may, in certain embodiments, be applied to or used in connection with any one or more of the embodiments, features, systems, devices, or other matter.

As one skilled in the art will appreciate, any of the software modules described previously may be combined into a single software module for performing the operations described herein. Likewise, the software modules can be distributed across any combination of the computing systems and devices described herein, and are not limited to the express arrangements described herein. Accordingly, any of the operations described herein can be performed by any of the computing devices or systems described herein, unless expressly noted otherwise.

EXAMPLES

The present technology is illustrated, for example, according to various aspects described below. Various examples of aspects of the present technology are described as numbered examples (1, 2, 3, etc.) for convenience. These are provided as examples and do not limit the present technology. It is noted that any of the dependent examples can be combined in any suitable manner, and placed into a respective independent example. The other examples can be presented in a similar manner.

1. A computer-implemented method for simulating patient spinal loading, the method comprising:

receiving, first multi-dimensional image data of an anatomical region of a patient in a first loading state;

determining first location coordinates of vertebrae in the first multi-dimensional image data in the first loading state;

determining first rotation, translation, and scaling parameters of the vertebrae in the first multi-dimensional image data in the first loading state;

receiving second multi-dimensional image data of the anatomical region of the patient in a second loading state;

determining second location coordinates of the vertebrae in the second multi-dimensional image data in the second loading state;

determining second rotation, translation, and scaling parameters of the vertebrae in the second multi-dimensional image data in the second loading state; and generating a model of a spine of the patient to simulate spinal loading in the first loading state and the second loading state based on the first location coordinates, the first rotation, translation, and scaling parameters, the second location coordinates, and the second rotation parameters.

2. The computer-implemented method of example 1, further comprising:

determining the first location coordinates and the second location coordinates based on a mapping of the vertebrae to one or more landmarks in the patient.

3. The computer-implemented method of any of examples 1-2, further comprising:

obtaining an aligned multi-dimensional image data of the spine of the patient by aligning corresponding anatomical elements between the first multi-dimensional image data and the second multi-dimensional image data.

4. The computer-implemented method of any of examples 1-3, further comprising:

generating one or more models of one or more vertebrae in the spine of the patient; and inserting the one or more models into the model of the spine according to the first location coordinates, the first rotation parameters, the second location coordinates, and the second rotation, translation, and scaling parameters corresponding to the one or more vertebrae.

5. The computer-implemented method of any of examples 1-4, further comprising:

determining a loading-state mapping based on the first and second loading states; and performing the loading-state mapping between the first multi-dimensional image data and the second multi-dimensional image data to generate aligned multi-dimensional image data.

6. The computer-implemented method of any of examples 1-5, further comprising:

simulating, via the model, compensatory or reciprocal mechanisms to lumbar corrections, wherein the compensatory mechanisms include:

a lumbar compensatory response, a pelvic tilt compensatory response to the lumbar corrections, a thoracic kyphosis compensatory response to the lumbar corrections, or a cervical lordosis compensatory response to the lumbar corrections.

7. The computer-implemented method of any of examples 1-6, wherein the first multi-dimensional image data is obtained from a computer tomography (CT) scan or a magnetic resonance imaging (MRI) scan, and wherein the second multi-dimensional image data is obtained from an X-ray scan.

8. A computer-implemented method for simulating patient spinal loading, the method comprising:

receiving first multi-dimensional image data of an anatomical region of a patient in a first loading state;

receiving second multi-dimensional image data of at least a portion of the anatomical region in a second loading state;

determining one or more loading effects on at least one anatomical element at the anatomical region based on the first and second multi-dimensional image data; and generating a three-dimensional virtual model of the patient to simulate a post-operative loading state based on the one or more loading effects correlated to a pre-operative loading state.

9. The computer-implemented method of example 8, wherein the three-dimensional virtual model includes:

a first set of anatomical element models with high-fidelity surface topologies for designing one or more patient-specific implants, and a second set of anatomical element models for measuring spinal metrics for predicting a surgical outcome associated with implantation of the one or more patient-specific implants, wherein one or more of the anatomical element models of the second set have less feature data than all or some of the anatomical element models of the first set.

10. The computer-implemented method of any of examples 8-9, further comprising:

positioning, orienting, and/or scaling anatomical element models of the first set for incorporation into the second set to generate the three-dimensional virtual model.

11. The computer-implemented method of any of examples 8-10, further comprising:

generating X-ray-fidelity anatomical element models based on one or more standing X-ray images of the second multi-dimensional image data; and generating tomographic-fidelity anatomical element models based on a set of tomographic images of the first multi-dimensional image data, wherein the X-ray-fidelity anatomical element models have a resolution below a threshold fidelity and the tomographic-fidelity anatomical element models have a fidelity above the threshold fidelity.

12. The computer-implemented method of any of examples 8-11, wherein the three-dimensional virtual model is a three-dimensional multi-region simulation model of the patient's spine, the method further including:

generating a three-dimensional multi-region spine model of the patient based on the first multi-dimensional image data;

generating a three-dimensional partial spine model matching a corresponding region of the spine imaged in the second multi-dimensional image data; and generating the three-dimensional multi-region simulation model by combining anatomical elements of the three-dimensional partial spine model with the three-dimensional multi-region spine model.

13. The computer-implemented method of any of examples 8-12, the method further comprising:

replacing lower-fidelity anatomical element models of the three-dimensional multi-region spine model with corresponding higher-fidelity anatomical elements of the three-dimensional partial spine model.

14. The computer-implemented method of any of examples 8-13, wherein the three-dimensional multi-region spine model includes a cervical region and a thoracic region of the patient's spine, and wherein the three-dimensional partial spine model includes a lumbar region model having surface topology data for designing one or more implants.

15. The computer-implemented method of any of examples 8-14, wherein the first multi-dimensional image data shows at least a thoracic region and a cervical region of the patient's spine, wherein the second multi-dimensional image data shows a lumbar region of the patient's spine, and further comprising:

modeling virtual lumbar anatomical elements matching anatomical elements shown in the first multi-dimensional image data based on a resolution level of the first multi-dimensional image data; and modeling virtual anatomical elements of the thoracic region and the cervical region matching anatomical elements shown in the second multi-dimensional image data based on a resolution level of the second multi-dimensional image data.

16. The computer-implemented method of any of examples 8-15, further comprising:

receiving third multi-dimensional image data with the patient in a third loading state matching the second loading state; and generating a replacement virtual model of an anatomical element for placement in the three-dimensional virtual model.

17. The computer-implemented method of any of examples 8-16, further comprising positioning anatomical elements at the anatomical region based on the one or more loading effects.

18. The computer-implemented method of any of examples 8-17, further comprising:

identifying a first image type of the first multi-dimensional image data;

determining the first loading state based on the first image type of the first multi-dimensional image data;

determining one or more anatomical metrics affected by the first loading state; and measuring the one or more anatomical metrics of the anatomical region using the first multi-dimensional image data, wherein the measured one or more anatomical metrics are used to generate the three-dimensional virtual model of a spine.

19. The computer-implemented method of any of examples 8-18, further comprising:

identifying a first image type of the first multi-dimensional image data;

identifying a second image type of the second multi-dimensional image data; and selecting a mapping routine based on the first image type, the second image type, and anatomical elements at the anatomical region.

20. The computer-implemented method of any of examples 8-19, wherein:

the first image type is a CT scan;

the second image type is an X-ray; and the mapping routine is configured to map anatomical features in CT scans to the same anatomical features in X-rays and to determine one or more loading effects at the anatomical region based on positional differences of the same anatomical features attributable to loading during CT scans and X-rays.

21. The computer-implemented method of any of examples 8-20, wherein the three-dimensional virtual model of the spine has rendered virtual surfaces configured for designing one or more implant models with contours matching the rendered virtual surfaces, wherein the three-dimensional virtual model is generated by combining a two-dimensional contemporaneous orthogonal X-rays and three-dimensional MRI data to produce an anatomically loaded 3D spine model.

22. A computer-implemented method for simulating patient spinal loading, the method comprising:

receiving a first multi-dimensional image data of an anatomical region of a patient;

receiving a second multi-dimensional image data of at least a portion of the anatomical region; and generating a multi-fidelity three-dimensional virtual model of the anatomical region, wherein the multi-fidelity three-dimensional virtual model includes:

a first set of anatomical elements generated based on the first multi-dimensional image data, wherein the first set of anatomical elements have a first fidelity for obtaining one or more measurements of the anatomical region, and a second set of anatomical elements generated based on the second multi-dimensional image data, wherein the second set of anatomical elements have a second fidelity for designing one or more implants that fit the second set of anatomical elements.

23. The method of example 22, wherein the first fidelity is below a threshold fidelity, the second fidelity exceeds a threshold fidelity for implant design, and the second fidelity is below the threshold fidelity.

24. The method of any of examples 22-23, wherein the first set of anatomical elements includes at least one of a cervical spine, a thoracic spine, or a lumbar spine of the patient.

25. The method of any of examples 22-24, wherein the first set of anatomical elements represent a cervical spine and a thoracic spine of the patient and the second set of anatomical elements represent the lumbar spine of the patient.

26. The method of any of examples 22-25, further comprising:

simulating one or more lumbar corrections using the multi-fidelity three-dimensional virtual model; and generating, in response to one or more lumbar corrections, at least one of a lumbar compensatory response, a pelvic tilt compensatory response, a thoracic compensatory response, or a cervical compensatory response.

27. The method of any of examples 22-26, further comprising:

applying an imaging modality correction routine to the second set of anatomical elements to position the second set of anatomical elements in the multi-fidelity three-dimensional virtual model.

28. A method comprising:

providing a first set of images and a second set of images of a patient, wherein the images of the first set have a first resolution and the images of the second set have a second resolution different from the first resolution;

obtaining surgical plan information from a surgical planning platform configured to generate a three-dimensional virtual model of the patient's anatomy, wherein the surgical planning platform assigns:

a set of available first tasks to a first region of the three-dimensional virtual model based on the first resolution, wherein the first region is generated using the first set of images, and a set of available second tasks to a second region of the three-dimensional virtual model based on the second resolution, wherein the second region is generated using the second set of images;

receiving a first output from one or more of the first tasks performed using the first region; and receiving a second output from one or more of the first tasks performed using the second region.

29. The method of example 28, wherein the images of the first set are X-rays, and the images of the second set are tomographic scans.

30. The method of any of examples 28-29, wherein the three-dimensional virtual model is a spinal model, and wherein the available first tasks include determining, in response to one or more spinal corrections at the second region, at least one of thoracic kyphosis compensatory response or cervical lordosis compensatory response.

31. The method of any of examples 28-30, wherein the three-dimensional virtual model is a spinal model, and wherein the available second tasks include determining pelvic tilt compensatory response in response to one or more spinal corrections at a lumbar level of the second region.

32. The method of any of examples 28-31, wherein:

the set of available first tasks include determining multi-level spinal correction metrics measured at levels above a lumbar region; and the set of available second tasks include at least one of designing at least one of one or more spinal implants for implantation within the lumbar region; or measuring spinal metrics along the lumbar region.

33. The method of any of examples 28-32, wherein the three-dimensional virtual model represents a corrected spine of the patient.

34. The method of any of examples 28-33, wherein:

the first region of the three-dimensional virtual model includes virtual anatomical elements with X-ray feature details present in X-ray images in the first set; and the second region of the three-dimensional virtual model includes virtual anatomical elements with tomographic feature details present in tomographic images in the second set.

35. A method comprising:

obtaining a first set of patient images and a second set of patient images;

generating, via a surgical planning platform, a three-dimensional multi-fidelity virtual model of the patient's anatomy based on the first and second sets of patient images;

performing, using the surgical planning platform, a first task on a first region of the three-dimensional virtual model based on a first fidelity level of the first region, wherein the first fidelity level corresponds to a first level of image detail of the patient images in the first set; and performing, using the surgical planning platform, a second task on a second region of the three-dimensional virtual model based on a second fidelity level of the second region, wherein the second fidelity level corresponds to a second level of image detail of the patient images in the second set.

36. The method of example 35, wherein the first task includes designing at least one implant surface matching a patient surface, and wherein the surgical planning platform limits available tasks to each of a plurality of regions of the three-dimensional multi-fidelity virtual model based on a level of resolution for that region being acceptable for the available tasks.

37. The method of any of examples 35-36, further comprising assigning usage constraints to the three-dimensional multi-fidelity virtual model based on a fidelity analysis of the three-dimensional multi-fidelity virtual model.

38. The method of any of examples 35-37, wherein the first and second tasks comply with the usage constraints.

39. The method of any of examples 35-38, further comprising displaying the usage constraints to the user and fidelity-dependent tasks capable of being performed using the three-dimensional multi-fidelity virtual model.

40. The method of any of examples 35-39, further comprising determining at least one of the first or second tasks based on at least one fidelity parameter of the three-dimensional multi-fidelity virtual model.

41. A computer-implemented method for medical imaging data, the method comprising:

obtaining a first multi-dimensional image data of an anatomical region of a patient in a first loading state;

determining, from the first multi-dimensional image data, a plurality of regions corresponding to a plurality of anatomical elements of a spine;

identifying, in each of the plurality of regions, a first set of landmarks;

obtaining a second multi-dimensional image data of the anatomical region comprising the spine of the patient in a second loading state;

identifying a second set of landmarks from the second multi-dimensional image data that map to the first set of landmarks;

obtaining an aligned multi-dimensional image data of the patient's spine by aligning corresponding anatomical elements between the first multi-dimensional image data and the second multi-dimensional image data;

generating a design for a medical implant based on spinopelvic parameters measured from the aligned multi-dimensional image data; and causing a medical implant to be manufactured by sending the design for the medical implant to a manufacturing device.

42. The computer-implemented method of example 41, wherein the first multi-dimensional image data is collected in three dimensions, and wherein the second multi-dimensional image data is collected in two dimensions.

43. The computer-implemented method of any of examples 41-42, wherein the aligned multi-dimensional image data is a three-dimensional image.

44. The computer-implemented method of any of examples 41-43, wherein the obtaining the aligned multi-dimensional image data includes:

modifying positions of the plurality of anatomical elements in the first multi-dimensional image data according to positions of the plurality of anatomical elements in the second multi-dimensional image data.

45. The computer-implemented method of any of examples 41-44, further comprising:

determining a loading-state mapping based on the first and second loading states; and performing the loading-state mapping between the first multi-dimensional image data and the second multi-dimensional image data to generate the aligned multi-dimensional image data.

46. The computer-implemented method of any of examples 41-45, wherein in response to a region being a lumbar vertebra, the identifying the first set of landmarks of the region includes identifying the following:

an inferior aspect of spinous process of the lumbar vertebrae, a superior aspect of spinous process of the lumbar vertebrae, a left aspect of transverse process of the lumbar vertebrae, and a right aspect of transverse process of the lumbar vertebrae.

47. The computer-implemented method of any of examples 41-46, wherein the aligning the corresponding anatomical elements between the first multi-dimensional image data and the second multi-dimensional image data includes aligning a sacrum between a three-dimensional (3D) image data and a two-dimensional (2D) image data by:

creating, from the 3D image data, a first image data along a sagittal view that bisects the sacrum;

projecting a second image data along the sagittal view from the 2D image data onto the first image data, wherein the second image data comprises the sacrum; and causing the sacrum from the first image data to overlap with the sacrum of the second image data by scaling, rotating, and/or translating the first image data.

48. The computer-implemented method of any of examples 41-47, wherein the aligning the corresponding anatomical elements includes aligning each lumbar vertebra between the 3D image data and the 2D image data that is performed in response to the aligning the sacrum by:

performing a first aligning operation of a lumbar vertebra by moving an anterior landmark and a posterior landmark of the lumbar vertebra in the 3D image data to match the same landmarks on the second image data from the 2D image data, wherein the second image data comprises the lumbar vertebra;

creating, from the 3D image data, a third image data along a coronal view that extends across the sacrum;

projecting a fourth image data along the coronal view from the 2D image data onto the third image data, wherein the fourth image data comprises the sacrum;

causing the sacrum from the third image data to overlap with the sacrum of the second image data by scaling or translating the first image data; and performing a second aligning operation of the lumbar vertebra by moving the anterior landmark and the posterior landmark for the lumbar vertebra to match the same landmarks on the fourth image data from the 2D image, wherein the fourth image data comprises the lumbar vertebra.

49. The computer-implemented method of any of examples 41-48, further comprising:

adjusting one or more other landmarks of the lumbar vertebra by a same amount as that used to move the anterior landmark and the posterior landmark of the lumbar vertebra in the 3D image data for the first aligning operation; and adjusting one or more other landmarks of the lumbar vertebra by a same amount as that used to move the anterior landmark and the posterior landmark of the lumbar vertebra in the 3D image data for the second aligning operation.

50. The computer-implemented method of any of examples 41-49, wherein the first multi-dimensional image data is obtained from a computer tomography (CT) scan or a magnetic resonance imaging (MRI) scan, and wherein the second multi-dimensional image data is obtained from an X-ray scan.

51. A non-transitory computer-readable storage medium storing instructions that, when executed by a computing system, cause the computing system to perform a method comprising:

obtaining a first multi-dimensional image data of an anatomical region of a patient in a first loading state;

determining, from the first multi-dimensional image data, a plurality of regions corresponding to a plurality of anatomical elements of a spine;

identifying, in each of the plurality of regions, a first set of landmarks;

obtaining a second multi-dimensional image data of the anatomical region comprising the spine of the patient in a second loading state;

identifying a second set of landmarks from the second multi-dimensional image data that map to the first set of landmarks;

obtaining an aligned multi-dimensional image data of the patient's spine by aligning corresponding anatomical elements between the first multi-dimensional image data and the second multi-dimensional image data;

generating a design for a medical implant based on spinopelvic parameters measured from the aligned multi-dimensional image data; and causing a medical implant to be manufactured by sending the design for the medical implant to a manufacturing device.

52. The non-transitory computer-readable storage medium of example 51, wherein the first multi-dimensional image data is collected in three dimensions, and wherein the second multi-dimensional image data is collected in two dimensions.

53. The non-transitory computer-readable storage medium of any of examples 51-52, wherein the aligned multi-dimensional image data is a three-dimensional image.

54. The non-transitory computer-readable storage medium of any of examples 51-53, wherein the obtaining the aligned multi-dimensional image data includes:

modifying positions of the plurality of anatomical elements in the first multi-dimensional image data according to positions of the plurality of anatomical elements in the second multi-dimensional image data.

55. The non-transitory computer-readable storage medium of any of examples 51-54, further comprising:

determining a loading-state mapping based on the first and second loading states; and performing the loading-state mapping between the first multi-dimensional image data and the second multi-dimensional image data to generate the aligned multi-dimensional image data.

56. The non-transitory computer-readable storage medium of any of examples 51-55, wherein in response to a region being a lumbar vertebra, the identifying the first set of landmarks of the region includes identifying the following:

an inferior aspect of spinous process of the lumbar vertebrae, a superior aspect of spinous process of the lumbar vertebrae, a left aspect of transverse process of the lumbar vertebrae, and a right aspect of transverse process of the lumbar vertebrae.

57. The non-transitory computer-readable storage medium of any of examples 51-56, wherein the aligning the corresponding anatomical elements between the first multi-dimensional image data and the second multi-dimensional image data includes aligning a sacrum between a three-dimensional (3D) image data and a two-dimensional (2D) image data by:

creating, from the 3D image data, a first image data along a sagittal view that bisects the sacrum;

projecting a second image data along the sagittal view from the 2D image data onto the first image data, wherein the second image data comprises the sacrum; and causing the sacrum from the first image data to overlap with the sacrum of the second image data by scaling, rotating, and/or translating the first image data.

58. The non-transitory computer-readable storage medium of any of examples 51-57, wherein the aligning the corresponding anatomical elements includes aligning each lumbar vertebra between the 3D image data and the 2D image data that is performed in response to the aligning the sacrum by:

performing a first aligning operation of a lumbar vertebra by moving an anterior landmark and a posterior landmark of the lumbar vertebra in the 3D image data to match the same landmarks on the second image data from the 2D image data, wherein the second image data comprises the lumbar vertebra;

creating, from the 3D image data, a third image data along a coronal view that extends across the sacrum;

projecting a fourth image data along the coronal view from the 2D image data onto the third image data, wherein the fourth image data comprises the sacrum;

causing the sacrum from the third image data to overlap with the sacrum of the second image data by scaling or translating the first image data; and performing a second aligning operation of the lumbar vertebra by moving the anterior landmark and the posterior landmark for the lumbar vertebra to match the same landmarks on the fourth image data from the 2D image, wherein the fourth image data comprises the lumbar vertebra.

59. The non-transitory computer-readable storage medium of any of examples 51-58, wherein the method further comprises:

adjusting one or more other landmarks of the lumbar vertebra by a same amount as that used to move the anterior landmark and the posterior landmark of the lumbar vertebra in the 3D image data for the first aligning operation; and adjusting one or more other landmarks of the lumbar vertebra by a same amount as that used to move the anterior landmark and the posterior landmark of the lumbar vertebra in the 3D image data for the second aligning operation.

60. The non-transitory computer-readable storage medium of any of examples 51-59, wherein the first multi-dimensional image data is obtained from a computer tomography (CT) scan or a magnetic resonance imaging (MRI) scan, and wherein the second multi-dimensional image data is obtained from an X-ray scan.

61. A system for medical imaging data, the system comprising one or more processors and a memory storing instructions that, when executed by the one or more processors, cause the system to:

obtain a first multi-dimensional image data of an anatomical region of a patient in a first loading state;

determine, from the first multi-dimensional image data, a plurality of regions corresponding to a plurality of anatomical elements of a spine;

identify, in each of the plurality of regions, a first set of landmarks;

obtain a second multi-dimensional image data of the anatomical region comprising the spine of the patient in a second loading state;

identify a second set of landmarks from the second multi-dimensional image data that map to the first set of landmarks;

obtain an aligned multi-dimensional image data of the patient's spine by aligning corresponding anatomical elements between the first multi-dimensional image data and the second multi-dimensional image data;

generate a design for a medical implant based on spinopelvic parameters measured from the aligned multi-dimensional image data; and cause a medical implant to be manufactured by sending the design for the medical implant to a manufacturing device.

62. The system of example 61, wherein the first multi-dimensional image data is collected in three dimensions, and wherein the second multi-dimensional image data is collected in two dimensions.

63. The system of any of examples 61-62, wherein the aligned multi-dimensional image data is a three-dimensional image.

64. The system of any of examples 61-63, wherein the obtaining the aligned multi-dimensional image data includes:

modifying positions of the plurality of anatomical elements in the first multi-dimensional image data according to positions of the plurality of anatomical elements in the second multi-dimensional image data.

65. The system of any of examples 61-64, further comprising:

determining a loading-state mapping based on the first and second loading states; and performing the loading-state mapping between the first multi-dimensional image data and the second multi-dimensional image data to generate the aligned multi-dimensional image data.

66. The system of any of examples 61-65, wherein in response to a region being a lumbar vertebra, the identifying the first set of landmarks of the region includes identifying the following:

an inferior aspect of spinous process of the lumbar vertebrae, a superior aspect of spinous process of the lumbar vertebrae, a left aspect of transverse process of the lumbar vertebrae, and a right aspect of transverse process of the lumbar vertebrae.

67. The system of any of examples 61-66, wherein the aligning the corresponding anatomical elements between the first multi-dimensional image data and the second multi-dimensional image data includes aligning a sacrum between a three-dimensional (3D) image data and a two-dimensional (2D) image data by:

creating, from the 3D image data, a first image data along a sagittal view that bisects the sacrum;

projecting a second image data along the sagittal view from the 2D image data onto the first image data, wherein the second image data comprises the sacrum; and causing the sacrum from the first image data to overlap with the sacrum of the second image data by scaling, rotating, and/or translating the first image data.

68. The system of any of examples 61-67, wherein the aligning the corresponding anatomical elements includes aligning each lumbar vertebra between the 3D image data and the 2D image data that is performed in response to the aligning the sacrum by:

performing a first aligning operation of a lumbar vertebra by moving an anterior landmark and a posterior landmark of the lumbar vertebra in the 3D image data to match the same landmarks on the second image data from the 2D image data, wherein the second image data comprises the lumbar vertebra;

creating, from the 3D image data, a third image data along a coronal view that extends across the sacrum;

projecting a fourth image data along the coronal view from the 2D image data onto the third image data, wherein the fourth image data comprises the sacrum;

causing the sacrum from the third image data to overlap with the sacrum of the second image data by scaling or translating the first image data; and performing a second aligning operation of the lumbar vertebra by moving the anterior landmark and the posterior landmark for the lumbar vertebra to match the same landmarks on the fourth image data from the 2D image, wherein the fourth image data comprises the lumbar vertebra.

69. The system of any of examples 61-68, further comprising:

adjusting one or more other landmarks of the lumbar vertebra by a same amount as that used to move the anterior landmark and the posterior landmark of the lumbar vertebra in the 3D image data for the first aligning operation; and adjusting one or more other landmarks of the lumbar vertebra by a same amount as that used to move the anterior landmark and the posterior landmark of the lumbar vertebra in the 3D image data for the second aligning operation.

70. The system of any of examples 61-69, wherein the first multi-dimensional image data is obtained from a computer tomography (CT) scan or a magnetic resonance imaging (MRI) scan, and wherein the second multi-dimensional image data is obtained from an X-ray scan.

71. A computing system comprising:

one or more processors; and one or more memories storing instructions that, when executed by the one or more processors, cause the computing system to perform a process of any of examples 1-70.

72. A non-transitory computer-readable medium storing instructions that, when executed by a computing system, cause the computing system to perform operations of any of examples 1-70.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable-type medium such as a floppy disk, a hard disk drive, a CD, a DVD, a digital tape, a computer memory, etc.; and a transmission-type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable" to each other to achieve the desired functionality. Specific examples of operably couplable include, but are not limited to, physically mateable and/or physically interacting components and/or wirelessly interactable and/or wirelessly interacting components and/or logically interacting and/or logically interactable components.

All of the above-identified patents and applications are incorporated by reference in their entireties. In addition, the embodiments, features, systems, devices, materials, methods, and techniques described herein may, in certain embodiments, be applied to or used in connection with any one or more of the embodiments, features, systems, devices, or other matter.

The ranges disclosed herein also encompass any and all overlap, sub-ranges, and combinations thereof. Language such as "up to," "at least," "greater than," "less than," "between," or the like includes the number recited. Numbers preceded by a term such as "approximately," "about," and "substantially" as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A computer-implemented method for simulating patient spinal loading, the method comprising:

receiving, first multi-dimensional image data of an anatomical region of a patient in a first loading state;

determining first location coordinates of vertebrae in the first multi-dimensional image data in the first loading state;

determining first rotation, translation, and scaling parameters of the vertebrae in the first multi-dimensional image data in the first loading state;

receiving second multi-dimensional image data of the anatomical region of the patient in a second loading state;

determining second location coordinates of the vertebrae in the second multi-dimensional image data in the second loading state;

determining second rotation, translation, and scaling parameters of the vertebrae in the second multi-dimensional image data in the second loading state; and generating a model of a spine of the patient to simulate spinal loading in the first loading state and the second loading state based on the first location coordinates, the first rotation, translation, and scaling parameters, the second location coordinates, and the second rotation parameters.

2. The computer-implemented method of claim 1, further comprising:

determining the first location coordinates and the second location coordinates based on a mapping of the vertebrae to one or more landmarks in the patient.

3. The computer-implemented method of claim 1, further comprising:

obtaining an aligned multi-dimensional image data of the spine of the patient by aligning corresponding anatomical elements between the first multi-dimensional image data and the second multi-dimensional image data.

4. The computer-implemented method of claim 1, further comprising:

generating one or more models of one or more vertebrae in the spine of the patient; and inserting the one or more models into the model of the spine according to the first location coordinates, the first rotation parameters, the second location coordinates, and the second rotation, translation, and scaling parameters corresponding to the one or more vertebrae.

5. The computer-implemented method of claim 1, further comprising:

determining a loading-state mapping based on the first and second loading states; and performing the loading-state mapping between the first multi-dimensional image data and the second multi-dimensional image data to generate aligned multi-dimensional image data.

6. The computer-implemented method of claim 1, further comprising:

simulating, via the model, compensatory or reciprocal mechanisms to lumbar corrections, wherein the compensatory mechanisms include:

a lumbar compensatory response, a pelvic tilt compensatory response to the lumbar corrections, a thoracic kyphosis compensatory response to the lumbar corrections, or a cervical lordosis compensatory response to the lumbar corrections.

7. The computer-implemented method of claim 1, wherein the first multi-dimensional image data is obtained from a computer tomography (CT) scan or a magnetic resonance imaging (MRI) scan, and wherein the second multi-dimensional image data is obtained from an X-ray scan.

8. A computer-implemented method for simulating patient spinal loading, the method comprising:

receiving first multi-dimensional image data of an anatomical region of a patient in a first loading state, wherein the first multi-dimensional image data shows at least a thoracic region and a cervical region of a spine of the patient;

modeling virtual lumbar anatomical elements matching anatomical elements shown in the first multi-dimensional image data based on a resolution level of the first multi-dimensional image data;

receiving second multi-dimensional image data of at least a portion of the anatomical region in a second loading state, wherein the second multi-dimensional image data shows a lumbar region of the spine of the patient;

modeling virtual anatomical elements of the thoracic region and the cervical region matching anatomical elements shown in the second multi-dimensional image data based on a resolution level of the second multi-dimensional image data;

determining one or more loading effects on at least one anatomical element at the anatomical region based on the first and second multi-dimensional image data; and generating a three-dimensional virtual model of the patient to simulate a post-operative loading state based on the one or more loading effects correlated to a pre-operative loading state.

9. The computer-implemented method of claim 8, further comprising:

receiving third multi-dimensional image data with the patient in a third loading state matching the second loading state; and generating a replacement virtual model of an anatomical element for placement in the three-dimensional virtual model.

10. The computer-implemented method of claim 8, further comprising positioning anatomical elements at the anatomical region based on the one or more loading effects.

11. A computer-implemented method for simulating patient spinal loading, the method comprising:

receiving first multi-dimensional image data of an anatomical region of a patient in a first loading state;

receiving second multi-dimensional image data of at least a portion of the anatomical region in a second loading state;

determining one or more loading effects on at least one anatomical element at the anatomical region based on the first and second multi-dimensional image data; and generating a three-dimensional virtual model of the patient to simulate a post-operative loading state based on the one or more loading effects correlated to a pre-operative loading state, wherein the three-dimensional virtual model includes:

a first set of anatomical element models with high-fidelity surface topologies for designing one or more patient-specific implants, and a second set of anatomical element models for measuring spinal metrics for predicting a surgical outcome associated with implantation of the one or more patient-specific implants, wherein one or more of the anatomical element models of the second set have less feature data than all or some of the anatomical element models of the first set.

12. The computer-implemented method of claim 11, further comprising:

positioning, orienting, and/or scaling anatomical element models of the first set for incorporation into the second set to generate the three-dimensional virtual model.

13. The computer-implemented method of claim 11, further comprising:

generating X-ray-fidelity anatomical element models based on one or more standing X-ray images of the second multi-dimensional image data; and generating tomographic-fidelity anatomical element models based on a set of tomographic images of the first multi-dimensional image data, wherein the X-ray-fidelity anatomical element models have a resolution below a threshold fidelity and the tomographic-fidelity anatomical element models have a fidelity above the threshold fidelity.

14. A method for simulating patient spinal loading, the method comprising:

receiving first multi-dimensional image data of an anatomical region of a patient in a first loading state;

receiving second multi-dimensional image data of at least a portion of the anatomical region in a second loading state;

determining one or more loading effects on at least one anatomical element at the anatomical region based on the first and second multi-dimensional image data; and generating a three-dimensional virtual model of the patient to simulate a post-operative loading state based on the one or more loading effects correlated to a pre-operative loading state, wherein the three-dimensional virtual model is a three-dimensional multi-region simulation model of a spine of the patient generated by:

generating a three-dimensional multi-region spine model of the patient based on the first multi-dimensional image data;

generating a three-dimensional partial spine model matching a corresponding region of the spine imaged in the second multi-dimensional image data; and generating the three-dimensional multi-region simulation model by combining anatomical elements of the three-dimensional partial spine model with the three-dimensional multi-region spine model.

15. The computer-implemented method of claim 14, wherein the three-dimensional multi-region spine model includes a cervical region and a thoracic region of the patient's spine, and wherein the three-dimensional partial spine model includes a lumbar region model having surface topology data for designing one or more implants.

16. A method for simulating patient spinal loading, the method comprising:

receiving first multi-dimensional image data of an anatomical region of a patient in a first loading state;

receiving second multi-dimensional image data of at least a portion of the anatomical region in a second loading state;

determining one or more loading effects on at least one anatomical element at the anatomical region based on the first and second multi-dimensional image data;

generating a three-dimensional multi-region spine model of the patient to simulate a post-operative loading state based on the one or more loading effects correlated to a pre-operative loading state, and replacing lower-fidelity anatomical element models of the three-dimensional multi-region spine model with corresponding higher-fidelity anatomical elements of a three-dimensional partial spine model.

17. A method for simulating patient spinal loading, the method comprising:

receiving first multi-dimensional image data of an anatomical region of a patient in a first loading state;

identifying a first image type of the first multi-dimensional image data;

determining the first loading state based on the first image type of the first multi-dimensional image data;

determining one or more anatomical metrics affected by the first loading state;

receiving second multi-dimensional image data of at least a portion of the anatomical region in a second loading state;

determining one or more loading effects on at least one anatomical element at the anatomical region based on the first and second multi-dimensional image data;

measuring the one or more anatomical metrics of the anatomical region using the first multi-dimensional image data; and generating a three-dimensional virtual model of the patient to simulate a post-operative loading state based on the one or more loading effects correlated to a pre-operative loading state, wherein the measured one or more anatomical metrics are used to generate the three-dimensional virtual model of a spine.

18. A method for simulating patient spinal loading, the method comprising:

receiving first multi-dimensional image data of an anatomical region of a patient in a first loading state;

receiving second multi-dimensional image data of at least a portion of the anatomical region in a second loading state;

identifying a first image type of the first multi-dimensional image data;

identifying a second image type of the second multi-dimensional image data;

selecting a mapping routine based on the first image type, the second image type, and anatomical elements at the anatomical region;

determining one or more loading effects on at least one anatomical element at the anatomical region based on the first and second multi-dimensional image data; and generating a three-dimensional virtual model of the patient to simulate a post-operative loading state based on the one or more loading effects correlated to a pre-operative loading state.

19. The computer-implemented method of claim 18, wherein:

the first image type is a CT scan;

the second image type is an X-ray; and the mapping routine is configured to map anatomical features in CT scans to the same anatomical features in X-rays and to determine one or more loading effects at the anatomical region based on positional differences of the same anatomical features attributable to loading during CT scans and X-rays.

20. A method for simulating patient spinal loading, the method comprising:

receiving first multi-dimensional image data of an anatomical region of a patient in a first loading state;

receiving second multi-dimensional image data of at least a portion of the anatomical region in a second loading state;

determining one or more loading effects on at least one anatomical element at the anatomical region based on the first and second multi-dimensional image data; and generating a three-dimensional virtual model of the patient to simulate a post-operative loading state based on the one or more loading effects correlated to a pre-operative loading state, wherein the three-dimensional virtual model of a spine has rendered virtual surfaces configured for designing one or more implant models with contours matching the rendered virtual surfaces, wherein the three-dimensional virtual model is generated by combining a two-dimensional contemporaneous orthogonal X-rays and three-dimensional MRI data to produce an anatomically loaded 3D spine model.

21. A computer-implemented method for simulating patient spinal loading, the method comprising:

receiving a first multi-dimensional image data of an anatomical region of a patient;

receiving a second multi-dimensional image data of at least a portion of the anatomical region; and generating a multi-fidelity three-dimensional virtual model of the anatomical region, wherein the multi-fidelity three-dimensional virtual model includes:

a first set of anatomical elements generated based on the first multi-dimensional image data, wherein the first set of anatomical elements have a first fidelity for obtaining one or more measurements of the anatomical region, and a second set of anatomical elements generated based on the second multi-dimensional image data, wherein the second set of anatomical elements have a second fidelity for designing one or more implants that fit the second set of anatomical elements.

22. The method of claim 21, wherein the first fidelity is below a threshold fidelity, the second fidelity exceeds a threshold fidelity for implant design, and the second fidelity is below the threshold fidelity.

23. The method of claim 21, wherein the first set of anatomical elements includes at least one of a cervical spine, a thoracic spine, or a lumbar spine of the patient.

24. The method of claim 21, wherein the first set of anatomical elements represent a cervical spine and a thoracic spine of the patient and the second set of anatomical elements represent a lumbar spine of the patient.

25. The method of claim 21, further comprising:

simulating one or more lumbar corrections using the multi-fidelity three-dimensional virtual model; and generating, in response to one or more lumbar corrections, at least one of a lumbar compensatory response, a pelvic tilt compensatory response, a thoracic compensatory response, or a cervical compensatory response.

26. The method of claim 21, further comprising:

applying an imaging modality correction routine to the second set of anatomical elements to position the second set of anatomical elements in the multi-fidelity three-dimensional virtual model.

27. The method of claim 21, wherein the first multi-dimensional image data includes two-dimensional imaging data of the patient standing, and the second multi-dimensional image data of the patient laying down.

28. The method of claim 21, further comprising generating a virtual implant implanted along the multi-fidelity three-dimensional virtual model of the anatomical region, wherein the multi-fidelity three-dimensional virtual model represents a spine of the patient.

29. A system comprising:

one or more processors; and one or more memories storing instructions that, when executed by the one or more processors, cause the system to perform a process for simulating patient spinal loading, the process comprising:

receiving, first multi-dimensional image data of an anatomical region of a patient in a first loading state;

determining first location coordinates of vertebrae in the first multi-dimensional image data in the first loading state;

determining first rotation, translation, and scaling parameters of the vertebrae in the first multi-dimensional image data in the first loading state;

receiving second multi-dimensional image data of the anatomical region of the patient in a second loading state;

determining second location coordinates of the vertebrae in the second multi-dimensional image data in the second loading state;

determining second rotation, translation, and scaling parameters of the vertebrae in the second multi-dimensional image data in the second loading state; and generating a model of a spine of the patient to simulate spinal loading in the first loading state and the second loading state based on the first location coordinates, the first rotation, translation, and scaling parameters, the second location coordinates, and the second rotation parameters.

30. A non-transitory computer-readable medium storing instructions that, when executed by a computing system, cause the computing system to perform operations for simulating patient spinal loading, the operations comprising:

receiving, first multi-dimensional image data of an anatomical region of a patient in a first loading state;

determining first location coordinates of vertebrae in the first multi-dimensional image data in the first loading state;

determining first rotation, translation, and scaling parameters of the vertebrae in the first multi-dimensional image data in the first loading state;

receiving second multi-dimensional image data of the anatomical region of the patient in a second loading state;

determining second location coordinates of the vertebrae in the second multi-dimensional image data in the second loading state;

determining second rotation, translation, and scaling parameters of the vertebrae in the second multi-dimensional image data in the second loading state; and generating a model of a spine of the patient to simulate spinal loading in the first loading state and the second loading state based on the first location coordinates, the first rotation, translation, and scaling parameters, the second location coordinates, and the second rotation parameters.

31. A system comprising:

one or more processors; and one or more memories storing instructions that, when executed by the one or more processors, cause the system to perform a process for simulating patient spinal loading, the process comprising:

receiving first multi-dimensional image data of an anatomical region of a patient in a first loading state, wherein the first multi-dimensional image data shows at least a thoracic region and a cervical region of a spine of the patient;

modeling virtual lumbar anatomical elements matching anatomical elements shown in the first multi-dimensional image data based on a resolution level of the first multi-dimensional image data;

receiving second multi-dimensional image data of at least a portion of the anatomical region in a second loading state, wherein the second multi-dimensional image data shows a lumbar region of the spine of the patient;

modeling virtual anatomical elements of the thoracic region and the cervical region matching anatomical elements shown in the second multi-dimensional image data based on a resolution level of the second multi-dimensional image data;

determining one or more loading effects on at least one anatomical element at the anatomical region based on the first and second multi-dimensional image data; and generating a three-dimensional virtual model of the patient to simulate a post-operative loading state based on the one or more loading effects correlated to a pre-operative loading state.

32. A non-transitory computer-readable medium storing instructions that, when executed by a computing system, cause the computing system to perform operations for simulating patient spinal loading, the operations comprising:

receiving first multi-dimensional image data of an anatomical region of a patient in a first loading state, wherein the first multi-dimensional image data shows at least a thoracic region and a cervical region of a spine of the patient;

modeling virtual lumbar anatomical elements matching anatomical elements shown in the first multi-dimensional image data based on a resolution level of the first multi-dimensional image data;

receiving second multi-dimensional image data of at least a portion of the anatomical region in a second loading state, wherein the second multi-dimensional image data shows a lumbar region of the spine of the patient;

modeling virtual anatomical elements of the thoracic region and the cervical region matching anatomical elements shown in the second multi-dimensional image data based on a resolution level of the second multi-dimensional image data;

determining one or more loading effects on at least one anatomical element at the anatomical region based on the first and second multi-dimensional image data; and generating a three-dimensional virtual model of the patient to simulate a post-operative loading state based on the one or more loading effects correlated to a pre-operative loading state.

33. A system comprising:

one or more processors; and one or more memories storing instructions that, when executed by the one or more processors, cause the system to perform a process for simulating patient spinal loading, the process comprising:

receiving a first multi-dimensional image data of an anatomical region of a patient;

receiving a second multi-dimensional image data of at least a portion of the anatomical region; and generating a multi-fidelity three-dimensional virtual model of the anatomical region, wherein the multi-fidelity three-dimensional virtual model includes:

a first set of anatomical elements generated based on the first multi-dimensional image data, wherein the first set of anatomical elements have a first fidelity for obtaining one or more measurements of the anatomical region, and a second set of anatomical elements generated based on the second multi-dimensional image data, wherein the second set of anatomical elements have a second fidelity for designing one or more implants that fit the second set of anatomical elements.

34. A non-transitory computer-readable medium storing instructions that, when executed by a computing system, cause the computing system to perform operations for simulating patient spinal loading, the operations comprising:

receiving a first multi-dimensional image data of an anatomical region of a patient;

receiving a second multi-dimensional image data of at least a portion of the anatomical region; and generating a multi-fidelity three-dimensional virtual model of the anatomical region, wherein the multi-fidelity three-dimensional virtual model includes:

a first set of anatomical elements generated based on the first multi-dimensional image data, wherein the first set of anatomical elements have a first fidelity for obtaining one or more measurements of the anatomical region, and a second set of anatomical elements generated based on the second multi-dimensional image data, wherein the second set of anatomical elements have a second fidelity for designing one or more implants that fit the second set of anatomical elements.

* * * * *